(12) United States Patent
Kang et al.

(10) Patent No.: US 11,866,700 B2
(45) Date of Patent: *Jan. 9, 2024

(54) LIPOSOMAL SPHERICAL NUCLEIC ACID (SNA) CONSTRUCTS PRESENTING ANTISENSE OLIGONUCLEOTIDES (ASO) FOR SPECIFIC KNOCKDOWN OF INTERLEUKIN 17 RECEPTOR MRNA

(71) Applicant: Exicure Operating Company, Chicago, IL (US)

(72) Inventors: Richard Kang, Wilmette, IL (US); Scott Mix, Chicago, IL (US); Ekambar Kandimalla, Hopkinton, MA (US)

(73) Assignee: Exicure Operating Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/099,385

(22) PCT Filed: May 5, 2017

(86) PCT No.: PCT/US2017/031428
§ 371 (c)(1),
(2) Date: Nov. 6, 2018

(87) PCT Pub. No.: WO2017/193087
PCT Pub. Date: Nov. 9, 2017

(65) Prior Publication Data
US 2020/0308579 A1    Oct. 1, 2020

Related U.S. Application Data

(60) Provisional application No. 62/333,082, filed on May 6, 2016.

(51) Int. Cl.
| | | |
|---|---|---|
| *C12N 15/11* | (2006.01) | |
| *C12N 15/113* | (2010.01) | |
| *A61K 47/69* | (2017.01) | |
| *A61K 47/54* | (2017.01) | |
| *A61K 31/712* | (2006.01) | |
| *A61K 31/7125* | (2006.01) | |
| *A61K 31/713* | (2006.01) | |
| *A61K 9/06* | (2006.01) | |

(52) U.S. Cl.
CPC .......... *C12N 15/113* (2013.01); *A61K 31/712* (2013.01); *A61K 31/713* (2013.01); *A61K 31/7125* (2013.01); *A61K 47/554* (2017.08); *A61K 47/6911* (2017.08); *A61K 9/06* (2013.01); *C12N 2310/11* (2013.01); *C12N 2310/315* (2013.01); *C12N 2310/341* (2013.01)

(58) Field of Classification Search
CPC ............ C12N 15/113; C12N 2310/315; C12N 2310/341; C12N 2310/11; A61K 47/6911; A61K 31/712; A61K 31/7125
See application file for complete search history.

(56) References Cited

U.S. PATENT DOCUMENTS

| | | |
|---|---|---|
| 5,264,618 A | 11/1993 | Felgner et al. |
| 5,472,881 A | 12/1995 | Beebe et al. |
| 5,512,439 A | 4/1996 | Hornes et al. |
| 5,869,286 A | 2/1999 | Yao et al. |
| 5,955,589 A | 9/1999 | Cook et al. |
| 6,051,698 A | 4/2000 | Janjic et al. |
| 6,072,033 A | 6/2000 | Yao et al. |
| 6,072,037 A | 6/2000 | Yao et al. |
| 6,096,305 A | 8/2000 | Yao et al. |
| 6,100,235 A | 8/2000 | Yao et al. |
| 6,191,104 B1 | 2/2001 | Spriggs et al. |
| 6,197,525 B1 | 3/2001 | Yao et al. |
| 6,214,806 B1 | 4/2001 | Krieg et al. |
| 6,218,371 B1 | 4/2001 | Krieg et al. |
| 6,339,068 B1 | 1/2002 | Krieg et al. |
| 6,361,944 B1 | 3/2002 | Mirkin et al. |
| 6,429,199 B1 | 8/2002 | Krieg et al. |
| 6,482,923 B1 | 11/2002 | Shi et al. |
| 6,506,564 B1 | 1/2003 | Mirkin et al. |
| 6,562,578 B1 | 5/2003 | Gorman et al. |
| 6,569,419 B2 | 5/2003 | Moore et al. |
| 6,569,645 B2 | 5/2003 | Chen et al. |
| 6,579,520 B2 | 6/2003 | Chen et al. |
| 6,635,443 B1 | 10/2003 | Shi et al. |
| 6,849,719 B2 | 2/2005 | Shi et al. |

(Continued)

FOREIGN PATENT DOCUMENTS

| | | |
|---|---|---|
| CN | 1335884 A | 2/2002 |
| CN | 1341660 A | 3/2002 |

(Continued)

OTHER PUBLICATIONS

Rubenstein et al, Antisense oligonucleotide intralesional therapy for human PC-3 prostate tumors carried in athymic nude mice, Journal of Surgical Oncology, 1996, 62: 194-200 (Year: 1996).*
Hurst et al, Maximizing DNA Loading on a Range of Gold Nanoparticle Sizes, Anal.Chem., 2006, 78: 8313-8318 (Year: 2006).*
IDT catalog, 2023, pp. 1-2 (Year: 2023).*
International Preliminary Report on Patentability dated Nov. 15, 2018 in connection with PCT/US2017/031428.
Partial Supplementary European Search Report dated Nov. 22, 2019 in connection with EP 17793513.7.

(Continued)

*Primary Examiner* — Ekaterina Poliakova-Georgantas

(74) *Attorney, Agent, or Firm* — Wolf, Greenfield & Sacks, P.C.

(57) ABSTRACT

Aspects of the invention relate to antisense oligonucleotides directed to the interleukin 17 receptor (IL-17R), and other targets. Spherical nucleic acid formulations or compositions of antisense oligonucleotides and related methods of treatment are also provided.

21 Claims, 12 Drawing Sheets

Specification includes a Sequence Listing.

(56) References Cited

U.S. PATENT DOCUMENTS

| | | | |
|---|---|---|---|
| 6,902,735 B1 | 6/2005 | Jacobs et al. | |
| 7,094,566 B2 | 8/2006 | Medlock et al. | |
| 7,094,886 B2 | 8/2006 | Shaughnessy | |
| 7,115,398 B2 | 10/2006 | Chen et al. | |
| 7,217,412 B2 | 5/2007 | Chen et al. | |
| 7,256,264 B2 | 8/2007 | Goddard et al. | |
| 7,332,586 B2 | 2/2008 | Franzen et al. | |
| 7,404,969 B2 | 7/2008 | Chen et al. | |
| 7,473,763 B2 | 1/2009 | Goddard et al. | |
| 7,514,099 B2 | 4/2009 | Chen et al. | |
| 7,544,482 B2 | 6/2009 | Goddard et al. | |
| 7,611,857 B2 | 11/2009 | Medlock et al. | |
| 7,638,603 B2 | 12/2009 | Shi et al. | |
| 7,655,761 B2 | 2/2010 | Gorman et al. | |
| 7,696,150 B2 | 4/2010 | Shaughnessy | |
| 7,718,397 B2 | 5/2010 | Goddard et al. | |
| 7,771,719 B1 | 8/2010 | Filvaroff et al. | |
| 7,833,992 B2 | 11/2010 | Vargeese et al. | |
| 7,879,980 B2 | 2/2011 | Golstein et al. | |
| 7,943,738 B2 | 5/2011 | Medlock et al. | |
| 7,956,176 B2 | 6/2011 | McSwiggen et al. | |
| 7,964,578 B2 | 6/2011 | Vargeese et al. | |
| 7,993,659 B2 | 8/2011 | Noelle et al. | |
| 8,133,734 B2 | 3/2012 | Shi et al. | |
| 8,188,254 B2 | 5/2012 | Uhlmann et al. | |
| 8,202,979 B2 | 6/2012 | McSwiggen et al. | |
| 8,273,866 B2 | 9/2012 | McSwiggen et al. | |
| 8,323,686 B2 | 12/2012 | Mirkin et al. | |
| 8,338,132 B2 | 12/2012 | Chen et al. | |
| 8,431,544 B1 | 4/2013 | Agrawal et al. | |
| 8,455,217 B2 | 6/2013 | Goddard et al. | |
| 8,933,046 B2 | 1/2015 | Machuy et al. | |
| 9,139,827 B2 | 9/2015 | Mirkin et al. | |
| 9,389,236 B2 | 7/2016 | Fandl et al. | |
| 9,506,056 B2 | 11/2016 | Mirkin et al. | |
| 9,532,948 B2 | 1/2017 | Mirkin et al. | |
| 9,617,541 B2 | 4/2017 | Mirkin et al. | |
| 9,844,562 B2 | 12/2017 | Mirkin et al. | |
| 9,889,209 B2 | 2/2018 | Mirkin et al. | |
| 10,098,958 B2 | 10/2018 | Mirkin et al. | |
| 10,182,988 B2 | 1/2019 | Mirkin et al. | |
| 10,208,310 B2 | 2/2019 | Mader et al. | |
| 10,370,656 B2 | 8/2019 | Mirkin et al. | |
| 10,391,116 B2 | 8/2019 | Mirkin et al. | |
| 10,398,784 B2 | 9/2019 | Mirkin et al. | |
| 10,434,064 B2 | 10/2019 | Radovic-Moreno et al. | |
| 10,653,780 B2 | 5/2020 | Hope et al. | |
| 10,704,043 B2 | 7/2020 | Daniel et al. | |
| 10,760,080 B2 | 9/2020 | Mader et al. | |
| 10,792,251 B2 | 10/2020 | Mirkin et al. | |
| 10,837,018 B2 | 11/2020 | Radovic-Moreno et al. | |
| 11,123,294 B2 | 9/2021 | Radovic-Moreno et al. | |
| 11,213,593 B2 | 1/2022 | Mirkin et al. | |
| 11,364,304 B2 | 6/2022 | Mirkin et al. | |
| 2002/0039568 A1 | 4/2002 | Moore et al. | |
| 2002/0172711 A1 | 11/2002 | Martin et al. | |
| 2003/0036568 A1* | 2/2003 | Raoof | A61K 31/7088 |
| | | | 514/772 |
| 2003/0147966 A1 | 8/2003 | Franzen et al. | |
| 2003/0170162 A1 | 9/2003 | Nayfeh et al. | |
| 2004/0023335 A1 | 2/2004 | Jing et al. | |
| 2004/0023382 A1* | 2/2004 | Dean | C07H 21/04 |
| | | | 435/375 |
| 2004/0053384 A1 | 3/2004 | Sligar et al. | |
| 2004/0158051 A1 | 8/2004 | Ozkan et al. | |
| 2004/0170560 A1 | 9/2004 | Fossheim et al. | |
| 2004/0171109 A1 | 9/2004 | Haudenschild et al. | |
| 2004/0234500 A1 | 11/2004 | Moore et al. | |
| 2005/0130911 A1 | 6/2005 | Uhlmann et al. | |
| 2005/0208572 A1 | 9/2005 | Shaughnessy | |
| 2006/0014191 A1 | 1/2006 | Lao et al. | |
| 2006/0073572 A1 | 4/2006 | Huang et al. | |
| 2006/0083713 A1 | 4/2006 | Glasebrook et al. | |
| 2006/0083781 A1 | 4/2006 | Shastri et al. | |
| 2006/0100151 A1 | 5/2006 | Troutt | |
| 2006/0292174 A1 | 12/2006 | De Los Rios et al. | |
| 2007/0065868 A1 | 3/2007 | Jing | |
| 2007/0280936 A1 | 12/2007 | Moore et al. | |
| 2008/0194463 A1 | 8/2008 | Weller et al. | |
| 2008/0213177 A1 | 9/2008 | Rademacher et al. | |
| 2008/0274454 A1 | 11/2008 | Mirkin et al. | |
| 2008/0306016 A1 | 12/2008 | Mirkin et al. | |
| 2008/0311182 A1 | 12/2008 | Ferrari et al. | |
| 2009/0018028 A1 | 1/2009 | Lindsay et al. | |
| 2009/0053169 A1 | 2/2009 | Castillo et al. | |
| 2009/0068737 A1 | 3/2009 | Yao et al. | |
| 2009/0075884 A1 | 3/2009 | Jacobs et al. | |
| 2009/0209629 A1 | 8/2009 | Mirkin et al. | |
| 2009/0275735 A1 | 11/2009 | Golstein et al. | |
| 2009/0299045 A1 | 12/2009 | Richards et al. | |
| 2009/0317802 A1 | 12/2009 | Bhatia et al. | |
| 2009/0322327 A1 | 12/2009 | Gao | |
| 2009/0324706 A1 | 12/2009 | Mirkin et al. | |
| 2010/0136682 A1 | 6/2010 | Mirkin et al. | |
| 2010/0143246 A1 | 6/2010 | Shi et al. | |
| 2010/0184844 A1 | 7/2010 | Mirkin et al. | |
| 2010/0233270 A1 | 9/2010 | Mirkin et al. | |
| 2010/0278840 A1 | 11/2010 | Mohler | |
| 2011/0052697 A1 | 3/2011 | Farokhzad et al. | |
| 2011/0111974 A1 | 5/2011 | Mirkin et al. | |
| 2011/0305734 A1 | 12/2011 | Edelson et al. | |
| 2012/0082616 A1* | 4/2012 | Trawick | A61P 35/00 |
| | | | 424/9.4 |
| 2012/0149843 A1 | 6/2012 | Chien et al. | |
| 2012/0244230 A1 | 9/2012 | Mirkin et al. | |
| 2013/0004520 A1 | 1/2013 | Andersson et al. | |
| 2013/0034599 A1 | 2/2013 | Thaxton et al. | |
| 2013/0089614 A1 | 4/2013 | Zhang et al. | |
| 2013/0101512 A1 | 4/2013 | Mirkin et al. | |
| 2013/0123333 A1 | 5/2013 | Mirkin et al. | |
| 2013/0149374 A1 | 6/2013 | Lee et al. | |
| 2013/0172404 A1 | 7/2013 | Mirkin et al. | |
| 2013/0178610 A1 | 7/2013 | Mirkin et al. | |
| 2013/0315831 A1 | 11/2013 | Shi et al. | |
| 2014/0005258 A1 | 1/2014 | Mirkin et al. | |
| 2014/0037635 A1 | 2/2014 | Medlock et al. | |
| 2014/0065425 A1 | 3/2014 | Bogdanov | |
| 2014/0179767 A1 | 6/2014 | Rozet et al. | |
| 2014/0294927 A1 | 10/2014 | Thaxton et al. | |
| 2015/0031745 A1 | 1/2015 | Mirkin et al. | |
| 2015/0080320 A1 | 3/2015 | Desai | |
| 2015/0086985 A1 | 3/2015 | Giljohann et al. | |
| 2015/0352138 A1 | 12/2015 | Mirkin et al. | |
| 2016/0053260 A1 | 2/2016 | Mirkin et al. | |
| 2016/0123964 A1 | 5/2016 | Tumeh et al. | |
| 2016/0186178 A1 | 6/2016 | Radovic-Moreno et al. | |
| 2016/0194642 A1 | 7/2016 | Gryaznov et al. | |
| 2016/0310425 A1 | 10/2016 | Mirkin et al. | |
| 2017/0044544 A1 | 2/2017 | Mirkin et al. | |
| 2017/0137809 A1 | 5/2017 | Mirkin et al. | |
| 2017/0157048 A1 | 6/2017 | Radovic-Moreno et al. | |
| 2017/0175121 A1 | 6/2017 | Gryaznov | |
| 2017/0232109 A1 | 8/2017 | Mirkin et al. | |
| 2017/0240960 A1 | 8/2017 | Giljohann et al. | |
| 2017/0306331 A1 | 10/2017 | Mader et al. | |
| 2018/0042848 A1 | 2/2018 | Gryaznov et al. | |
| 2018/0085390 A1 | 3/2018 | Mirkin et al. | |
| 2018/0193484 A1 | 7/2018 | Mirkin et al. | |
| 2018/0214376 A1 | 8/2018 | Giljohann | |
| 2018/0311176 A1 | 11/2018 | Ozsolak et al. | |
| 2018/0320184 A1 | 11/2018 | Radovic-Moreno et al. | |
| 2018/0327741 A1 | 11/2018 | Daniel et al. | |
| 2018/0344873 A1 | 12/2018 | Mirkin et al. | |
| 2019/0030185 A1 | 1/2019 | Mirkin et al. | |
| 2019/0142739 A1 | 5/2019 | Patel et al. | |
| 2019/0211338 A1 | 7/2019 | Mader et al. | |
| 2019/0225968 A1 | 7/2019 | Anderson et al. | |
| 2019/0275166 A1 | 9/2019 | Mirkin et al. | |
| 2020/0022913 A1 | 1/2020 | Mirkin et al. | |
| 2020/0069587 A1 | 3/2020 | Radovic-Moreno et al. | |
| 2020/0101156 A1 | 4/2020 | Mirkin et al. | |
| 2020/0188521 A1 | 6/2020 | Kang et al. | |
| 2020/0248183 A1 | 8/2020 | Nallagatla et al. | |
| 2020/0255837 A9 | 8/2020 | Anderson et al. | |

(56) References Cited

U.S. PATENT DOCUMENTS

| | | | |
|---|---|---|---|
| 2020/0291394 A1 | 9/2020 | Mirkin et al. |
| 2020/0297867 A1 | 9/2020 | Kang et al. |
| 2020/0339989 A1 | 10/2020 | Daniel et al. |
| 2020/0339996 A1 | 10/2020 | Mader et al. |
| 2020/0384104 A1 | 12/2020 | Mirkin et al. |
| 2021/0002640 A1 | 1/2021 | Kang et al. |
| 2021/0052497 A1 | 2/2021 | Mirkin et al. |
| 2021/0102211 A1 | 4/2021 | Radovic-Moreno et al. |
| 2021/0269806 A1 | 9/2021 | Anderson |
| 2022/0064649 A1 | 3/2022 | Anderson et al. |
| 2022/0088059 A1 | 3/2022 | Patel et al. |
| 2022/0348917 A1 | 11/2022 | Sarett |

FOREIGN PATENT DOCUMENTS

| | | | |
|---|---|---|---|
| CN | 1357042 A | 7/2002 |
| CN | 101218254 A | 7/2008 |
| CN | 101824088 A | 9/2010 |
| CN | 102036652 A | 4/2011 |
| CN | 102165061 A | 8/2011 |
| CN | 102197051 A | 9/2011 |
| EP | 1 251 872 A1 | 10/2002 |
| EP | 1 255 837 A2 | 11/2002 |
| EP | 1 266 002 A2 | 12/2002 |
| EP | 1 326 974 B1 | 12/2006 |
| EP | 1 899 911 A2 | 2/2008 |
| EP | 0 959 897 B1 | 4/2009 |
| EP | 0 817 847 B2 | 9/2009 |
| EP | 1 015 488 B1 | 9/2009 |
| EP | 2162117 A2 | 3/2010 |
| EP | 2 366 406 A1 | 9/2011 |
| EP | 1807094 B1 | 1/2012 |
| EP | 2451974 A2 | 5/2012 |
| EP | 2656858 A1 | 10/2013 |
| EP | 1 294 765 B1 | 11/2013 |
| EP | 3 112 468 A1 | 1/2017 |
| WO | WO 1992/021330 | 12/1992 |
| WO | WO 1993/021528 A1 | 10/1993 |
| WO | WO 1996/029408 A1 | 9/1996 |
| WO | WO 1998/04740 A1 | 2/1998 |
| WO | WO 1998/023284 A1 | 6/1998 |
| WO | WO-9927086 A1 * | 6/1999 | ......... C12N 15/1136 |
| WO | WO 1999/035267 A1 | 7/1999 |
| WO | WO 2000/013024 A1 | 3/2000 |
| WO | WO 2000/015759 A1 | 3/2000 |
| WO | WO 2000/020593 A1 | 4/2000 |
| WO | WO 2000/020645 | 4/2000 |
| WO | WO 2000/029567 A1 | 5/2000 |
| WO | WO 2000/042188 A2 | 7/2000 |
| WO | WO 2000/055204 A1 | 9/2000 |
| WO | WO 2000/069463 A1 | 11/2000 |
| WO | WO 2001/000876 A1 | 1/2001 |
| WO | WO 2001/022990 A2 | 4/2001 |
| WO | WO 2001/057202 A2 | 8/2001 |
| WO | WO 2001/059120 A2 | 8/2001 |
| WO | WO 2001/064240 A2 | 9/2001 |
| WO | WO 2001/068859 A2 | 9/2001 |
| WO | WO 2002/058717 A2 | 8/2002 |
| WO | WO 2003/008539 A2 | 1/2003 |
| WO | WO 2002/038764 A3 | 7/2003 |
| WO | WO 2003/055980 A2 | 7/2003 |
| WO | WO 2002/102411 A3 | 9/2003 |
| WO | WO 2002/064739 A3 | 6/2004 |
| WO | WO 2005/030259 A2 | 4/2005 |
| WO | WO 2005/063201 A2 | 7/2005 |
| WO | WO 2005/063288 A1 | 7/2005 |
| WO | WO 2005/108616 A1 | 11/2005 |
| WO | WO 2005/116226 A2 | 12/2005 |
| WO | WO 2006/015560 A1 | 2/2006 |
| WO | WO 2006/088833 A2 | 8/2006 |
| WO | WO 2006/110350 A2 | 10/2006 |
| WO | WO 2006/138145 A1 | 12/2006 |
| WO | WO 2007/047455 A2 | 4/2007 |
| WO | WO 2007/055682 A2 | 5/2007 |
| WO | WO 2007/055704 A2 | 5/2007 |
| WO | WO 2007/060406 A1 | 5/2007 |
| WO | WO 2007/064857 A2 | 6/2007 |
| WO | WO 2007/089607 A2 | 8/2007 |
| WO | WO 2007/106683 A2 | 9/2007 |
| WO | WO 2007/122405 A1 | 11/2007 |
| WO | WO 2008/42156 A1 | 4/2008 |
| WO | WO 2008/097328 A2 | 8/2008 |
| WO | WO 2008/127789 A2 | 10/2008 |
| WO | WO 2008/137762 A2 | 11/2008 |
| WO | WO 2008/141289 A1 | 11/2008 |
| WO | WO 2009/012786 A2 | 1/2009 |
| WO | WO 2009/026412 A1 | 2/2009 |
| WO | WO 2009/051451 A2 | 4/2009 |
| WO | WO 2009/061515 A1 | 5/2009 |
| WO | WO 2009/073984 A1 | 6/2009 |
| WO | WO 2009/105260 | 8/2009 |
| WO | WO 2009/120887 A2 | 10/2009 |
| WO | WO 2009/131704 | 10/2009 |
| WO | WO 2010/017152 | 2/2010 |
| WO | WO 2010/017154 | 2/2010 |
| WO | WO 2010/081049 A2 | 7/2010 |
| WO | WO 2010/085959 A1 | 8/2010 |
| WO | WO 2010/091293 A1 | 8/2010 |
| WO | WO 2010/120420 | 10/2010 |
| WO | WO 2010/148249 A1 | 12/2010 |
| WO | WO 2011/017456 A2 | 2/2011 |
| WO | WO 2011/017690 A2 | 2/2011 |
| WO | WO 2011/053940 A2 | 5/2011 |
| WO | WO 2011/072133 A1 | 6/2011 |
| WO | WO 2011/078672 A1 | 6/2011 |
| WO | WO 2011/079290 A1 | 6/2011 |
| WO | WO 2011/079290 A2 | 6/2011 |
| WO | WO 2011/091065 A2 | 7/2011 |
| WO | WO 2011/113054 A2 | 9/2011 |
| WO | WO 2011/143608 A1 | 11/2011 |
| WO | WO 2012/055933 A1 | 5/2012 |
| WO | WO 2013/011368 A2 | 1/2013 |
| WO | WO 2013/012628 A2 | 1/2013 |
| WO | WO 2013/086207 A1 | 6/2013 |
| WO | WO 2014/025795 A1 | 2/2014 |
| WO | WO 2014/123935 A1 | 8/2014 |
| WO | WO 2014/169264 A2 | 10/2014 |
| WO | WO 2015/013675 A1 | 1/2015 |
| WO | WO 2015/153975 A1 | 10/2015 |
| WO | WO 2015/187966 A1 | 12/2015 |
| WO | WO 2015/195628 A2 | 12/2015 |
| WO | WO 2016/057549 A1 | 4/2016 |
| WO | WO 2016/115320 A1 | 7/2016 |
| WO | WO 2016/149323 A2 | 9/2016 |
| WO | WO 2017/011662 A1 | 1/2017 |
| WO | WO 2017/035278 A1 | 3/2017 |
| WO | WO 2017/161032 A1 | 9/2017 |
| WO | WO 2017/193081 A1 | 11/2017 |
| WO | WO 2018/152327 A2 | 8/2018 |
| WO | WO 2018/209270 A1 | 11/2018 |
| WO | WO 2019/118883 A2 | 6/2019 |
| WO | WO 2019/168558 A1 | 9/2019 |
| WO | WO 2020/168005 A1 | 8/2020 |
| WO | WO 2021/202557 A1 | 10/2021 |
| WO | WO 2022/032182 A1 | 2/2022 |
| WO | WO 2022/036013 A1 | 2/2022 |
| WO | WO 2022/147541 A1 | 7/2022 |
| WO | WO 2022/150369 A1 | 7/2022 |

OTHER PUBLICATIONS

Extended European Search Report dated Mar. 27, 2020 in connection with EP 17793513.7.

Agbasi-Porter et al., Transcription inhibition using oligonucleotide-modified gold nanoparticles, Bioconjugate Chem., 17(5):1178-83 (2006).

Bonoiu et al., Nanotechnology approach for drug addiction therapy: gene ; silencing using delivery of gold nanorod-siRNA nanoplex in dopaminergic neurons. Proc Natl Acad Sci U S A. Apr. 7, 2009;106(14):5546-50. doi:; 10.1073/pnas.0901715106. Epub Mar. 23, 2009.

Chabaud et al., Enhancing effect of IL-17 on IL-1-induced IL-6 and leukemia inhibitory factor production by rheumatoid arthritis

(56) References Cited

OTHER PUBLICATIONS synoviocytes and its regulation by Th2 cytokines. J Immunol. Jul. 1, 1998;161(1):409-14.
Cload et al., Polyether tethered oligonucleotide probes. J. Am. Chem. Soc. 1991;113(16): 6324-6.
Cormode, D.P. et al., "Nanocrystal Core High-Density Lipoproteins: A Multimodality Contrast Agent Platform," Nano Lett., 2008, 8 (11), 3715-3723.
DeMesmaeker et al., Antisense oligonucleotides. Acc. Chem. Res. 1995;28(9): 366-74.
Ding et al., A Crosslinked Nucleic Acid Nanogel for Effective siRNA Delivery and Antitumor Therapy. Angew Chem Int Ed Engl. Mar. 12, 2018;57(12):3064-3068. doi:10.1002/anie.201711242. Epub Feb. 22, 2018.
Ding et al., A statistical sampling algorithm for RNA secondary structure prediction. Nucleic Acids Res. Dec. 15, 2003;31(24):7280-301. doi: 10.1093/nar/gkg938.
Fattal et al., Biodegradable polyalkylcyanoacrylate nanoparticles for the delivery of oligonucleotides. J. Controlled Release. 1998;53:137-143.
Ghosh et al., Gold nanoparticles in delivery applications. Adv. Drug Deliv. Rev. 2008;60(11):1307-15.
Hames et al., Gene Probes 1 A Practical Approach, IRL Press, New York (1995).
Hayashi, Ultrafine particles. J. Vac. Sci. Technol. 1987;5(4):1375-1384.
Hellstrom et al., Epitaxial growth of DNA-assembled nanoparticle superlattices on patterned substrates. Nano Lett. 2013;13(12):6084-90. doi: 10.1021/nl4033654. Epub Nov. 20, 2013.
Jen et al., A nonviral transfection approach in vitro: the design of a gold nanoparticle vector joint with microelectromechanical systems. Langmuir, 2004;20(4): 1369-74.
Jensen et al., Spherical nucleic acid nanoparticle conjugates as an RNAi-based therapy for glioblastoma, Sci. Trans. Med., 5:209ra152 (2013).
Jin et al., What controls the melting properties of DNA-linked gold nanoparticle assemblies? J. Am. Chem. Soc. 2003;125: 1643.
Kolarova et al., Preparation of magnetic oligo (dT) particles. Biotechniques. 1996;20: 196-8.
Lee et al., A DNA-Gold Nanoparticle-Based Colormetric Competition Assay for the Detection of Cysteine. Nano Letter. 2008;8(2):529-533.
Lee et al., Chip-based scanometric detection of mercuric ion using DNA-functionalized gold nanoparticles. Anal. Chem. 2008;80(17):6805-8.
Li et al., "Molecular spherical nucleic acids," PNAS pp. 1-5 (2018).
Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.
Li et al., Targeted delivery of antisense oligodeoxynucleotide and small interference RNA into lung cancer cells. Mol Pharm. Sep.-Oct. 2006;3(5):579-88. doi: 10.1021/mp060039w. Publication Date:Jul. 12, 2006.
Li et al., Reversible and Chemically Programmable Micelle Assembly with DNA Block-Copolymer Amphiphiles, Nano Lett. 2004;4:1055.
Liu et al., "New poly(d-glucaramidoamine)s induce DNA nanoparticle formation and efficient gene delivery into mammalian cells," J. Am. Chem. Soc. 126:7422-7423 (2004).
Liu et al., DNA-based micelles: synthesis, micellar properties and size-dependent cell permeability, Chemistry. 2010;16:3791-7.
Ljubimova et al., Nanoconjugate based on polymalic acid for tumor targeting. Chem Biol Interact. Jan. 30, 2008;171(2):195-203. Epub Feb. 8, 2007.
Marinakos et al., Template Synthesis of One-Dimensional Au, Au-Poly(pyrrole), and Poly(pyrrole) Nanoparticle Arrays. Chem. Mater. 1998;10:1214-19.
Matijevic et al., Fine Particles Part II: Formation Mechanisms and Applications. MRS Bulletin pp. 16-47 (1990).
Maye et al., A simple method for kinetic control of DNA-induced nanoparticle assembly. J. Am. Chem. Soc. 2006; 128: 14020-1.
Miller et al., Antisense oligonucleotides: Strategies for delivery. PSTT. 1998;1(9): 377-86.
Ming et al., Albumin-based nanoconjugates for targeted delivery of; therapeutic oligonucleotides. Biomaterials. Oct. 2013;34(32):7939-49. doi:; 10.1016/j.biomaterials.2013.06.066. Epub Jul. 19, 2013.
Miossec, Interleukin-17 in rheumatoid arthritis: if T cells were to contribute to inflammation and destruction through synergy. Arthritis Rheum. Mar. 2003;48(3):594-601. doi: 10.1002/art.10816. PMID: 12632409.
Moughton et al., Hollow nanostructures from self-assembled supramolecular metallo-triblock copolymers. Soft Matter. 2009;5(12):2361-70.
Mucic et al., Synthesis and characterization of DNA with ferrocenyl groups attached to their 5'-termini: electrochemical characterization of a redox-active nucleotide monolayer. Chem. Comm. 1996;555-7.
Nuzzo et al., Spontaneously organized molecular assemblies. 3. Preparation and properties of solution adsorbed monolayers of organic disulfides on gold surfaces. J. Am. Chem. Soc. 1987;109:2358-68.
Park et al., DNA-programmable nanoparticle cystrallization. Nature. 2008;451: 553-6.
Patel et al., Scavenger receptors mediate cellular uptake of polyvalent oligonucleotide-functionalized gold nanoparticles, Bioconj. Chem., 21:2250 (2010).
Patil et al., DNA-based therapeutics and DNA delivery systems: a comprehensive review. AAPS J., 2005;7(1): E61-77.
Shukla et al., Development of streptavidin-based ; nanocomplex for siRNA delivery. Mol Pharm. Dec. 2, 2013;10(12):4534-45. doi:; 10.1021/mp400355q. Epub Oct. 25, 2013.
Storhoff et al., Sequence-Dependent Stability of DNA-Modified Gold Nanoparticles. Langmuir. 2002;18: 6666-6670.
Taton et al., Scanometric DNA array detection with nanoparticle probes. Science, 2000;289(5485):1757-60.
Thomas, "The Interaction of HgCl2 with Sodium Thymonucleate," J. Am. Chem. Soc., 76:6032-6034 (1954).
Tondelli et al., "Highly efficient cellular uptake of c-myb antisense oligonucleotides through specifically desianed polymeric nanospheres," Nucl. Acids Res. 26:5425-5431 (1998).
Wagner et al., Gene inhibition using antisense oligodeoxynucleotides. Nature, 1994;372: 333-5.
Xu et al., A gold-nanoparticle-based real-time colorimetric screening method for endonuclease activity and inhibition. Angew. Chem. Int. Ed. Engl., 2007;46(19):3468-70.
Xu et al., Homogeneous detection of nucleic acids based upon the light scattering properties of silver-coated nanoparticle probes. Anal. Chem., 2007;79(17):6650-4.
Xu et al., Thermodynamics of DNA hybridization on gold nanoparticles. J. Am. Chem. Soc., 2005;127(38): 13227-31.
Yamane et al., On the complexing of desoxyribonucleic acid (DNA) by mercuric ion. J. Am. Chem. Soc., 1961;83:2599-2607.
Yao et al. Herpesvirus Saimiri encodes a new cytokine, IL-17, which binds to a novel cytokine receptor. Immunity. Dec. 1995;3(6):811-21.
Zhang et al., "A general strategy for the DNA-mediated self-assembly of functional nanoparticles into heterogeneous systems," Nat Nanotechnol 8(11): 865-872 (2013).
Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.
Akhter et al., Gold nanoparticles in theranostic oncology: current state-of-the-art. Expert Opin Drug Deliv. Oct. 2012;9(10):1225-43. Epub Aug. 16, 2012.
Ali et al., Vaccines Combined with Immune Checkpoint Antibodies Promote Cytotoxic T-cell Activity and Tumor Eradication. Cancer Immunol Res. Feb. 2016;4(2):95-100. doi: 10.1158/2326-6066.CIR-14-0126. Epub Dec. 15, 2015.

(56) References Cited

OTHER PUBLICATIONS

Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Aurasense Therapeutics, NIH grant, Topically-delivered Target Gene Suppression of Immune Activation in Psoriasis—David Giljohann, Accessed on Aug. 2, 2017 from http://grantome.com/grant/NIH/R41-AR066438-01. Accessible online on Feb. 21, 2016 as verified through Wayback Machine.
Banchelli, M. et al., Phospholipid Membranes Decorated by Cholesterol-Based Oligonucleotides as Soft Hybrid Nanostructures, J. Phys. Chem., 2008, 112 (35), 10942-10952.
Banga et al., Liposomal spherical nucleic acids. J Am Chem Soc. Jul. 16, 2014;136(28):9866-9. doi: 10.1021/ja504845f. Epub Jul. 1, 2014.
Bhattarai et al., Enhanced Gene and siRNA Delivery by Polycation-Modified Mesoporous Silica Nanoparticles Loaded with Chloroquine, Pharm. Res., 2010, 27, 2556-2568.
Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.
Cheng et al., Interdigitated phospholipid/alkanethiol bilayers assembled on APTMS-supported gold colloid electrodes. Electroanalysis. 2004;16(1-2):127-31. doi:10.1002/elan.200302929.
Cheng et al., Tandem synthesis of core-shell brush copolymers and their transformation to peripherally cross-linked and hollowed nanostructures. J Am Chem Soc. May 31, 2006;128(21):6808-9. Published on web May 6, 2006.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Cho et al., Therapeutic nanoparticles for drug delivery in cancer. Clin Cancer Res. Mar. 1, 2008;14(5):1310-6. doi: 10.1158/1078-0432.CCR-07-1441.
Cutler et al., Polyvalent nucleic acid nanostructures. J Am Chem Soc. Jun. 22, 2011;133(24):9254-7. doi: 10.1021/ja203375n. Epub Jun. 1, 2011.
Cutler et al., Polyvalent oligonucleotide iron oxide nanoparticle click conjugates. Nano Lett. Apr. 14, 2010;10(4):1477-80. doi:10.1021/nl100477m.
Cutler et al., Spherical nucleic acids. J Am Chem Soc. Jan. 25, 2012;134(3):1376-91. doi: 10.1021/ja209351u. Epub Jan. 9, 2012.
Daniel et al., Gold nanoparticles: assembly, supramolecular chemistry, quantum-size-related properties, and applications toward biology, catalysis, and nanotechnology. Chem Rev. Jan. 2004;104(1):293-346.
Dave et al., Programmable assembly of DNA-functionalized liposomes by DNA. ACS Nano. Feb. 22, 2011;5(2):1304-12. doi: 10.1021/nn1030093. Epub Jan. 4, 2011.
Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.
Elbakry, A. et al., Layer-by-Layer Assembled Gold Nanoparticles for siRNA Delivery, Nano Lett., 2009, 9 (5), 2059-2064.
Fan, H. et al., Self-Assembly of Ordered, Robust, Three-Dimensional Gold Nanocrystal/Silica Arrays, Science, 2004, 403, 567-571.
Giljohann et al., Gene regulation with polyvalent siRNA-nanoparticle conjugates. J Am Chem Soc. Feb. 18, 2009;131(6):2072-3.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.

Gissot et al., Nucleoside, nucleotide and oligonucleotide based amphiphiles: a successful marriage of nucleic acids with lipids. Org. Biomol. Chem. 2008;6:1324-33.
Godard, G. et al., Antisense Effects of Cholesterol-Oligodeoxynucleotide Conjugates Associated with Poly(alkylcyanoacrylate) Nanoparticles, Eur. J. Biochem., 1995, 232 (2), 404-410.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gryaznov, Oligonucleotide n3'→p5' phosphoramidates and thiophoshoramidates as potential therapeutic agents. Chem Biodivers. Mar. 2010;7(3):477-93. doi: 10.1002/cbdv.200900187. Review.
Han et al., Drug and gene delivery using gold nanoparticles. NanoBiotechnology. Mar. 2007;3(1):40-5.
Hashmi et al., Gold catalysis. Angew Chem Int Ed Engl. Dec. 4, 2006;45(47):7896-936.
Hashmi, Gold-catalyzed organic reactions. Chem Rev. Jul. 2007;107(7):3180-211. Epub Jun. 20, 2007.
He et al., Phospholipid-stabilized Au-nanoparticles. Biomacromolecules. May-Jun. 2005;6(3):1224-5.
Hurst, S. et al., Maximizing DNA Loading on a Range of Gold Nanoparticle Sizes, Anal. Chem., 2006, 78 (24), 8313-8318.
Khmelinskaia et al., Effect of anchor positioning on binding and diffusion of elongated 3D DNA nanostructures on lipid membranes. J. Phys. D: Appl. Phys. Apr. 13, 2016;49(19):194001.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kim, S. et al., Systemic and Specific Delivery of Small Interfering RNAs to the Liver Mediated by Apolipoprotein A-I, Mol. Ther., 2007, 15 (6), 1145-1152.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Kwoh et al., Stabilization of poly-L-lysine/DNA polyplexes for in vivo gene delivery to the liver. Biochim Biophys Acta. Feb. 16, 1999;1444(2):171-90.
Leander, D., Mixed-Monolayer Gold Nanoparticles for Cancer Therapeutics, Nanoscape, 2010, 7 (1), 11-14.
Lee et al., All-in-one target-cell-specific magnetic nanoparticles for simultaneous molecular imaging and siRNA delivery. Angew Chem Int Ed Engl. 2009;48(23):4174-9. doi: 10.1002/anie.200805998.
Lee et al., Imageable antigen-presenting gold nanoparticle vaccines for effective cancer immunotherapy in vivo. Angew Chem Int Ed Engl. Aug. 27, 2012;51(35):8800-5. doi: 10.1002/anie.201203193.
Lenert et al., Inhibitory oligonucleotides block the induction of AP-1 transcription factor by stimulatory CpG oligonucleotides in B cells. Antisense Nucleic Acid Drug Dev. 2003;13(3):143-50.
Lennox et al., Characterization of modified antisense oligonucleotides in Xenopus laevis embryos. Oligonucleotides. 2006 Spring;16(1):26-42.
Lewandowski et al., Topically delivered spherical nucleic acid nanoconjugates targeting TNF improve the psoriatic phenotype. J Invest Dermatol. 2015 135:S71. Abstract 413.
Li et al., Nanofabrication by DNA self-assembly. Materials Today. Elsevier Science. May 1, 2009;12(5)24-32.
Liu et al., Structure-based programming of lymph-node targeting in molecular vaccines. Nature. Mar. 27, 2014;507(7493):519-22. doi: 10.1038/nature12978.
Liu, J. et al., Silica Nanoparticle Supported Lipid Bilayers for Gene Delivery, Chem. Commun., 2009, 5100-5102.
Luo et al., Locally instilled tumor necrosis factor α antisense oligonucleotide contributes to inhibition of TH 2-driven pulmonary fibrosis via induced CD4+ CD25+ Foxp3+ regulatory T cells. J Gene Med. Nov.-Dec. 2013;15(11-12):441-52. doi: 10.1002/jgm.2750.
Lytton-Jean et al., A thermodynamic investigation into the binding properties of DNA functionalized gold nanoparticle probes and molecular fluorophore probes. J Am Chem Soc. Sep. 21, 2005;127(37):12754-5.

(56) References Cited

OTHER PUBLICATIONS

Major, M. et al., Characterisation and Phase Behaviour of Phospholipid Bilayers Adsorbed on Spherical Polysaccharidic Nanoparticles, Biochimica et Biophysica Acta, 1997, 1327, 32-40.
Massich et al., Regulating immune response using polyvalent nucleic acid-gold nanoparticle conjugates. Mol Pharm. Nov.-Dec. 2009;6(6):1934-40.
Matsunaga, T. et al., Biomagnetic Nanoparticle Formation and Application, Supramolecular Science, 1998, 5 (3-4), 391-394.
McBain, S. et al., Polyethyleneimine Functionalized Iron Oxide Nanoparticles as Agents for DNA Deliver and Transfection, J. Mater. Chem., 2007, 17, 2561-2565.
McKay et al., Characterization of a potent and specific class of antisense oligonucleotide inhibitor of human protein kinase C-alpha expression. J Biol Chem. Jan. 15, 1999;274(3):1715-22.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
Medintz et al., A reactive peptidic linker for self-assembling hybrid quantum dot-DNA bioconjugates. Nano Lett. Jun. 2007;7(6):1741-8. Epub May 26, 2007.
Mohamed et al., Effect of toll-like receptor 7 and 9 targeted therapy to prevent the development of hepatocellular carcinoma. Liver Int. Mar. 2015;35(3):1063-76. doi: 10.1111/liv.12626. Epub Jul. 30, 2014.
Monia et al., Nuclease resistance and antisense activity of modified oligonucleotides targeted to Ha-ras. J Biol Chem. Jun. 14, 1996;271(24):14533-40.
Nam et al., Nanoparticle-based bio-bar codes for the ultrasensitive detection of proteins. Science. Sep. 26, 2003;301(5641):1884-6.
Niemeyer, C. et al., Bifunctional DNA-Gold Nanoparticle Conjugates as Building Blocks for the Self-Assembly of Cross-Linked Particle Layers, Biochemical and Biophysical Research Communications, 2003, 311 (4), 995-999.
Nikolov et al., Bias-dependent admittance in hybrid bilayer membranes. Langmuir. Aug. 15, 2006;22(17):7156-8.
Pan et al., Dendrimer-Modified Magnetic Nanoparticles Enhance Efficiency of Gene Delivery System. Cancer Res. 2007;67:8156-8163.
Patel et al., Peptide antisense nanoparticles. Proc Natl Acad Sci U S A. Nov. 11, 2008;105(45):17222-6. doi: 10.1073/pnas.0801609105.
Patil et al., Evidence for Novel Interdigitated Bilayer Formation of Fatty Acids During Three-Dimensional Self-Assembly on Silver Colloidal Particles, J. Am. Chem. Soc., 1997, 119 (39), 9281-9282.
Patwa et al., Hybrid lipid oligonucleotide conjugates: synthesis, self-assemblies and biomedical applications. Chem Soc Rev. 2011;40:5844-54.
Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Plant et al., Self-assembled phospholipid/alkanethiol biomimetic bilayers on gold. Langmuir. 1993;9:2764-7.
Pokholenko et al., Lipid oligonucleotide conjugates as responsive nanomaterials for drug delivery. J of Materials Chemistry B. 2013;5329-34.
Ponnappa et al., Inhibition of tumor necrosis factor alpha secretion and prevention of liver injury in ethanol-fed rats by antisense oligonucleotides. Biochem Pharmacol. Feb. 15, 2005;69(4):569-77. Epub Dec. 30, 2004.
Qin et al., Significantly improved analytical sensitivity of lateral flow immunoassays by using thermal contrast. Angew Chem Int Ed Engl. Apr. 27, 2012;51(18):4358-61. doi:10.1002/anie.201200997. Epub Mar. 23, 2012.
Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Rojanasakul et al., Antisense inhibition of silica-induced tumor necrosis factor in alveolar macrophages. J Biol Chem. Feb. 14, 1997;272(7):3910-4.
Romanucci et al., Synthesis, biophysical characterization and anti-HIV activity of d(TG3AG) Quadruplexes bearing hydrophobic tails at the 5'-end. Bioorg Med Chem. Feb. 1, 2014;22(3):960-6. doi: 10.1016/j.bmc.2013.12.051. Epub Jan. 4, 2014.
Rosi et al., Oligonucleotide-modified gold nanoparticles for intracellular gene regulation. Science. May 19, 2006;312(5776):1027-30.
Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.
Seferos et al., Polyvalent DNA nanoparticle conjugates stabilize nucleic acids. Nano Lett. Jan. 2009;9(1):308-11.
Shahzad et al., Targeted delivery of small interfering RNA using reconstituted high-density lipoprotein nanoparticles. Neoplasia. Apr. 2011;13(4):309-19.
Sita et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. doi: 10.1073/pnas.1702736114. Epub Apr. 3, 2017.
Stunz et al., Inhibitory oligonucleotides specifically block effects of stimulatory CpG oligonucleotides in B cells. Eur J Immunol. May 2002;32(5):1212-22.
Tang et al., Probing hydroxyl radicals and their imaging in living cells by use of FAM-DNA-Au nanoparticles. Chemistry. Jan. 7, 2008;14(2):522-8.
Thompson et al., Smart lipids for programmable nanomaterials. Nano Lett. Jul. 14, 2010;10(7):2690-3. doi: 10.1021/nl101640k.
Tiwari et al., Functionalized gold nanoparticles and their biomedical applications. Nanomaterials. 2011;1:31-63. doi: 10.3390/nano1010031.
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
United States Securities and Exchange Commission Form 8-K Current Report, Date of Report (Date of earliest event reported): Sep. 26, 2017, Exicure, Inc. Dated: Oct. 2, 2017 by David Giljohann Accessed from the internet (Oct. 11, 2018) at https://www.sec.gov/Archives/edgar/data/1698530/000119312517301064/d461080d8k.htm.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Wilton et al. Antisense oligonucleotide-induced exon skipping across the human dystrophin gene transcript. Mol Ther. Jul. 2007;15(7):1288-96. Epub Feb. 6, 2007.
Wolfrum et al., Mechanisms and optimization of in vivo delivery of lipophilic siRNAs. Nat Biotechnol. Oct. 2007;25(10):1149-57. Epub Sep. 16, 2007.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Xiao et al., Mannosylated bioreducible nanoparticle-mediated macrophage-specific TNF-α RNA interference for IBD therapy. Biomaterials. Oct. 2013;34(30):7471-82. doi: 10.1016/j.biomaterials.2013.06.008. Epub Jun. 29, 2013.

(56) References Cited

OTHER PUBLICATIONS

Yang et al., Inhibition of a C-rich oligodeoxynucleotide on activation of immune cells in vitro and enhancement of antibody response in mice. Immunology. Dec. 2010; 131(4):501-12. doi: 10.1111/j.1365-2567.2010.03322.x.

Yin et al., Supramolecular self-assembled nanoparticles mediate oral delivery of therapeutic TNF-α siRNA against systemic inflammation. Angew Chem Int Ed Engl. May 27, 2013;52(22):5757-61. doi: 10.1002/anie.201209991. Epub Apr. 22, 2013.

Zhang et al., A general approach to DNA-programmable atom equivalents. Nat Mater. Aug. 2013;12(8):741-6. doi: 10.1038/nmat3647. Epub May 19, 2013.

Zhang et al., Informational liposomes: Complexes derived from cholesteryl-conjugated oligonucleotides and liposomes. Tetrahedron Letters. 1996. 37(35):6243-6.

Zhang et al., Nanopod formation through gold nanoparticle templated and catalyzed cross-linking of polymers bearing pendant propargyl ethers. J Am Chem Soc. Nov. 3, 2010;132(43):15151-3.

Zhang et al., Self-assembled monolayers of terminal alkynes on gold. J Am Chem Soc. Apr. 25, 2007;129(16):4876-7. Epub Mar. 31, 2007.

Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.

PCT/US2017/031428, Nov. 15, 2018, International Preliminary Report on Patentability.

EP 17793513.7, Nov. 22, 2019, Partial Supplementary European Search Report mailed.

EP 17793513.7, Mar. 27, 2020, Extended European Search Report.

Cottrez et al., Genes specifically modulated in sensitized skins allow the detection of sensitizers in a reconstructed human skin model. Development of the SENS-IS assay. Toxicol In Vitro. Jun. 2015;29(4):787-802. doi: 10.1016/j.tiv.2015.02.012. Epub Feb. 24, 2015.

Huang et al., Sequence Multiplicity within Spherical Nucleic Acids. ACS Nano. Jan. 28, 2020;14(1):1084-1092. doi: 10.1021/acsnano.9b08750. Epub Jan. 9, 2020.

Kapadia et al., Spherical Nucleic Acid Nanoparticles: Therapeutic Potential. BioDrugs. Aug. 2018;32(4):297-309. doi: 10.1007/s40259-018-0290-5. Author Manuscript. 24 pages.

Manoharan et al., Lipidic nucleic acids. Tetrahedron Letters. May 22, 1995;36(21):3651-4.

Nemati et al., Using siRNA-based spherical nucleic acid nanoparticle conjugates for gene regulation in psoriasis. J Control Release. Dec. 28, 2017;268:259-268. doi: 10.1016/j.jconrel.2017.10.034. Epub Oct. 23, 2017.

Periyasamy et al., Nanomaterials for the local and targeted delivery of osteoarthritis drugs. J Nanomater. 2012:2012:Article 673968. 13 pages. doi:0.1155/2012/673968.

Ward-Kavanagh et al., The TNF Receptor Superfamily in Co-stimulating and Co-inhibitory Responses. Immunity. May 17, 2016;44(5):1005-19. doi: 10.1016/j.immuni.2016.04.019.

Yao et al. Human IL-17: a novel cytokine derived from T cells. J Immunol. Dec. 15, 1995; 155(12):5483-6.

U.S. Appl. No. 15/301,467, filed Oct. 3, 2016, Gryaznov.

U.S. Appl. No. 16/099,404, filed Nov. 6, 2018, Anderson et al.

U.S. Appl. No. 16/099,385, filed Nov. 6, 2018, Kang et al.

U.S. Appl. No. 17/639,938, filed Mar. 3, 2022, Sarett.

Inoue, Oligonucleotide therapeutics: past, present and future. Drug Delivery System. Jan. 2016;31(1):10-23.

Karathanasis et al., Selective targeting of nanocarriers to neutrophils and monocytes. Ann Biomed Eng. Oct. 2009;37(10):1984-92. doi: 10.1007/s10439-009-9702-5. Epub Apr. 23, 2009.

Somiya et al., Potential of a non-cationic liposomes-based delivery system for nucleic acid medicines. Drug Delivery System. Jan. 2016;31(1):35-43.

Radovic-Moreno et al., Immunomodulatory spherical nucleic acids. Proc Natl Acad Sci U S A PNAS. Mar. 31, 2015;112(13):3892-7. doi: 10.1073/pnas.1502850112. Epub Mar. 16, 2015.

Skakuj et al., Conjugation Chemistry-Dependent T-Cell Activation with Spherical Nucleic Acids. J Am Chem Soc. Jan. 31, 2018;140(4):1227-1230 and Supplemental Information. doi: 10.1021/jacs.7b12579. Epub Jan. 22, 2018. 13 pages.

Somiya et al., Potential of a non-cationic lioposomes-based delivery system for nucleic acid medicines. Drug Delivery System. Jan. 2016;31(1):35-43.

Chan et al., Lipid-anchored DNA mediates vesicle fusion as observed by lipid and content mixing. Biointerphases. Jun. 2008;3(2):FA17. doi: 10.1116/1.2889062.

Ming et al., Bioconjugates for targeted delivery of therapeutic oligonucleotides. Adv Drug Deliv Rev. Jun. 29, 2015;87:81-9. doi: 10.1016/j.addr.2015.02.002. Epub Feb. 15, 2015.

Raouane et al., Lipid conjugated oligonucleotides: a useful strategy for delivery. Bioconjug Chem. Jun. 20, 2012;23(6):1091-104. doi: 10.1021/bc200422w. Epub Mar. 15, 2012.

U.S. Appl. No. 17/066,134, filed Oct. 8, 2020, Radovic-Moreno et al.

U.S. Appl. No. 16/095,134, filed Oct. 19, 2018, Patel et al.

U.S. Appl. No. 17/231,896, filed Nov. 6, 2018, Anderson et al.

U.S. Appl. No. 16/099,409, filed Nov. 6, 2018, Nallagatla et al.

U.S. Appl. No. 16/608,685, filed Oct. 25, 2019, Kang et al.

U.S. Appl. No. 17/253,102, filed Dec. 16, 2020, Anderson.

U.S. Appl. No. 17/430,277, filed Aug. 11, 2021, Bexon et al.

U.S. Appl. No. 16/976,168, filed Aug. 27, 2020, Kang et al.

U.S. Appl. No. 17/605,784, filed Oct. 22, 2021, Anderson.

U.S. Appl. No. 17/639,938, filed Mar. 3, 2022, Sarett et al.

U.S. Appl. No. 17/011,658, filed Sep. 3, 2020, Mirkin et al.

U.S. Appl. No. 18/019,857, filed Feb. 6, 2023, Anderson et al.

U.S. Appl. No. 18/020,501, filed Feb. 9, 2023, Anderson et al.

\* cited by examiner

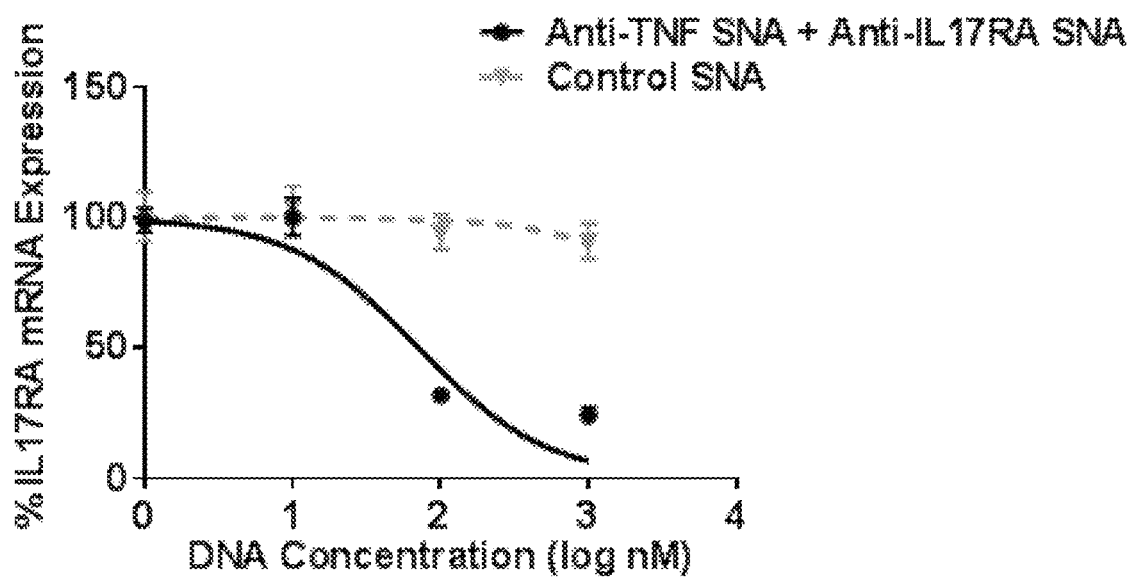

SEQUENCE LISTING

<160> NUMBER OF SEQ ID NOS: 311

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
gctgcacttt ggagtgatcg                                           20

<210> SEQ ID NO 2
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 2
gtttgctaca acatgggcta cag                                       23

<210> SEQ ID NO 3
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with 6-fluorescein amidite (FAM)
<220> FEATURE:
<221> NAME/KEY: misc_feature
<222> LOCATION: (26)..(26)
<223> OTHER INFORMATION: Modified with black hole quencher 1 (BHQ1)

<400> SEQUENCE: 3
cccaggcagt cagatcatct tctcga                                        26

<210> SEQ ID NO 4
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 4
caaggtcatc catgacaact ttg                                           23

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
gggccatcca cagtcttct                                                19

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with Hexachloro-Fluorescein (HEX)
<220> FEATURE:
<221> NAME/KEY: misc_feature
<222> LOCATION: (25)..(25)
<223> OTHER INFORMATION: Modified with black hole quencher 1 (BHQ1)

<400> SEQUENCE: 6
accacagtcc atgccatcac tgcca                                         25

<210> SEQ ID NO 7
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond

```
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 7
ucgcggaggg ctcggccc                                                 18

<210> SEQ ID NO 8
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with an O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with an O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 8
gucgcggagg gcucggcc                                                 18

<210> SEQ ID NO 9
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 9
cgucgcggag ggcucggc                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
```

-continued

<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 10
acggcgggct gcgugcgg                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 11
gacggcgggc tgcgugcg                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 12
acucugcacc ctcgaggu                                                 18

<210> SEQ ID NO 13
<211> LENGTH: 18
<212> TYPE: RNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 13
gggcugccca gcagcggg                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 14
ugugugggtc tgugagga                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 15
ggcgugtgtg ggucugug                                                 18
```

```
<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 16
gggcgugtgt gggucugu                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 17
agggcgtgtg tgggucug                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

-continued

```
<400> SEQUENCE: 18
uagggcgtgt gtgggucu                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 19
agcucctgga gauguagc                                                18

<210> SEQ ID NO 20
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 20
gagcucctgg agauguag                                                18

<210> SEQ ID NO 21
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
```

```
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 21
ggagcucctg gagaugua                                                 18

<210> SEQ ID NO 22
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 22
cccucggggg gcugcggg                                                 18

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 23
gggagagagt ggcagggc                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
```

```
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 24
cgggagagag tggcaggg                                                 18

<210> SEQ ID NO 25
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 25
acgauaacca gaccgcug                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 26
gggagcgggc tgugugga                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 27
acauagtagg tgcacaau                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 28
cacauagtag gtgcacaa                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 29
gggucucact ctgcugcc                                                 18

<210> SEQ ID NO 30
<211> LENGTH: 18
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 30
gggcaggctt ccacucca                                              18

<210> SEQ ID NO 31
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 31
aaagcugtta ggaggaca                                              18

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 32
```
uaaagctgtt aggaggac                                                              18

<210> SEQ ID NO 33
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 33
auaaagctgt taggagga                                                              18

<210> SEQ ID NO 34
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 34
accggcatca aauugugc                                                              18

<210> SEQ ID NO 35
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 35
aaccggcatc aaauugug                                                         18

<210> SEQ ID NO 36
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 36
cuggauttct ttuggggg                                                         18

<210> SEQ ID NO 37
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 37
gcuggatttc ttuugggg                                                         18

<210> SEQ ID NO 38
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:

```
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 38
ggcuggattt ctuuuggg                                                 18

<210> SEQ ID NO 39
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 39
gggcuggatt tcuuuugg                                                 18

<210> SEQ ID NO 40
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 40
ggggcuggat ttcuuuug                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
```

```
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 41
gggagggaat gtgaggag                                                    18

<210> SEQ ID NO 42
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 42
gcugaagagg tgggaggg                                                    18

<210> SEQ ID NO 43
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 43
gagccuggga ggucgagg                                                    18

<210> SEQ ID NO 44
<211> LENGTH: 18
<212> TYPE: DNA
<213> ORGANISM: Artificial Sequence
<220> FEATURE:
```

```
-continued

<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 44
gggaggatga ggcgggca                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 45
ugggaggatg aggcgggc                                                 18

<210> SEQ ID NO 46
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 46
uuuaggaagg ggagcacc                                                 18
```

```
<210> SEQ ID NO 47
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 47
auuuaggaag gggagcac                                              18

<210> SEQ ID NO 48
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 48
uauuuaggaa ggggagca                                              18

<210> SEQ ID NO 49
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

```
<400> SEQUENCE: 49
uuauuuagga aggggagc                                                18

<210> SEQ ID NO 50
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 50
cauuuattta ggaagggg                                                18

<210> SEQ ID NO 51
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 51
ucauuuattt aggaaggg                                                18

<210> SEQ ID NO 52
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
```

```
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 52
gggaugcagg cccggcug                                                       18

<210> SEQ ID NO 53
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 53
aaagaggauc agugguac                                                       18

<210> SEQ ID NO 54
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 54
gaaagaggat caguggua                                                       18

<210> SEQ ID NO 55
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
```

```
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 55
uggguutagg gguagcug                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 56
auggguutag ggguagcu                                                 18

<210> SEQ ID NO 57
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 57
aaugggttta gggguagc                                                 18

<210> SEQ ID NO 58
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

-continued

```
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 58
ugcaaugggt ttaggggu                                                  18

<210> SEQ ID NO 59
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 59
gugcaatggg ttuagggg                                                  18

<210> SEQ ID NO 60
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 60
ugugcaatgg gtuuaggg                                                  18

<210> SEQ ID NO 61
<211> LENGTH: 18
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 61
uugugcaatg gguuuagg                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 62
cuugugcaat ggguuuag                                                 18

<210> SEQ ID NO 63
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 63
gcuugugcaa tggguuua                                                 18
```

<210> SEQ ID NO 64
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 64
agcuugtgca atggguuu                                              18

<210> SEQ ID NO 65
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 65
cagcuugtgc aauggguu                                              18

<210> SEQ ID NO 66
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)

```
<223> OTHER INFORMATION: Modified with /iSp18//iSp18//3CholTEG/

<400> SEQUENCE: 66
gggcauggag agccaugc                                                 18

<210> SEQ ID NO 67
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 67
ucugggagag gcgauggg                                                 18

<210> SEQ ID NO 68
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 68
gggaggtggg ctgggcca                                                 18

<210> SEQ ID NO 69
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
```

<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 69
acuccctctc ctccuccu                                                    18

<210> SEQ ID NO 70
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 70
uacuccctct ccuccucc                                                    18

<210> SEQ ID NO 71
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 71
gggaggcaag gtcugaga                                                    18

<210> SEQ ID NO 72
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:

```
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 72
ucagggcagc ccgggagg                                                       18

<210> SEQ ID NO 73
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 73
cacuccactc accuccca                                                       18

<210> SEQ ID NO 74
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 74
gggugcaggg ctucagac                                                       18

<210> SEQ ID NO 75
<211> LENGTH: 18
<212> TYPE: RNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 75
gcgggugcag ggcuucag                                                 18

<210> SEQ ID NO 76
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 76
cuguuugcuc uccuguca                                                 18

<210> SEQ ID NO 77
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 77
ccuguutgct ctccuguc                                                 18

<210> SEQ ID NO 78
```

```
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 78
uccuguttgc tcuccugu                                                   18

<210> SEQ ID NO 79
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 79
guccugtttg ctcuccug                                                   18

<210> SEQ ID NO 80
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 80
```
uguccugttt gcucuccu                                                    18

<210> SEQ ID NO 81
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 81
cugucctgtt tgcucucc                                                    18

<210> SEQ ID NO 82
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 82
ggcuagtggc tgggaggc                                                    18

<210> SEQ ID NO 83
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:

-continued

```
<221> NAME/KEY: misc_feature
<222> LOCATION: (18)..(18)
<223> OTHER INFORMATION: Modified with /iSp18//iSp18//3CholTEG/

<400> SEQUENCE: 83
ggaaugggag cagauggg                                                 18

<210> SEQ ID NO 84
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 84
gggcuugggc agguggug                                                 18

<210> SEQ ID NO 85
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 85
gggaugggct tgggcagg                                                 18

<210> SEQ ID NO 86
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
```

```
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 86
ggucuccacg gtgauguu                                                 18

<210> SEQ ID NO 87
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 87
guaaugggta gauucguu                                                 18

<210> SEQ ID NO 88
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 88
gguaaugggt agauucgu                                                 18

<210> SEQ ID NO 89
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
```

<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 89
ugguaatggg tagauucg                                                18

<210> SEQ ID NO 90
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 90
cugguaatgg gtagauuc                                                18

<210> SEQ ID NO 91
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 91
gggcgcaggt atguggug                                                18

<210> SEQ ID NO 92
<211> LENGTH: 18
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 92
ggcugagtag atgaucca                                                 18

<210> SEQ ID NO 93
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 93
cgcgccgaac aggucggg                                                 18

<210> SEQ ID NO 94
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 94
guagaggttc tcacauuc                                                 18
```

```
<210> SEQ ID NO 95
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 95
ccgcccgggc tccgcagg                                                    18

<210> SEQ ID NO 96
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 96
cccugggcag gcuuccac                                                    18

<210> SEQ ID NO 97
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

<400> SEQUENCE: 97
caaugggttt agggguag                                                       18

<210> SEQ ID NO 98
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 98
gcaaugggtt tagggua                                                        18

<210> SEQ ID NO 99
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 99
ggaggatgag gcgggcag                                                       18

<210> SEQ ID NO 100
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)

<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 100
gugcggcccc cauggccc                                                    18

<210> SEQ ID NO 101
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 101
cgugcggccc ccauggcc                                                    18

<210> SEQ ID NO 102
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 102
gcgugcggcc cccauggc                                                    18

<210> SEQ ID NO 103
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature

```
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 103
ugcgugcggc ccccaugg                                                     18

<210> SEQ ID NO 104
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 104
cugcgugcgg cccccaug                                                     18

<210> SEQ ID NO 105
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 105
cgggcugcgt gcggcccc                                                     18

<210> SEQ ID NO 106
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 106
gcgggctgcg tgcggccc                                            18

<210> SEQ ID NO 107
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 107
ggcgggctgc gtgcggcc                                            18

<210> SEQ ID NO 108
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 108
ucgcagggag gcgccacc                                            18

<210> SEQ ID NO 109
<211> LENGTH: 18
```

```
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 109
gucgcaggga ggcgccac                                                 18

<210> SEQ ID NO 110
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 110
uucgaugtga gccacggg                                                 18

<210> SEQ ID NO 111
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 111
```
ccauucgaug tgagccac                                          18

<210> SEQ ID NO 112
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 112
gauaactctg cacccucg                                          18

<210> SEQ ID NO 113
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 113
ggcuugggca ggugguga                                          18

<210> SEQ ID NO 114
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature -continued

```
<222> LOCATION: (18)..(18)
<223> OTHER INFORMATION: Modified with /iSp18//iSp18//3CholTEG/

<400> SEQUENCE: 114
ugggcutggg cagguggu                                                   18

<210> SEQ ID NO 115
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 115
aaugggtaga ttcguucc                                                   18

<210> SEQ ID NO 116
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 116
uaaugggtag atucguuc                                                   18

<210> SEQ ID NO 117
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
```

```
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 117 uccccccgcca gtgccagc                                                18

<210> SEQ ID NO 118
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 118
cccucugact ctgaccccc                                                18

<210> SEQ ID NO 119
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 119
gggccccuct gacucuga                                                 18

<210> SEQ ID NO 120
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
```

```
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 120
ugggcccctc tgacucug                                                 18

<210> SEQ ID NO 121
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 121
cugggcccct ctgacucu                                                 18

<210> SEQ ID NO 122
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 122
aggguctcac tcugcugc                                                 18

<210> SEQ ID NO 123
<211> LENGTH: 18
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 123
caggguctca ctcugcug                                                 18

<210> SEQ ID NO 124
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 124
acagggtctc acucugcu                                                 18

<210> SEQ ID NO 125
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 125
gacagggtct cacucugc                                                 18
```

```
<210> SEQ ID NO 126
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 126
agacagggtc tcacucug                                                 18

<210> SEQ ID NO 127
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 127
gagacagggt ctcacucu                                                 18

<210> SEQ ID NO 128
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

-continued

<400> SEQUENCE: 128
ugagacaggg tcucacuc                                              18

<210> SEQ ID NO 129
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 129
gcaggcttcc acuccauc                                              18

<210> SEQ ID NO 130
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 130
cuccactcac ctcccagc                                              18

<210> SEQ ID NO 131
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl

```
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 131
acuccactca cucccag                                                           18

<210> SEQ ID NO 132
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 132
gcucactcca ctcaccuc                                                          18

<210> SEQ ID NO 133
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 133
agcucactcc acucaccu                                                          18

<210> SEQ ID NO 134
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
```

```
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 134
gacaagctca ctccacuc                                              18

<210> SEQ ID NO 135
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 135
uccccccacc ccccaccc                                              18

<210> SEQ ID NO 136
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 136
agggcutcag acucaccu                                              18

<210> SEQ ID NO 137
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 137
cagggcttca gacucacc                                                18

<210> SEQ ID NO 138
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 138
gcagggcttc agacucac                                                18

<210> SEQ ID NO 139
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 139
ugcagggctt cagacuca                                                18

<210> SEQ ID NO 140
<211> LENGTH: 18
<212> TYPE: DNA

-continued

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 140
gugcagggct tcagacuc                                                 18

<210> SEQ ID NO 141
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 141
cgggugcagg gcuucaga                                                 18

<210> SEQ ID NO 142
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 142
cgcgggtgca gggcuuca                                                 18
```

<210> SEQ ID NO 143
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 143
acgcgggtgc agggcuuc                                                 18

<210> SEQ ID NO 144
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 144
aacgcgggtg cagggcuu                                                 18

<210> SEQ ID NO 145
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)

<223> OTHER INFORMATION: Modified with /iSp18//iSp18//3CholTEG/

<400> SEQUENCE: 145
gaacgcgggt gcagggcu                                                          18

<210> SEQ ID NO 146
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 146
cucucctgtc acauuucc                                                          18

<210> SEQ ID NO 147
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 147
gcucucctgt cacauuuc                                                          18

<210> SEQ ID NO 148
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature

```
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 148
ugcucucctg tcacauuu                                               18

<210> SEQ ID NO 149
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 149
uugcuctcct gtcacauu                                               18

<210> SEQ ID NO 150
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 150
uuugcuctcc tgucacau                                               18

<210> SEQ ID NO 151
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
```

```
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 151
guuugctctc ctgucaca                                                18

<210> SEQ ID NO 152
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 152
uguuugctct ccugucac                                                18

<210> SEQ ID NO 153
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 153
ccuguutgct ctccuguc                                                18

<210> SEQ ID NO 154
<211> LENGTH: 18
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 154
agcugaagag gtgggagg                                                 18

<210> SEQ ID NO 155
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 155
gagcugaaga ggugggag                                                 18

<210> SEQ ID NO 156
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a  O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 156
cgagcugaag agguggga                                                 18

<210> SEQ ID NO 157
```

-continued

```
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 157
acgagctgaa gagguggg                                              18

<210> SEQ ID NO 158
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 158
ggcaggcttc cacuccau                                              18

<210> SEQ ID NO 159
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 159
```

```
ugggcaggct tccacucc                                                   18

<210> SEQ ID NO 160
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 160
cugggcaggc ttccacuc                                                   18

<210> SEQ ID NO 161
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 161
ccugggcagg ctuccacu                                                   18

<210> SEQ ID NO 162
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
```

<221> NAME/KEY: misc_feature
<222> LOCATION: (18)..(18)
<223> OTHER INFORMATION: Modified with /iSp18//iSp18//3CholTEG/

<400> SEQUENCE: 162
ccaccuctgc acacucag                                                      18

<210> SEQ ID NO 163
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 163
gccugggagg tcgaggcu                                                      18

<210> SEQ ID NO 164
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 164 agccuggag gtcgaggc                                                       18

<210> SEQ ID NO 165
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond

```
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 165
ugagccuggg aggucgag                                                 18

<210> SEQ ID NO 166
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 166
uugagccugg gaggucga                                                 18

<210> SEQ ID NO 167
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 167
cuugagccug gaggucg                                                  18

<210> SEQ ID NO 168
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
```

<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 168
uugggaggat gaggcggg                                                 18

<210> SEQ ID NO 169
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 169
uuugggagga tgaggcgg                                                 18

<210> SEQ ID NO 170
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 170
gugggatgca ggcccggc                                                 18

<210> SEQ ID NO 171
<211> LENGTH: 18
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 171 uguggatgc aggcccgg                                                    18

<210> SEQ ID NO 172
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 172 uuguggatg caggcccg                                                    18

<210> SEQ ID NO 173
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 173
acuccugccc cacccacu                                                   18
```

```
<210> SEQ ID NO 174
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 174
aggcuggtgc cacucggg                                                 18

<210> SEQ ID NO 175
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 175
gaggaucagt gguaccuc                                                 18

<210> SEQ ID NO 176
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

```
<400> SEQUENCE: 176
aagaggatca gtgguacc                                                18

<210> SEQ ID NO 177
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 177
gcauggagag ccaugcag                                                18

<210> SEQ ID NO 178
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 178
gggaaagagg atcagugg                                                18

<210> SEQ ID NO 179
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
```

<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 179
agggaaagag gaucagug                                                    18

<210> SEQ ID NO 180
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 180
cauggagagc caugcaga                                                    18

<210> SEQ ID NO 181
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 181
ggcauggaga gccaugca                                                    18

<210> SEQ ID NO 182
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature

```
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 182 gggggcatgga gagccaug                                                18

<210> SEQ ID NO 183
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 183 ugggcatgg agagccau                                                  18

<210> SEQ ID NO 184
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 184 augggggcatg gagagcca                                                18

<210> SEQ ID NO 185
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 185
aucugggaga ggcgaugg                                                   18

<210> SEQ ID NO 186
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 186 gaucuggag aggcgaug                                                    18

<210> SEQ ID NO 187
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 187
ggaucuggga gaggcgau                                                   18

<210> SEQ ID NO 188
<211> LENGTH: 18
```

<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 188
cccucuccuc ctccuacc                                                  18

<210> SEQ ID NO 189
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 189
ucccuctcct ccuccuac                                                  18

<210> SEQ ID NO 190
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 190
cucccuctcc tccuccua                                                    18

<210> SEQ ID NO 191
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 191
cuacuccctc tccuccuc                                                    18

<210> SEQ ID NO 192
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 192
ucuacuccct ctccuccu                                                    18

<210> SEQ ID NO 193
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature -continued
<222> LOCATION: (18)..(18)
<223> OTHER INFORMATION: Modified with /iSp18//iSp18//3CholTEG/

<400> SEQUENCE: 193
uucuactccc tcuccucc                                                18

<210> SEQ ID NO 194
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 194
uuucuactcc ctcuccuc                                                18

<210> SEQ ID NO 195
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 195
cuuucuactc ccucuccu                                                18

<210> SEQ ID NO 196
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:

```
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 196
ccuuuctact cccucucc                                               18

<210> SEQ ID NO 197
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 197
cuccuutcta ctcccucu                                               18

<210> SEQ ID NO 198
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 198
ucccuccttt ctacuccc                                               18

<210> SEQ ID NO 199
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
```

```
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 199
ucccucgtca cagccacc                                              18

<210> SEQ ID NO 200
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 200
gcucuctctg ccucucgu                                              18

<210> SEQ ID NO 201
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 201
gagcuctctc tgccucuc                                              18

<210> SEQ ID NO 202
<211> LENGTH: 18
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 202
gggcuucaga ctcaccuu                                                       18

<210> SEQ ID NO 203
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 203
cuccgcaggt aguugucc                                                       18

<210> SEQ ID NO 204
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 204
ggcuccgcag gtaguugu                                                       18
```

-continued

```
<210> SEQ ID NO 205
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 205
gggcuccgca gguaguug                                                 18

<210> SEQ ID NO 206
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 206
acacccacag gggcaugu                                                 18

<210> SEQ ID NO 207
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

```
<400> SEQUENCE: 207
uccccgacca gcggucu                                                  18

<210> SEQ ID NO 208
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 208
cuccccgacc agcgggguc                                                18

<210> SEQ ID NO 209
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 209
cguagggcgt gtgugggu                                                 18

<210> SEQ ID NO 210
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
```

```
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 210
ucguagggcg tguguggg                                                   18

<210> SEQ ID NO 211
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 211
cucguagggc gtgugugg                                                   18

<210> SEQ ID NO 212
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 212
ccucguaggg cgugugug                                                   18

<210> SEQ ID NO 213
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
```

<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with/iSp18//iSp18//3CholTEG/

<400> SEQUENCE: 213
uccucgtagg gcgugugu                                                 18

<210> SEQ ID NO 214
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 214
cuccucgtag ggcgugug                                                 18

<210> SEQ ID NO 215
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 215
gggcgucaaa caguuauu                                                 18

<210> SEQ ID NO 216
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature

```
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 216
uccaauaaag ctguuagg                                                 18

<210> SEQ ID NO 217
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 217
cuccaataaa gcuguuag                                                 18

<210> SEQ ID NO 218
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 218
acuccaataa agcuguua                                                 18

<210> SEQ ID NO 219
<211> LENGTH: 18
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 219
uacuccaata aagcuguu                                                 18

<210> SEQ ID NO 220
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 220
ugcccuattt aauuuuca                                                 18

<210> SEQ ID NO 221
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 221
augccctatt taauuuuc                                                 18
```

<210> SEQ ID NO 222
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 222
uaugccctat ttaauuuu                                                 18

<210> SEQ ID NO 223
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 223
cucauutatt taggaagg                                                 18

<210> SEQ ID NO 224
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)

<223> OTHER INFORMATION: Modified with /iSp18//iSp18//3CholTEG/

<400> SEQUENCE: 224
ccucauttat ttaggaag                                                    18

<210> SEQ ID NO 225
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 225
gcuugggcag gtggugaa                                                    18

<210> SEQ ID NO 226
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 226
uccacucacc tcccagca                                                    18

<210> SEQ ID NO 227
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 227
ucacuccact caccuccc                                                 18

<210> SEQ ID NO 228
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 228
uccccacccc tgagcucu                                                 18

<210> SEQ ID NO 229
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 229
agaggatcag tgguaccu                                                 18

<210> SEQ ID NO 230
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:

```
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 230
gcuccgcagg taguuguc                                                    18

<210> SEQ ID NO 231
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 231
cucacuccac tcaccucc                                                    18

<210> SEQ ID NO 232
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 232
augggcuugg gcaggugg                                                    18

<210> SEQ ID NO 233
<211> LENGTH: 18
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 233
auggguagat tcguucca                                                       18

<210> SEQ ID NO 234
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 234
cacucutgaa gcucuugg                                                       18

<210> SEQ ID NO 235
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 235
cgucaaacag ttauuuau                                                       18

<210> SEQ ID NO 236
```

```
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 236
ggcuggattt ctuuuggg                                                   18

<210> SEQ ID NO 237
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 237
cuccucgtag ggcgugug                                                   18

<210> SEQ ID NO 238
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 238
```
ggcaggtggt gaacgguc                                                    18

<210> SEQ ID NO 239
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 239
gggcaggtgg tgaacggu                                                    18

<210> SEQ ID NO 240
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 240
ugggcaggtg gtgaacgg                                                    18

<210> SEQ ID NO 241
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:

```
<221> NAME/KEY: misc_feature
<222> LOCATION: (18)..(18)
<223> OTHER INFORMATION: Modified with /iSp18//iSp18//3CholTEG/

<400> SEQUENCE: 241
uugggcaggt ggugaacg                                                 18

<210> SEQ ID NO 242
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 242
cuugggcagg tggugaac                                                 18

<210> SEQ ID NO 243
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 243
cacaggggca tguagucc                                                 18

<210> SEQ ID NO 244
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
```

```
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 244
ccacaggggc atguaguc                                                 18

<210> SEQ ID NO 245
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 245
cccacagggg cauguagu                                                 18

<210> SEQ ID NO 246
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 246
cacccacagg ggcaugua                                                 18

<210> SEQ ID NO 247
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
```

```
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 247
uacacccaca ggggcaug                                                 18

<210> SEQ ID NO 248
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 248
guacacccac aggggcau                                                 18

<210> SEQ ID NO 249
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 249
aguacaccca caggggca                                                 18

<210> SEQ ID NO 250
<211> LENGTH: 18
<212> TYPE: RNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 250
caguacaccc acagggc                                                  18

<210> SEQ ID NO 251
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 251
ccaguacacc cacagggg                                                 18

<210> SEQ ID NO 252
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 252
guagggcgtg tgugguc                                                  18
```

<210> SEQ ID NO 253
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 253
ccuccucgta gggcgugu                                                 18

<210> SEQ ID NO 254
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 254
uccucctcgt agggcgug                                                 18

<210> SEQ ID NO 255
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

-continued

<400> SEQUENCE: 255
cuccucctcg tagggcgu                                                 18

<210> SEQ ID NO 256
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 256
gcuccucctc gtagggcg                                                 18

<210> SEQ ID NO 257
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 257
gcutgggcag gtggtgaa                                                 18

<210> SEQ ID NO 258
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)

<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 258
ucctcgtagg gcgtgugu                                                        18

<210> SEQ ID NO 259
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with a O methyl
<220> FEATURE:
<221> NAME/KEY: misc_feature
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 259
gcuugggcag gtggugaa                                                        18

<210> SEQ ID NO 260
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with a O methyl
<220> FEATURE:
<221> NAME/KEY: misc_feature
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 260
acacccacag gggcaugu                                                        18

<210> SEQ ID NO 261
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with a O methyl
<220> FEATURE:
<221> NAME/KEY: misc_feature

```
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 261
cguagggcgt gtgtgggu                                                 18

<210> SEQ ID NO 262
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with a O methyl
<220> FEATURE:
<221> NAME/KEY: misc_feature
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 262
uccucgtagg gcgtgugu                                                 18

<210> SEQ ID NO 263
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 263
gcuugggcag gtggugaa                                                 18

<210> SEQ ID NO 264
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 264
acacccacag gggcaugu                                                   18

<210> SEQ ID NO 265
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 265
cguagggcgt gtgugggu                                                   18

<210> SEQ ID NO 266
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 266
uccucgtagg gcgugugu                                                   18

<210> SEQ ID NO 267
<211> LENGTH: 18
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 267
gcuugggcag gtggtgaa                                                 18

<210> SEQ ID NO 268
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 268
acacccacag gggcaugu                                                 18

<210> SEQ ID NO 269
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 269
```

-continued uccucguagg gcgtgugu                                                        18

<210> SEQ ID NO 270
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 270
gcutgggcag guggugaa                                                        18

<210> SEQ ID NO 271
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 271
acacccacag gggcaugu                                                        18

<210> SEQ ID NO 272
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature -continued
<222> LOCATION: (18)..(18)
<223> OTHER INFORMATION: Modified with /iSp18//iSp18//3CholTEG/

<400> SEQUENCE: 272
cguagggcgu gugugggu                                                       18

<210> SEQ ID NO 273
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 273
ucctcgtagg gcgugugu                                                       18

<210> SEQ ID NO 274
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 274
gcuugggcag gtggugaa                                                       18

<210> SEQ ID NO 275
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:

```
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 275
acacccacag gggcaugu                                                18

<210> SEQ ID NO 276
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 276
cguagggcgt gtgugggu                                                18

<210> SEQ ID NO 277
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 277
uccucguagg gcgugugu                                                18

<210> SEQ ID NO 278
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
```

```
<220> FEATURE:
<221> NAME/KEY: misc_feature
<222> LOCATION: (6)..(12)
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 278
gcuugggcag guggugaa                                                 18

<210> SEQ ID NO 279
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(12)
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 279
acacccacag gggcaugu                                                 18

<210> SEQ ID NO 280
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(12)
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 280
cguagggcgt gugugggu                                                 18

<210> SEQ ID NO 281
<211> LENGTH: 18
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(12)
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 281
uccucgtagg gcgugugu                                                    18

<210> SEQ ID NO 282
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 282
acacccacag gggcaugu                                                    18

<210> SEQ ID NO 283
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 283
cguagggcgt gtgtgggu                                                    18
```

```
<210> SEQ ID NO 284
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 284
acccacaggg gcauguag                                              18

<210> SEQ ID NO 285
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 285
cguagggcgt gtgtgggu                                              18

<210> SEQ ID NO 286
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/
```

```
<400> SEQUENCE: 286
cccacagggg catgtagu                                                  18

<210> SEQ ID NO 287
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(12)
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 287
cccacagggg cauguagu                                                  18

<210> SEQ ID NO 288
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 288
cccacagggg catguagu                                                  18

<210> SEQ ID NO 289
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: Modified with a O methyl
<220> FEATURE:
<221> NAME/KEY: misc_feature
<222> LOCATION: (8)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
```

```
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 289
guagggcgtg tgtggguc                                                 18

<210> SEQ ID NO 290
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 290
guagggcgtg ugtggguc                                                 18

<210> SEQ ID NO 291
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(9)
<223> OTHER INFORMATION: Modified with a O methyl
<220> FEATURE:
<221> NAME/KEY: misc_feature
<222> LOCATION: (10)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 291
guagggcgug tgtggguc                                                 18

<210> SEQ ID NO 292
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(12)
```

```
<223> OTHER INFORMATION: Modified with a phosphorothioate bond
<220> FEATURE:
<221> NAME/KEY: misc_feature
<222> LOCATION: (12)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 292
guagggcgtg tguggguc                                                 18

<210> SEQ ID NO 293
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(10)
<223> OTHER INFORMATION: Modified with a phosphorothioate bond
<220> FEATURE:
<221> NAME/KEY: misc_feature
<222> LOCATION: (10)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 293
cccacagggg cauguagu                                                 18

<210> SEQ ID NO 294
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 294
guagggcgtg tgtgdgguc                                                18

<210> SEQ ID NO 295
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

-continued

```
<222> LOCATION: (1)..(4)
<223> OTHER INFORMATION: Modified with a O methyl
<220> FEATURE:
<221> NAME/KEY: misc_feature
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 295
guagggcgtg tgtggguc                                                 18

<210> SEQ ID NO 296
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: Modified with a O methyl
<220> FEATURE:
<221> NAME/KEY: misc_feature
<222> LOCATION: (4)..(16)
<223> OTHER INFORMATION: Modified with a phosphorothioate bond
<220> FEATURE:
<221> NAME/KEY: misc_feature
<222> LOCATION: (16)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 296
cccacagggg catgtagu                                                 18

<210> SEQ ID NO 297
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with a O methyl
<220> FEATURE:
<221> NAME/KEY: misc_feature
<222> LOCATION: (5)..(15)
<223> OTHER INFORMATION: Modified with a phosphorothioate bond
<220> FEATURE:
<221> NAME/KEY: misc_feature
<222> LOCATION: (15)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 297
cccacagggg catguagu                                                 18

<210> SEQ ID NO 298
<211> LENGTH: 18
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 298
cccacagggg catguagu                                                 18

<210> SEQ ID NO 299
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with a O methyl
<220> FEATURE:
<221> NAME/KEY: misc_feature
<222> LOCATION: (6)..(14)
<223> OTHER INFORMATION: Modified with a phosphorothioate bond
<220> FEATURE:
<221> NAME/KEY: misc_feature
<222> LOCATION: (14)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 299
guagggcgtg tgtgggguc                                                18

<210> SEQ ID NO 300
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 300
guuucaccac ccaauucc                                                 18
```

<210> SEQ ID NO 301
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with a O methyl
<220> FEATURE:
<221> NAME/KEY: misc_feature
<222> LOCATION: (7)..(13)
<223> OTHER INFORMATION: Modified with a phosphorothioate bond
<220> FEATURE:
<221> NAME/KEY: misc_feature
<222> LOCATION: (13)..(18)
<223> OTHER INFORMATION: Modified with a O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 301
ugggagtaga caagguac                                              18

<210> SEQ ID NO 302
<211> LENGTH: 8608
<212> TYPE: DNA
<213> ORGANISM: Homo sapiens

<400> SEQUENCE: 302
ctgggcccgg gctggaagcc ggaagcgagc aaagtggagc cgactcgaac tccaccgcgg    60
aaaagaaagc tcagaacgt tcgttcgctg cgtcccagc cggggccgag ccctccgcga    120
cgccagccgg gccatggggg ccgcacgcag cccgccgtcc gctgtcccgg ggcccctgct    180
ggggctgctc ctgctgctcc tgggcgtgct ggccccgggt ggcgcctccc tgcgactcct    240
ggaccaccgg gcgctggtct gctcccagcc ggggctaaac tgcacggtca agaatagtac    300
ctgcctggat gacagctgga ttcaccctcg aaacctgacc ccctcctccc caaaggacct    360
gcagatccag ctgcactttg cccacaccca acaaggagac ctgttccccg tggctcacat    420
cgaatggaca ctgcagacag acgccagcat cctgtacctc gagggtgcag agttatctgt    480
cctgcagctg aacaccaatg aacgtttgtg cgtcaggttt gagtttctgt ccaaactgag    540
gcatcaccac aggcggtggc gttttacctt cagccacttt gtggttgacc ctgaccagga    600
atatgaggtg accgttcacc acctgcccaa gccatccct gatggggacc caaaccacca    660
gtccaagaat ttccttgtgc ctgactgtga gcacgccagg atgaaggtaa ccacgccatg    720
catgagctca ggcagcctgt gggacccccaa catcaccgtg gagaccctgg aggcccacca    780
gctgcgtgtg agcttcaccc tgtggaacga atctacccat taccagatcc tgctgaccag    840
ttttccgcac atggagaacc acagttgctt tgagcacatg caccacatac ctgcgcccag    900
accagaagag ttccaccagc gatccaacgt cacactcact ctacgcaacc ttaaagggtg    960
ctgtcgccac caagtgcaga tccagccctt cttcagcagc tgcctcaatg actgcctcag    1020
acactccgcg actgtttcct gcccagaaat gccagacact ccagaaccaa ttccggacta    1080
catgcccctg tgggtgtact ggttcatcac gggcatctcc atcctgctgg tgggctccgt    1140
catcctgctc atcgtctgca tgaccctgga gctagctggg cctggaagtg aaaaatacag    1200
tgatgacacc aaatacaccg atggcctgcc tgcggctgac ctgatccccc caccgctgaa    1260

```
gcccaggaag gtctggatca tctactcagc cgaccacccc ctctacgtgg acgtggtcct   1320
gaaattcgcc cagttcctgc tcaccgcctg cggcacggaa gtggccctgg acctgctgga   1380
agagcaggcc atctcggagg caggagtcat gacctgggtg ggccgtcaga agcaggagat   1440
ggtggagagc aactctaaga tcatcgtcct gtgctcccgc ggcacgcgcg ccaagtggca   1500
ggcgctcctg ggccgggggg cgcctgtgcg gctgcgctgc gaccacggaa agcccgtggg   1560
ggacctgttc actgcagcca tgaacatgat cctcccggac ttcaagaggc cagcctgctt   1620
cggcacctac gtagtctgct acttcagcga ggtcagctgt gacggcgacg tccccgacct   1680
gttcggcgcg cgccgcggt acccgctcat ggacaggttc gaggaggtgt acttccgcat   1740
ccaggacctg gagatgttcc agccgggccg catgcaccgc gtaggggagc tgtcggggga   1800
caactacctg cggagcccgg gcggcaggca gctccgcgcc gccctggaca ggttccggga   1860
ctggcaggtc cgctgtcccg actggttcga atgtgagaac ctctactcag cagatgacca   1920
ggatgccccg tccctggacg aagaggtgtt tgaggagcca ctgctgcctc cgggaaccgg   1980
catcgtgaag cgggcgcccc tggtgcgcga gcctggctcc caggcctgcc tggccataga   2040
cccgctggtc ggggaggaag gaggagcagc agtggcaaag ctggaacctc acctgcagcc   2100
ccggggtcag ccagcgccgc agcccctcca caccctggtg ctcgccgcag aggaggggc   2160 cctggtggcc gcggtggagc ctgggcccct ggctgacggt gccgcagtcc ggctggcact   2220 ggcggggag ggcgaggcct gcccgctgct gggcagcccg ggcgctgggc gaaatagcgt   2280
cctcttcctc cccgtggacc ccgaggactc gccccttggc agcagcaccc ccatggcgtc   2340
tcctgacctc cttccagagg acgtgaggga gcacctcgaa ggcttgatgc tctcgctctt   2400
cgagcagagt ctgagctgcc aggcccaggg gggctgcagt agacccgcca tggtcctcac   2460
agacccacac acgccctacg aggaggagca gcggcagtca gtgcagtctg accagggcta   2520
catctccagg agctccccgc agcccccga gggactcacg gaaatggagg aagaggagga   2580
agaggagcag gacccaggga agccggccct gccactctct cccgaggacc tggagagcct   2640
gaggagcctc cagcggcagc tgcttttccg ccagctgcag aagaactcgg gctgggacac   2700 gatgggtca gagtcagagg ggcccagtgc atgagggcgg ctccccaggg accgcccaga   2760
tcccagcttt gagagaggag tgtgtgtgca cgtattcatc tgtgtgtaca tgtctgcatg   2820
tgtatatgtt cgtgtgtgaa atgtaggctt taaaatgtaa atgtctggat tttaatccca   2880
ggcatccctc ctaactttc tttgtgcagc ggtctggtta tcgtctatcc caggggaat    2940 ccacacagcc cgctcccagg agctaatggt agagcgtcct tgaggctcca ttattcgttc   3000
attcagcatt tattgtgcac ctactatgtg gcgggcattt gggataccaa gataaattgc   3060
atgcggcatg gccccagcca tgaaggaact taaccgctag tgccgaggac acgttaaacg   3120
aacaggatgg gccgggcacg gtggctcacg cctgtaatcc cagcacactg ggaggccgag   3180
gcaggtggat cactctgagg tcaggagttt gagccagcct ggccaacatg gtgaaacccc   3240
atctccacta aaaatagaaa aattagccgg gcatggtgac acatgcctgt agtcctagct   3300
acttgggagg ctgaggcagg agaattgctt gaatctggga ggcagaggtt gcagtgagcc   3360
gagattgtgc cattgcactg cagcctggat gacagagcga gactctatct caaaaaaaaa   3420 aaaaaaaaa gatggtcacg cgggatgtaa acgctgaatg ggccaggtgc agtggctcat   3480
gcttgtaatc ccagcacttt gggaaggcga ggcaggtgga ttgcttgagc tcaggagttc   3540
aagaccagcc tgggcgacat agtgagacct catctctacc taaattttt tttagtcagt   3600 catggtggca catgcctgta gtcccagcta ctcgggaggc tgatgccaga tgatcacttg   3660
```

```
agcccaggag gtagaggctg cagtgagcta taatggtacc attgcaatcc agcctgggca    3720
gcagagtgag accctgtctc aaaaaaaata aaaaagtaga aagatggagt ggaagcctgc    3780
ccagggttgt gagcatgcac gggaaaggca cccaggtcag gggggatccc cgaggagatg    3840
cctgagctga aggattgtgg ttggggaaag cgtagtccca gcaaggaagc agtttgtggg    3900
taagtgctgg gaggtgagtg gagtgagctt gtcaggagc tgctggtgga gcctggaggg    3960
gaaggaggga ggcagtgaga gagatcgggg tgggggtgg ggggatgtcg ccagagctca    4020
ggggtgggga cagccttgtg cgcatcagtc ctgaggcctg ggcacccttt cgtctgatga    4080
gcctctgcat ggagagaggc tgagggctaa acacagctgg atgtcacctg agttcattta    4140
taggaagaga gaaatgtcga ggtgaaacgt aaaagcatct ggcaggaagg tgagtctgaa    4200
gccctgcacc cgcgttccga ctatcagtgg ggagctgtta gcacgtagga ttcttcagag    4260
cagctgggct ggagctcccc tgagctcagg aagccccagg gtgcaagggc aaggaaatga    4320
ggggtggtgg gtcagtgaag atctgggcag accttgtgtg gggaaggggt gctgctgtga    4380
cttcagggtc tgaggtccaa agacagcatt tgaaagagg ctctgaagcc agtgtttgaa    4440
gaatttgttc ctgaagtacc tcctgggggt aggctagagg cttctggctt cagggtcctg    4500
aagaacacat tgaggtgccg tctgacactg aatagggtg cccttcattc ctatgcctga    4560
gtccttaact atatttccaa cctccagtga ggaggagaag attcggaaat gtgacaggag    4620
agcaaacagg acagtttgca tgtgtgtgtg cgcacacata catgtgcgtg aaagattatc    4680
aataaaagtg cataaatttg ttgatctggt aagagtttct agcaggaagg tcgagccact    4740
tactgtaggt caagaagttg ctagttgcgg agttttttct tgcagttaga ctttacctag    4800
tggtagcagg gccaccaaag ctctgtgtcc cagatggtgt atggcccata atccacccaa    4860
cagcagcaaa ggaccaggca aaggagaaca ggagcagaag cctcccagcc actagccttt    4920
tgggctcagt ctctccaata atcctggaga ggggcttcgt tgggtctgga cacctaccat    4980
gcattctgtg acctttccct agcttccaat aaataactgt ttgacgccca gagtacagga    5040
taccacaatg cactcttcct gcgtagagca catgttccca tctgctccca ttcctcagga    5100
accttgaatt ctagctctgc tggcctttga gcccatgcca gtaaatgtcc tgatgggcat    5160
tgcctactat ctccagggca gctgcctttg tcctcctaac agctttattg gagtacagtt    5220
cacttaccat acaatccaca attgaccctg cacaatttga tgccggttta gtatagtcac    5280
agttcagcag ccatcagcac agtcagtctt agagtttact accccccaaaa gaaatccagc    5340 cccccttagt caccacccca acctcccat ccctaggcac ccctaggcta ctttgatctc    5400
tgtagacttg cctcttctgg acatgacata gagaaaggag tcataaattc tccaaggtgt    5460
ctgtttcttc tttaatgtca ttccctgttt ctcctcacat tccctcccca tttcctgggc    5520
ccagtctcac actggtcctt gcttacccta aatgctatta attccatcac tctgagtatg    5580
gtgtttgctc tccgctgaat gccaagagct tcaagagtgt gtgtaaataa agccacacct    5640
ttatttttgt attattctga accatggcta ataaattgtt tcaccaagaa atgtctctct    5700
aagaacaggt gccctccacg ctgtgcccct cccacctctt cagctcgtct cctgagtgtg    5760
cagaggtggt tccggttggg aaagaagcag cggagctcatc aaccatgcct gtgtccaggc    5820
cgattatgca cgcagccacc aacaagctcc caactcccgc gtagagtttc atgactttt    5880 cctgcctact atcttgatcc tagtttttttt tttgttttttt ttttttttaa ggaataatta    5940
ctttgattca aaaccagttt ctcttttctg cataggaagg tccttgaagg tgtttagggt    6000
```

```
ctaaaaaggg tggtgttcgg tctctgaaac atccattcag cagtttgagc tgggatctct    6060
gaatgcaagg gtatgatgga tatacttctt tcttgctttt gttgtgtttt ggtttttgt    6120 ttgtttttaa gtcagggtct ctctgtcacc aggctgtatt acagtggtgc aatcatggct    6180
cactgcagcc tcgacctccc aggctcaagc catctttcca cctcagcctg ccagtggcta    6240
gaactacagg cgtgcaccac tgtgcccggc taatttgtgt gtatatattt tgtagaaatg    6300
gggtttcacc atgttgtcca ggctggtcac gaactcctgg gctcaagcca tctgcccgcc    6360
tcatcctccc aaagtgctgg gattataggc ctgagcccac cgtgcctggc ctttcctgtt    6420
tatctttgaa aattaaatag gcataagag agaagaagat gtacttacaa tgcagtgggt    6480
ggttttaact ctatagcctt tgggctctgt ggttggtgct ccccttccta aataaatgag    6540
gtgtatgcag ggccctcttc tgccttagcg ccctgccagc tgggactcca gcaaggcccg    6600
gggcacctga ggacagagtg agatggaggg ccgctgctcc agcagccggg cctgcatccc    6660
acaagtcaac tgtgtcggac agaggatcct tacaaagaag aggcagcagg ttgggggct    6720 ggccagctgc tcgtccgccc taggtagctt gctcatctgt aaagtgggtg gggcaggagt    6780
tcccacctca tggggtcctg gcaagcctgc agtatccccg agtggcacca gcctgcttct    6840
ggggcagagc agtttgtgcc ccctgaggta ccactgatcc tctttccctg ctattaggta    6900
ttgctctctt cctccggtgt ttgccttttc agattataga agtaatatgt gttcccatat    6960
ttggcgtctc tcaggagctc aggaagtact tggctgagtg aacatgtcca ttgtggaaaa    7020
atggcaacaa tatggattcc atgggtatat tttatagaag aatatgaaga aaagcagcta    7080
cccctaaacc cattgcacaa gctgttcatg ttaattctgt acccgacgct ttccccacgg    7140
ggcctcccct cactctgaaa tggcatccag gtccatcttg ccctccacct ctgcatggct    7200
ctccatgccc catcgcctct cccagatcct agcactgggt ccacactctc gccctgtcca    7260
tttaggttga tgaaagcagg cagtcacccg ggtgggccag tcttgcctgt gggaggaaca    7320
tgcagtctct tgtctcatgg tttgaagtgt gccaggaagc ctggcccagc ccacctcccc    7380
ctggagtcct tcccaggagg aataacccct taggtcattg actataagat gagttcgctc    7440
actggatcct tcctctctga tgagacagga agaaggtaca cagtgaccag gtaggaggag    7500
gagagggagt agaaaggagg gatgcgggtg gctggtccct gcatttgcct gcttccctgc    7560
acgggtgtcc cactggccgc ctctgctcac cagtgtcatg ggattctctc agaagatgaa    7620
aacagcccct gctttttgc tagaatggct gagctttcat ggaaaggaag ctggacccaa    7680
gcaacagccg actaccgaag gttgcctgga gcagtgcaga tgtgggagga agaagggcct    7740
tggtgcacac tggcttttct tcctgactgc aatgtggcat tgtgccagct acctcctctt    7800
tctcggcctc aggaaaatgg agagaaagca gccctgaagg tggctgtgac gagggaaggg    7860
gcagagggcc tgacagtcaa ccacgcgcta tattttcctg ttcttcctta gggcaagaac    7920
tgcatggcca gactcaggca aggcctaggt gtgggctggg cattgcctac acgtgaagag    7980
atcactccgc gtccctactg cacctgtcac aaagtgcctt ctgatatgcc tggcaaacca    8040
aaatcggtga gcgccagctt gcttccctag aagacatttc taaatattca taacatgctt    8100
gctcaaatca atcaccttat tttacatccg ctccagggag aaatgaagac atggtcctac    8160
gttgttctgt aattatttc tatgtaaatt ttgttccttg ttacaattat atatgtctta    8220
ggggaaagga ccatttcaca tgtgtcacct catgtgattc tcaccacagc cctgtgattg    8280
ctcctgtttt ataaataatg acatagttcc agttgatggc caaagccaca gctaacgaga    8340
ggcagagaga gctcaggctc ccaggagctt ccactctcag accttgcctc ccgggctgcc    8400
```

| | |
|---|---:|
| ctgagtgaaa cgcctgctta gcatttggca cagccagaag cagcaagcta gggtcacaac | 8460 |
| acagagaggg gctgtgtaat actggctgcc tctgtgctaa gaaaaaaaaa aaatcactgt | 8520 |
| gtgtttgttt attttggtgc aggcccagtg ttcttgctta gacttaatac taccccttcat | 8580 |
| gttaaaataa aaccaaacaa aaacccat | 8608 |

<210> SEQ ID NO 303

<400> SEQUENCE: 303

000

<210> SEQ ID NO 304
<211> LENGTH: 3634
<212> TYPE: DNA
<213> ORGANISM: Homo sapiens

<400> SEQUENCE: 304

| | |
|---|---:|
| gaattccggg tgatttcact cccggctgtc caggcttgtc ctgctacccc acccagcctt | 60 |
| tcctgaggcc tcaagcctgc caccaagccc ccagctcctt ctccccgcag gacccaaaca | 120 |
| caggcctcag gactcaacac agcttttccc tccaacccgt tttctctccc tcaacggact | 180 |
| cagctttctg aagcccctcc cagttctagt tctatctttt tcctgcatcc tgtctggaag | 240 |
| ttagaaggaa acagaccaca gacctggtcc ccaaaagaaa tggaggcaat aggttttgag | 300 |
| gggcatgggg acggggttca gcctccaggg tcctacacac aaatcagtca gtggcccaga | 360 |
| agacccccct cggaatcgga gcagggagga tggggagtgt gaggggtatc cttgatgctt | 420 |
| gtgtgtcccc aactttccaa atccccgccc ccgcgatgga gaagaaaccg agacagaagg | 480 |
| tgcagggccc actaccgctt cctccagatg agctcatggg tttctccacc aaggaagttt | 540 |
| tccgctggtt gaatgattct ttccccgccc tcctctcgcc ccagggacat ataaaggcag | 600 |
| ttgttggcac acccagccag cagacgctcc ctcagcaagg acagcagagg accagctaag | 660 |
| agggagagaa gcaactacag accccccctg aaaacaaccc tcagacgcca catcccctga | 720 |
| caagctgcca gcaggttct cttcctctca catactgacc cacggcttca ccctctctcc | 780 |
| cctggaaagg acaccatgag cactgaaagc atgatccggg acgtggagct ggccgaggag | 840 |
| gcgctccca agaagacagg ggggcccag gctccaggc ggtgcttgtt cctcagcctc | 900 |
| ttctccttcc tgatcgtggc aggcgccacc acgctcttct gcctgctgca ctttggagtg | 960 |
| atcggccccc agagggaaga ggtgagtgcc tggccagcct tcatccactc tcccacccaa | 1020 |
| ggggaaatga gagacgcaag agagggagag agatgggatg ggtgaaagat gtgcgctgat | 1080 |
| agggagggat gagagagaaa aaaacatgga gaaagacggg gatgcagaaa gagatgtggc | 1140 |
| aagagatggg gaagagagag agagaaagat ggagagacag gatgtctggc acatggaagg | 1200 |
| tgctcactaa gtgtgtatgg agtgaatgaa tgaatgaatg aatgaacaag cagatatata | 1260 |
| aataagatat ggagacagat gtgggtgtg agaagagaga tggggaaga aacaagtgat | 1320 |
| atgaataaag atggtgagac agaaagagcg ggaaatatga cagctaagga gagagatggg | 1380 |
| ggagataagg agagaagaag ataggtgtc tggcacacag aagacactca gggaaagagc | 1440 |
| tgttgaatgc tggaaggtga atacacagat gaatggagag agaaaccag acacctcagg | 1500 |
| gctaagagcg caggccagac aggcagccag ctgttcctcc tttaagggtg actccctcga | 1560 |
| tgttaaccat tctccttctc cccaacagtt ccccaggac ctctctctaa tcagccctct | 1620 |
| ggcccaggca gtcagtaagt gtctccaaac ctctttccta attctgggtt tgggtttggg | 1680 |

```
ggtagggtta gtaccggtat ggaagcagtg ggggaaattt aaagttttgg tcttggggga    1740
ggatggatgg aggtgaaagt aggggggtat tttctaggaa gtttaagggt ctcagctttt    1800
tcttttctct ctcctcttca ggatcatctt ctcgaacccc gagtgacaag cctgtagccc    1860
atgttgtagg taagagctct gaggatgtgt cttggaactt ggagggctag gatttgggga    1920
ttgaagcccg gctgatggta ggcagaactt ggagacaatg tgagaaggac tcgctgagct    1980
caagggaagg gtgaggaac agcacaggcc ttagtgggat actcagaacg tcatggccag     2040
gtgggatgtg ggatgacaga cagagaggac aggaaccgga tgtggggtgg gcagagctcg    2100
agggccagga tgtggagagt gaaccgacat ggccacactg actctcctct ccctctctcc    2160
ctccctccag caaaccctca agctgagggg cagctccagt ggctgaaccg ccgggccaat    2220
gccctcctgg ccaatggcgt ggagctgaga gataaccagc tggtggtgcc atcagagggc    2280
ctgtacctca tctactccca ggtcctcttc aagggccaag gctgcccctc cacccatgtg    2340
ctcctcaccc acaccatcag ccgcatcgcc gtctcctacc agaccaaggt caacctcctc    2400
tctgccatca agagcccctg ccagagggag accccagagg gggctgaggc caagccctgg    2460
tatgagccca tctatctggg aggggtcttc cagctggaga agggtgaccg actcagcgct    2520
gagatcaatc ggcccgacta tctcgacttt gccgagtctg ggcaggtcta ctttgggatc    2580
attgccctgt gaggaggacg aacatccaac cttcccaaac gcctcccctg ccccaatccc    2640
tttattaccc cctccttcag acaccctcaa cctcttctgg ctcaaaaaga gaattggggg    2700
cttagggtcg gaacccaagc ttagaacttt aagcaacaag accaccactt cgaaacctgg    2760
gattcaggaa tgtgtggcct gcacagtgaa gtgctggcaa ccactaagaa ttcaaactgg    2820
ggcctccaga actcactggg gcctacagct ttgatccctg acatctggaa tctggagacc    2880
agggagcctt tggttctggc cagaatgctg caggacttga gaagacctca cctagaaatt    2940
gacacaagtg gaccttaggc cttcctctct ccagatgttt ccagacttcc ttgagacacg    3000
gagcccagcc ctccccatgg agccagctcc ctctatttat gtttgcactt gtgattattt    3060
attatttatt tattatttat ttatttacag atgaatgtat ttatttggga gaccggggta    3120
tcctggggga cccaatgtag gagctgcctt ggctcagaca tgttttccgt gaaaacggag    3180
ctgaacaata ggctgttccc atgtagcccc ctggcctctg tgccttcttt tgattatgtt    3240
ttttaaaata tttatctgat taagttgtct aaacaatgct gatttggtga ccaactgtca    3300
ctcattgctg agcctctgct ccccagggga gttgtgtctg taatcgccct actattcagt    3360
ggcgagaaat aaagtttgct tagaaaagaa acatggtctc cttcttggaa ttaattctgc    3420
atctgcctct tcttgtgggt gggaagaagc tccctaagtc ctctctccac aggctttaag    3480
atccctcgga cccagtccca tccttagact cctagggccc tggagaccct acataaacaa    3540
agcccaacag aatattcccc atccccagg aaacaagagc ctgaacctaa ttacctctcc      3600
ctcagggcat gggaatttcc aactctggga attc                                3634
```

<210> SEQ ID NO 305
<211> LENGTH: 866
<212> TYPE: PRT
<213> ORGANISM: Homo sapiens

<400> SEQUENCE: 305

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser

-continued

```
                20                  25                  30
Leu Arg Leu Leu Asp His Arg Ala Leu Val Cys Ser Gln Pro Gly Leu
            35                  40                  45
Asn Cys Thr Val Lys Asn Ser Thr Cys Leu Asp Asp Ser Trp Ile His
        50                  55                  60
Pro Arg Asn Leu Thr Pro Ser Ser Pro Lys Asp Leu Gln Ile Gln Leu
65                  70                  75                  80
His Phe Ala His Thr Gln Gln Gly Asp Leu Phe Pro Val Ala His Ile
                85                  90                  95
Glu Trp Thr Leu Gln Thr Asp Ala Ser Ile Leu Tyr Leu Glu Gly Ala
            100                 105                 110
Glu Leu Ser Val Leu Gln Leu Asn Thr Asn Glu Arg Leu Cys Val Arg
        115                 120                 125
Phe Glu Phe Leu Ser Lys Leu Arg His His Arg Arg Trp Arg Phe
    130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
            180                 185                 190
Thr Thr Pro Cys Met Ser Ser Gly Ser Leu Trp Asp Pro Asn Ile Thr
        195                 200                 205
Val Glu Thr Leu Glu Ala His Gln Leu Arg Val Ser Phe Thr Leu Trp
    210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
                245                 250                 255
Pro Glu Glu Phe His Gln Arg Ser Asn Val Thr Leu Thr Leu Arg Asn
            260                 265                 270
Leu Lys Gly Cys Cys Arg His Gln Val Gln Ile Gln Pro Phe Phe Ser
        275                 280                 285
Ser Cys Leu Asn Asp Cys Leu Arg His Ser Ala Thr Val Ser Cys Pro
    290                 295                 300
Glu Met Pro Asp Thr Pro Glu Pro Ile Pro Asp Tyr Met Pro Leu Trp
305                 310                 315                 320
Val Tyr Trp Phe Ile Thr Gly Ile Ser Ile Leu Leu Val Gly Ser Val
                325                 330                 335
Ile Leu Leu Ile Val Cys Met Thr Trp Arg Leu Ala Gly Pro Gly Ser
            340                 345                 350
Glu Lys Tyr Ser Asp Asp Thr Lys Tyr Thr Asp Gly Leu Pro Ala Ala
        355                 360                 365
Asp Leu Ile Pro Pro Pro Leu Lys Pro Arg Lys Val Trp Ile Ile Tyr
    370                 375                 380
Ser Ala Asp His Pro Leu Tyr Val Asp Val Val Leu Lys Phe Ala Gln
385                 390                 395                 400
Phe Leu Leu Thr Ala Cys Gly Thr Glu Val Ala Leu Asp Leu Leu Glu
                405                 410                 415
Glu Gln Ala Ile Ser Glu Ala Gly Val Met Thr Trp Val Gly Arg Gln
            420                 425                 430
Lys Gln Glu Met Val Glu Ser Asn Ser Lys Ile Ile Val Leu Cys Ser
        435                 440                 445
```

```
Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
                500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Glu Val Phe Glu Glu
        595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Val Glu Pro Gly Pro Leu Ala Asp
        675                 680                 685

Gly Ala Ala Val Arg Leu Ala Leu Ala Gly Glu Gly Glu Ala Cys Pro
        690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
                740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
                820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
850                 855                 860
```

Ser Ala
865

<210> SEQ ID NO 306
<211> LENGTH: 3710
<212> TYPE: DNA
<213> ORGANISM: Homo sapiens

<400> SEQUENCE: 306

| | | | | | |
|---|---|---|---|---|---|
| gggtctccgc | gcccaggaaa | gccccgcgcg | gcgcgggcca | gggaagggcc | acccaggggt | 60 |
| cccccacttc | ccgcttgggc | gcccggacgg | cgaatggagc | aggggcgcgc | agataattaa | 120 |
| agatttacac | acagctggaa | gaaatcatag | agaagccggg | cgtggtggct | catgcctata | 180 |
| atcccagcac | ttttggaggc | tgaggcgggc | agatcacttg | agatcaggag | ttcgagacca | 240 |
| gcctggtgcc | ttggcatctc | caatgggggt | ggctttgctc | tgggctcctg | ttccctgtga | 300 |
| gctgctggt | cctgctgcag | gtggcaagct | ctgggaacat | gaaggtcttg | caggagccca | 360 |
| cctgcgtctc | cgactacatg | agcatctcta | cttgcgagtg | aagatgaat | ggtcccacca | 420 |
| attgcagcac | cgagctccgc | ctgttgtacc | agctggtttt | tctgctctcc | gaagcccaca | 480 |
| cgtgtatccc | tgagaacaac | ggaggcgcgg | ggtgcgtgtg | ccacctgctc | atggatgacg | 540 |
| tggtcagtgc | ggataactat | acactggacc | tgtgggctgg | gcagcagctg | ctgtggaagg | 600 |
| gctccttcaa | gcccagcgag | catgtgaaac | ccagggcccc | aggaaacctg | acagttcaca | 660 |
| ccaatgtctc | cgacactctg | ctgctgacct | ggagcaaccc | gtatcccccct | gacaattacc | 720 |
| tgtataatca | tctcacctat | gcagtcaaca | tttggagtga | aaacgacccg | gcagatttca | 780 |
| gaatctataa | cgtgacctac | ctagaaccct | ccctccgcat | cgcagccagc | accctgaagt | 840 |
| ctgggatttc | ctacagggca | cgggtgaggg | cctgggctca | gtgctataac | accacctgga | 900 |
| gtgagtggag | ccccagcacc | aagtggcaca | actcctacag | ggagcccttc | gagcagcacc | 960 |
| tcctgctggg | cgtcagcgtt | cctgcattg | tcatcctggc | cgtctgcctg | ttgtgctatg | 1020 |
| tcagcatcac | caagattaag | aaagaatggt | gggatcagat | tcccaaccca | gcccgcagcc | 1080 |
| gcctcgtggc | tataataatc | caggatgctc | agggtcaca | gtgggagaag | cggtcccgag | 1140 |
| gccaggaacc | agccaagtgc | ccacactgga | agaattgtct | taccaagctc | ttgccctgtt | 1200 |
| ttctggagca | caacatgaaa | agggatgaag | atcctcacaa | ggctgccaaa | gagatgcctt | 1260 |
| tccagggctc | tgaaaatca | gcatggtgcc | cagtggagat | cagcaagaca | gtcctctggc | 1320 |
| cagagagcat | cagcgtggtg | cgatgtgtgg | agttgtttga | ggccccggtg | gagtgtgagg | 1380 |
| aggaggagga | ggtagaggaa | gaaaaaggga | gcttctgtgc | atcgcctgag | agcagcaggg | 1440 |
| atgacttcca | ggagggaagg | gagggcattg | tggcccggct | aacagagagc | ctgttcctgg | 1500 |
| acctgctcgg | agaggagaat | gggggcttttt | gccagcagga | catgggggag | tcatgccttc | 1560 |
| ttccaccttc | gggaagtacg | agtgctcaca | tgccctggga | tgagttccca | agtgcagggc | 1620 |
| ccaaggaggc | acctcctgg | ggcaaggagc | agcctctcca | cctggagcca | agtcctcctg | 1680 |
| ccagcccgac | ccagagtcca | gacaacctga | cttgcacaga | gacgccctc | gtcatcgcag | 1740 |
| gcaaccctgc | ttaccgcagc | ttcagcaact | ccctgagcca | gtcaccgtgt | cccagagagc | 1800 |
| tgggtccaga | cccactgctg | gccagacacc | tggaggaagt | agaacccgag | atgccctgtg | 1860 |
| tcccccagct | ctctgagcca | accactgtgc | cccaacctga | gccagaaacc | tgggagcaga | 1920 |
| tcctccgccg | aaatgtcctc | cagcatgggg | cagctgcagc | cccgtctcg | gcccccacca | 1980 |
| gtggctatca | ggagtttgta | catgcggtgg | agcagggtgg | cacccaggcc | agtgcggtgg | 2040 |

| | | | |
|---|---|---|---|
| tgggcttggg | tcccccagga | gaggctggtt acaaggcctt | ctcaagcctg cttgccagca | 2100 |
| gtgctgtgtc | cccagagaaa | tgtgggtttg gggctagcag | tggggaagag gggtataagc | 2160 |
| cttttccaaga | cctcattcct | ggctgccctg ggaccctgc | cccagtccct gtccccttgt | 2220 |
| tcacctttgg | actggacagg | gagccacctc gcagtccgca | gagctcacat ctcccaagca | 2280 |
| gctccccaga | gcacctgggt | ctggagccgg gggaaaaggt | agaggacatg ccaaagcccc | 2340 |
| cacttcccca | ggagcaggcc | acagacccc ttgtggacag | cctgggcagt ggcattgtct | 2400 |
| actcagccct | tacctgccac | ctgtgcggcc acctgaaaca | gtgtcatggc caggaggatg | 2460 |
| gtggccagac | ccctgtcatg | gccagtcctt gctgtggctg | ctgctgtgga dacaggtcct | 2520 |
| cgccccctac | aaccccctg | agggcccag accctctcc | aggtggggtt ccactggagg | 2580 |
| ccagtctgtg | tccggcctcc | ctggcaccct cgggcatctc | agagaagagt aaatcctcat | 2640 |
| catccttcca | tcctgcccct | ggcaatgctc agagctcaag | ccagaccccc aaaatcgtga | 2700 |
| actttgtctc | cgtgggaccc | acatacatga gggtctctta | ggtgcatgtc ctcttgttgc | 2760 |
| tgagtctgca | gatgaggact | agggcttatc catgcctggg | aaatgccacc tcctggaagg | 2820 |
| cagccaggct | ggcagatttc | caaaagactt gaagaaccat | ggtatgaagg tgattggccc | 2880 |
| cactgacgtt | ggcctaacac | tgggctgcag agactggacc | ccgcccagca ttgggctggg | 2940 |
| ctcgccacat | cccatgagag | tagagggcac tgggtcgccg | tgccccacgg caggcccctg | 3000 |
| caggaaaact | gaggcccttg | gcacctcga cttgtgaacg | agttgttggc tgctccctcc | 3060 |
| acagcttctg | cagcagactg | tccctgttgt aactgcccaa | ggcatgtttt gcccaccaga | 3120 |
| tcatggccca | cgtggaggcc | cacctgcctc tgtctcactg | aactagaagc cgagcctaga | 3180 |
| aactaacaca | gccatcaagg | gaatgacttg gcggccttg | ggaaatcgat gagaaattga | 3240 |
| acttcaggga | gggtggtcat | tgcctagagg tgctcattca | tttaacagag cttccttagg | 3300 |
| ttgatgctgg | aggcagaatc | ccggctgtca agggtgttc | agttaagggg agcaacagag | 3360 |
| gacatgaaaa | attgctatga | ctaaagcagg gacaatttgc | tgccaaacac ccatgcccag | 3420 |
| ctgtatggct | gggggctcct | cgtatgcatg gaaccccag | aataaatatg ctcagccacc | 3480 |
| ctgtgggccg | gcaatccag | acagcaggca taaggcacca | gttaccctgc atgttggccc | 3540 |
| agacctcagg | tgctagggaa | ggcgggaacc ttgggttgag | taatgctcgt ctgtgtgttt | 3600 |
| tagtttcatc | acctgttatc | tgtgtttgct gaggagagtg | gaacagaagg ggtggagttt | 3660 |
| tgtataaata | aagtttcttt | gtctctttaa aaaaaaaaa | aaaaaaaaa | 3710 |

<210> SEQ ID NO 307
<211> LENGTH: 1498
<212> TYPE: DNA
<213> ORGANISM: Homo sapiens

<400> SEQUENCE: 307

| | | | |
|---|---|---|---|
| accaaacctc | ttcgaggcac | aaggcacaac aggctgctct | gggattctct tcagccaatc | 60 |
| ttcattgctc | aagtgtctga | agcagccatg gcagaagtac | ctgagctcgc cagtgaaatg | 120 |
| atggcttatt | acagtggcaa | tgaggatgac ttgttctttg | aagctgatgg ccctaaacag | 180 |
| atgaagtgct | ccttccagga | cctggacctc tgccctctgg | atggcggcat ccagctacga | 240 |
| atctccgacc | accactacag | caagggcttc aggcaggccg | cgtcagttgt tgtggccatg | 300 |
| gacaagctga | ggaagatgct | ggttccctgc ccacagacct | tccaggagaa tgacctgagc | 360 |
| accttctttc | ccttcatctt | tgaagaagaa cctatcttct | tcgacacatg ggataacgag | 420 |
| gcttatgtgc | acgatgcacc | tgtacgatca ctgaactgca | cgctccggga ctcacagcaa | 480 |

```
aaaagcttgg tgatgtctgg tccatatgaa ctgaaagctc tccacctcca gggacaggat    540
atggagcaac aagtggtgtt ctccatgtcc tttgtacaag gagaagaaag taatgacaaa    600
atacctgtgg ccttgggcct caaggaaaag aatctgtacc tgtcctgcgt gttgaaagat    660
gataagccca ctctacagct ggagagtgta gatcccaaaa attacccaaa gaagaagatg    720
gaaaagcgat ttgtcttcaa caagatagaa atcaataaca agctggaatt tgagtctgcc    780
cagttcccca actggtacat cagcacctct caagcagaaa acatgccgt cttcctggga    840 gggaccaaag gcggccagga tataactgac ttcaccatgc aatttgtgtc ttcctaaaga    900
gagctgtacc cagagagtcc tgtgctgaat gtggactcaa tccctagggc tggcagaaag    960
ggaacagaaa ggttttgag tacggctata gcctggactt tcctgttgtc tacaccaatg   1020
cccaactgcc tgccttaggg tagtgctaag aggatctcct gtccatcagc caggacagtc   1080
agctctctcc tttcagggcc aatccccagc cctttgttg agccaggcct ctctcacctc   1140
tcctactcac ttaaagcccg cctgacagaa accacggcca catttggttc taagaaaccc   1200
tctgtcattc gctcccacat tctgatgagc aaccgcttcc ctatttattt atttatttgt   1260
ttgtttgttt tattcattgg tctaatttat tcaaggggg caagaagtag cagtgtctgt    1320
aaaagagcct agtttttaat agctatggaa tcaattcaat ttggactggt gtgctctctt   1380
taaatcaagt cctttaatta agactgaaaa tatataagct cagattattt aaatgggaat   1440
atttataaat gagcaaatat catactgttc aatggttctg aaataaactt cactgaag    1498

<210> SEQ ID NO 308
<211> LENGTH: 2358
<212> TYPE: DNA
<213> ORGANISM: Homo sapiens

<400> SEQUENCE: 308
aaactcacac aacaactctt ccccgctgag aggagacagc cagtgcgact ccaccctcca     60
gctcgacggc agccgccccg ccgacagcc ccgagacgac agcccggcgc gtcccggtcc    120
ccacctccga ccaccgccag cgctccaggc cccgccgctc cccgctcgcc gccaccgcgc    180
cctccgctcc gcccgcagtg ccaaccatga ccgccgccag tatgggcccc gtccgcgtcg    240
ccttcgtggt cctcctcgcc ctctgcagcc ggccggccgt cggccagaac tgcagcgggc    300
cgtgccggtg cccggacgag ccggcgccgc gctgcccggc gggcgtgagc ctcgtgctgg    360
acggctgcgg ctgctgccgc gtctgcgcca gcagctgggg cgagctgtgc accgagcgcg    420
acccctgcga cccgcacaag ggcctcttct gtgacttcgg ctccccggcc aaccgcaaga    480
tcggcgtgtg caccgccaaa gatggtgctc cctgcatctt cggtggtacg gtgtaccgca    540
gcggagagtc cttccagagc agctgcaagt accagtgcac gtgcctggac ggggcggtgg    600
gctgcatgcc cctgtgcagc atggacgttc gtctgcccag ccctgactgc cccttcccga    660
ggagggtcaa gctgcccggg aaatgctgcg aggagtgggt gtgtgacgag cccaaggacc    720
aaaccgtggt tgggcctgcc ctcgcggctt accgactgga agacacgttt ggcccagacc    780
caactatgat tagagccaac tgcctggtcc agaccacaga gtggagcgcc tgttccaaga    840
cctgtgggat gggcatctcc accgggtta ccaatgacaa cgcctcctgc aggctagaga    900
agcagagccg cctgtgcatg gtcaggcctt gcgaagctga cctggaagag aacattaaga    960
agggcaaaaa gtgcatccgt actcccaaaa tctccaagcc tatcaagttt gagctttctg   1020
gctgcaccag catgaagaca taccgagcta aattctgtgg agtatgtacc gacggccgat   1080
```

```
gctgcacccc ccacagaacc accaccctgc cggtggagtt caagtgccct gacggcgagg      1140
tcatgaagaa gaacatgatg ttcatcaaga cctgtgcctg ccattacaac tgtcccggag      1200
acaatgacat ctttgaatcg ctgtactaca ggaagatgta cggagacatg gcatgaagcc      1260
agagagtgag agacattaac tcattagact ggaacttgaa ctgattcaca tctcattttt      1320
ccgtaaaaat gatttcagta gcacaagtta tttaaatctg ttttttctaac tgggggaaaa    1380 gattcccacc caattcaaaa cattgtgcca tgtcaaacaa atagtctatc aaccccagac     1440
actggtttga agaatgttaa gacttgacag tggaactaca ttagtacaca gcaccagaat    1500
gtatattaag gtgtggcttt aggagcagtg ggagggtacc agcagaaagg ttagtatcat    1560
cagatagcat cttatacgag taatatgcct gctatttgaa gtgtaattga aaggaaaat     1620 tttagcgtgc tcactgacct gcctgtagcc ccagtgacag ctaggatgtg cattctccag    1680
ccatcaagag actgagtcaa gttgttcctt aagtcagaac agcagactca gctctgacat   1740
tctgattcga atgacactgt tcaggaatcg gaatcctgtc gattagactg gacagcttgt   1800
ggcaagtgaa tttgcctgta acaagccaga tttttttaaa tttatattgt aaatattgtg   1860
tgtgtgtgtg tgtgtgtata tatatatata tgtacagtta tctaagttaa tttaaagttg   1920
tttgtgcctt tttattttg ttttaatgc tttgatattt caatgttagc ctcaatttct     1980
gaacaccata ggtagaatgt aaagcttgtc tgatcgttca aagcatgaaa tggatactta   2040
tatggaaatt ctgctcagat agaatgacag tccgtcaaaa cagattgttt gcaaggggga   2100
ggcatcagtg tccttggcag gctgatttct aggtaggaaa tgtggtagcc tcactttaa    2160 tgaacaaatg gcctttatta aaaactgagt gactctatat agctgatcag tttttttcacc  2220 tggaagcatt tgtttctact ttgatatgac tgttttttcgg acagtttatt tgttgagagt   2280
gtgaccaaaa gttacatgtt tgcaccttc tagttgaaaa taaagtgtat attttttcta   2340
taaaaaaaaa aaaaaaaa                                                  2358

<210> SEQ ID NO 309
<211> LENGTH: 825
<212> TYPE: PRT
<213> ORGANISM: Homo sapiens

<400> SEQUENCE: 309

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140
```

```
Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
            165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
            195                 200                 205

Asn Thr Thr Trp Ser Glu Trp Ser Pro Ser Thr Lys Trp His Asn Ser
210                 215                 220

Tyr Arg Glu Pro Phe Glu Gln His Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
            260                 265                 270

Arg Leu Val Ala Ile Ile Gln Asp Ala Gln Gly Ser Gln Trp Glu
            275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
            340                 345                 350

Pro Glu Ser Ile Ser Val Val Arg Cys Val Glu Leu Phe Glu Ala Pro
            355                 360                 365

Val Glu Cys Glu Glu Glu Glu Val Glu Glu Lys Gly Ser Phe
    370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
            405                 410                 415

Glu Glu Asn Gly Gly Phe Cys Gln Gln Asp Met Gly Glu Ser Cys Leu
            420                 425                 430

Leu Pro Pro Ser Gly Ser Thr Ser Ala His Met Pro Trp Asp Glu Phe
            435                 440                 445

Pro Ser Ala Gly Pro Lys Glu Ala Pro Pro Trp Gly Lys Glu Gln Pro
    450                 455                 460

Leu His Leu Glu Pro Ser Pro Ala Ser Pro Thr Gln Ser Pro Asp
465                 470                 475                 480

Asn Leu Thr Cys Thr Glu Thr Pro Leu Val Ile Ala Gly Asn Pro Ala
            485                 490                 495

Tyr Arg Ser Phe Ser Asn Ser Leu Ser Gln Ser Pro Cys Pro Arg Glu
            500                 505                 510

Leu Gly Pro Asp Pro Leu Leu Ala Arg His Leu Glu Glu Val Glu Pro
            515                 520                 525

Glu Met Pro Cys Val Pro Gln Leu Ser Glu Pro Thr Thr Val Pro Gln
            530                 535                 540

Pro Glu Pro Glu Thr Trp Glu Gln Ile Leu Arg Arg Asn Val Leu Gln
545                 550                 555                 560

His Gly Ala Ala Ala Ala Pro Val Ser Ala Pro Thr Ser Gly Tyr Gln
```

```
                565                 570                 575
Glu Phe Val His Ala Val Glu Gln Gly Gly Thr Gln Ala Ser Ala Val
                580                 585                 590
Val Gly Leu Gly Pro Pro Gly Glu Ala Gly Tyr Lys Ala Phe Ser Ser
                595                 600                 605
Leu Leu Ala Ser Ser Ala Val Ser Pro Glu Lys Cys Gly Phe Gly Ala
            610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
                645                 650                 655
Leu Asp Arg Glu Pro Pro Arg Ser Pro Gln Ser Ser His Leu Pro Ser
                660                 665                 670
Ser Ser Pro Glu His Leu Gly Leu Glu Pro Gly Glu Lys Val Glu Asp
                675                 680                 685
Met Pro Lys Pro Pro Leu Pro Gln Glu Gln Ala Thr Asp Pro Leu Val
                690                 695                 700
Asp Ser Leu Gly Ser Gly Ile Val Tyr Ser Ala Leu Thr Cys His Leu
705                 710                 715                 720
Cys Gly His Leu Lys Gln Cys His Gly Gln Glu Asp Gly Gly Gln Thr
                725                 730                 735
Pro Val Met Ala Ser Pro Cys Cys Gly Cys Cys Cys Gly Asp Arg Ser
                740                 745                 750
Ser Pro Pro Thr Thr Pro Leu Arg Ala Pro Asp Pro Ser Pro Gly Gly
                755                 760                 765
Val Pro Leu Glu Ala Ser Leu Cys Pro Ala Ser Leu Ala Pro Ser Gly
                770                 775                 780
Ile Ser Glu Lys Ser Lys Ser Ser Ser Phe His Pro Ala Pro Gly
785                 790                 795                 800
Asn Ala Gln Ser Ser Ser Gln Thr Pro Lys Ile Val Asn Phe Val Ser
                805                 810                 815
Val Gly Pro Thr Tyr Met Arg Val Ser
                820                 825

<210> SEQ ID NO 310
<211> LENGTH: 269
<212> TYPE: PRT
<213> ORGANISM: Homo sapiens

<400> SEQUENCE: 310

Met Ala Glu Val Pro Glu Leu Ala Ser Glu Met Met Ala Tyr Tyr Ser
1               5                   10                  15
Gly Asn Glu Asp Asp Leu Phe Phe Glu Ala Asp Gly Pro Lys Gln Met
                20                  25                  30
Lys Cys Ser Phe Gln Asp Leu Asp Leu Cys Pro Leu Asp Gly Gly Ile
            35                  40                  45
Gln Leu Arg Ile Ser Asp His His Tyr Ser Lys Gly Phe Arg Gln Ala
        50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                85                  90                  95
Ile Phe Glu Glu Glu Pro Ile Phe Phe Asp Thr Trp Asp Asn Glu Ala
                100                 105                 110
```

```
Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 311
<211> LENGTH: 349
<212> TYPE: PRT
<213> ORGANISM: Homo sapiens

<400> SEQUENCE: 311

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220
```

-continued

```
Asn Ala Ser Cys Arg Leu Glu Lys Gln Ser Arg Leu Cys Met Val Arg
225                 230                 235                 240
Pro Cys Glu Ala Asp Leu Glu Glu Asn Ile Lys Lys Gly Lys Lys Cys
                245                 250                 255
Ile Arg Thr Pro Lys Ile Ser Lys Pro Ile Lys Phe Glu Leu Ser Gly
            260                 265                 270
Cys Thr Ser Met Lys Thr Tyr Arg Ala Lys Phe Cys Gly Val Cys Thr
        275                 280                 285
Asp Gly Arg Cys Cys Thr Pro His Arg Thr Thr Thr Leu Pro Val Glu
    290                 295                 300
Phe Lys Cys Pro Asp Gly Glu Val Met Lys Lys Asn Met Met Phe Ile
305                 310                 315                 320
Lys Thr Cys Ala Cys His Tyr Asn Cys Pro Gly Asp Asn Asp Ile Phe
                325                 330                 335
Glu Ser Leu Tyr Tyr Arg Lys Met Tyr Gly Asp Met Ala
            340                 345
```

LIPOSOMAL SPHERICAL NUCLEIC ACID (SNA) CONSTRUCTS PRESENTING ANTISENSE OLIGONUCLEOTIDES (ASO) FOR SPECIFIC KNOCKDOWN OF INTERLEUKIN 17 RECEPTOR MRNA

RELATED APPLICATIONS

This application is a national stage filing under 35 U.S.C. § 371 of International Patent Application Serial No. PCT/US2017/031428, entitled "LIPOSOMAL SPHERICAL NUCLEIC ACID (SNA) CONSTRUCTS PRESENTING ANTISENSE OLIGONUCLEOTIDES (ASO) FOR SPECIFIC KNOCKDOWN OF INTERLEUKIN 17 RECEPTOR MRNA" filed May 5, 2017, which claims the benefit under 35 U.S.C. § 119(e) of U.S. Provisional Application Ser. No. 62/333,082, entitled "LIPOSOMAL SPHERICAL NUCLEIC ACID (SNA) CONSTRUCTS PRESENTING ANTISENSE OLIGONUCLEOTIDES (ASO) FOR SPECIFIC KNOCKDOWN OF INTERLEUKIN 17 RECEPTOR MRNA", filed May 6, 2016, the entire contents of each of which are incorporated by reference herein.

BACKGROUND OF INVENTION

Inflammation, which can be classified as either acute or chronic, involves the activation of the immune system in response to harmful stimuli, such as, e.g., a pathogen, infection, irritant, or damage to cells. Acute inflammation is mediated by granulocytes, while chronic inflammation is mediated by mononuclear cells such as monocytes and lymphocytes.

The process of acute inflammation is initiated by cells such as macrophages, dendritic cells, histiocytes, Kupffer cells, mastocytes, vascular endothelial cells, and vascular smooth muscle cells. At the onset of a harmful stimulus, these cells undergo activation and release inflammatory mediating and sensitizing molecules, such as, e.g., pro-inflammatory cytokines, pro-inflammatory prostaglandins, leukotrienes, histamine, serotonin, neutral proteases, bradykinin and nitric oxide. These inflammatory molecules modulate a complex series of biological events involving cellular and acellular components of the local vascular system, the immune system, and the injured tissue site to propagate and mature the inflammatory response.

Severe or prolonged stimulation results in a chronic inflammatory response that leads to a progressive shift in the type of cells present at the site of tissue injury. Chronic inflammation may be characterized as the simultaneous destruction and healing of tissue from the inflammatory process, with the net result of provoking injury rather than mediating repair. As an inflammatory response can occur anywhere in the body, chronic inflammation has been implicated in the pathophysiology of a wide range of seemingly unrelated disorders which underlay a large and varied group of human diseases. For example, chronic inflammation is involved in diseases as diverse as psoriasis, cardiovascular diseases, cancers, allergies, obesity, diabetes, digestive system diseases, degenerative diseases, auto-immune disorders, and Alzheimer's disease.

SUMMARY OF INVENTION

The present disclosure, in some aspects, includes a single-stranded modified oligonucleotide consisting of 10-30 linked nucleosides and having: a gap segment consisting of two to eight linked deoxynucleosides; a 5' wing segment consisting of linked nucleosides; and a 3' wing segment consisting of linked nucleosides; wherein the gap segment is positioned between the 5' wing segment and the 3' wing segment; wherein at least some nucleosides of each wing segment comprises a modified nucleotide; wherein the internucleoside linkages within the gap segment and the linkages connecting the gap segment to the 3' wing segments are all phosphorothioate linkages (*); and the internucleoside linkages connecting the rest of the nucleosides of both the 5' and 3' wing segments are phosphodiester linkages; and wherein the nucleobase sequence of the oligonucleotide consists of 10-30 contiguous nucleobases complementary to an equal length portion of SEQ ID NO: 302, or a pharmaceutically acceptable salt thereof.

In some embodiments the single-stranded modified oligonucleotide consists of 17-21 linked nucleosides. In other embodiments the gap segment consists of six linked deoxynucleosides. In yet other embodiments wherein each nucleoside of each wing segment comprises a modified nucleotide. In other embodiments the modified nucleotide is 2'O-methyl ribonucleoside (m). The oligonucleotide has 12 2'O-methyl ribonucleosides in other embodiments. In some embodiments the nucleobase sequence of the oligonucleotide consists of 17-21 contiguous nucleobases complementary to an equal length portion of SEQ ID NO: 302.

In one embodiment, the nucleobase sequence of the oligonucleotide is GCUUGGGCAGGTGGUGAA (SEQ ID NO: 225). In another embodiment, the nucleobase sequence of the oligonucleotide is CCCACAGGGGCATGUAGU (SEQ ID NO: 288). An additional embodiment includes an oligonucleotide with the nucleobase sequence of GUAGGGCGUGTGTGGGUC (SEQ ID NO: 291). In another embodiment, the nucleobase sequence of the oligonucleotide is mGmCmUmUmGmGG*C*A*G*G*T*mGmGmUmGmAmA (SEQ ID NO: 225). In a further embodiment, the nucleobase sequence of the oligonucleotide is mCmCmCmAmCmAmGG*G*G*C*A*T* mGmUmAmGmU (SEQ ID NO: 288). In yet another embodiment, the nucleobase sequence of the oligonucleotide is (SEQ ID NO: 291)
mGmUmAmGmGmGmCmGmUG*T*G*T*G*mGmUmC.

In some embodiments, the compound is 20 nucleotides in length.

In some embodiments, the oligonucleotide further comprises a molecular species at one of the ends. In another embodiment, the compound further comprises a molecular species at both ends.

In some embodiments, the molecular species is selected from the group consisting of a spacer, a lipid, a sterol, cholesterol, NAcetylgalactosamine (GalNAc), modified GalNAc, derivatized or substituted GalNAc, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, and ibuprofen.

In other embodiments, the molecular species is selected from the group consisting of a lipophilic moiety; a folic acid radical; a steroid radical; a carbohydrate radical; a vitamin A radical; a vitamin E radical; or a vitamin K radical.

In some embodiments, the molecular species is connected directly to the compound through a linkage selected from the group consisting of phosphodiester, phosphorothioate, phosphorodithioate, methylphosphonate, and amide linkages.

In another embodiment, the molecular species is connected indirectly to the compound through a linker. In some embodiments, the linker is a non-nucleotidic linker selected from the group consisting of abasic residues (dSpacer), oligoethyleneglycol, such as triethyleneglycol (spacer 9) or hexaethylenegylcol (spacer 18), and alkane-diol, such as butanediol.

In some embodiments, the 3' end of the oligonucleotide is connected to 2 consecutive linkers that are hexaethylenegylcol (spacer 18), the first hexaethylenegylcol connected to the 3' end of the oligonucleotide, the second hexaethylenegylcol connected to the first hexaethylenegylcol and the second hexaethylenegylcol is connected to a cholesterol.

Another aspect of the present disclosure includes an oligonucleotide comprising mGmCmUmUmGmGG*C*A*G*G*T*mGmGmUmGmAmA/isp18//isp18//3CholTEG/(SEQ ID NO: 225), wherein the oligonucleotide is 20 nucleotides in length, wherein m is a 2'O methyl, and wherein * is a phosphorothioate modification.

An additional aspect of the present disclosure includes an oligonucleotide comprising mCmCmCmAmCmAmGG*G*G*C*A*T*mGmUmAmGmU/isp18//isp18//3CholTEG/.

(SEQ ID NO: 288), wherein the oligonucleotide is 20 nucleotides in length, wherein m is a 2'O methyl, and wherein * is a phosphorothioate modification.

A further aspect of the present disclosure includes an oligonucleotide comprising mGmUmAmGmGmGmCmGmUG*T*G*T*G*G*mGmUmC/isp18//isp18//3CholTEG/(SEQ ID NO: 291), wherein the oligonucleotide is 20 nucleotides in length, wherein m is a 2'O methyl, and wherein * is a phosphorothioate modification.

Another aspect of the present disclosure includes a stable self-assembling nanostructure, comprising a core having an oligonucleotide shell comprised of an antisense oligonucleotide 18 to 21 linked nucleosides in length targeted to Interleukin 17 receptor (IL-17R, IL-17RA) positioned on the exterior of the core. In some embodiments, the antisense oligonucleotide is 18 nucleotides in length. In other embodiments, IL-17RA has a sequence of SEQ ID NO: 302.

In another embodiment, less than all of the internucleoside linkages are phosphodiester. In some embodiments, the antisense oligonucleotide has phosphorothioate internucleoside linkages. In other embodiments, less than all of the internucleoside linkages are phosphorothioate. In another embodiment, the oligonucleotides have at least one internucleoside phosphorothioate linkage that is stereo-enriched. In another embodiment, the oligonucleotides have all the internucleoside phosphorothioate linkage that are stereo-enriched. The stereo-enriched phosphorothioate linkage may be Rp diastereomer, or Sp diastereomer.

In some embodiments, the antisense oligonucleotide has 2'O methyl modifications. In other embodiments, less than all of the nucleotides include a 2'O methyl modification.

In some embodiments, the antisense oligonucleotide has 2'O alkyl modifications. In other embodiments, less than all of the nucleotides include a 2'O alkyl modification.

In some embodiments, the antisense oligonucleotide has 17 internucleoside linkages and 6 central internucleoside linkages are phosphorothioate.

In some embodiments, the antisense oligonucleotide has a nucleobase sequence complementary to a sequence comprising at least 8 contiguous nucleobases of a sequence recited in SEQ ID NO: 302. In other embodiments, the antisense oligonucleotide is selected from the group consisting of mGmCmUmUmGmGG*C*A*G*G*T*mGmGmUmGmAmA/isp18//isp18//3CholTEG/(SEQ ID NO: 225);

mCmCmCmAmCmAmGG*G*G*C*A*T*mGmUmAmGmU/isp18//isp18//3CholTEG/(SEQ ID NO: 288); and mGmUmAmGmGmGmCmGmUG*T*G*T*G*G*mGmUmC/isp18//isp18//3CholTEG/(SEQ ID NO: 291)
wherein—refers to a phosphodiester bond, * refers to a phosphorothioate bond, and m refers to a O methyl.

In some embodiments, the nanostructure includes 2-1,000 copies of the antisense oligonucleotide. In other embodiments, the nanostructure includes at least two different antisense oligonucleotides.

In some embodiments, the core is a solid or hollow core. In other embodiments, the core is a solid core and further comprising a lipid bilayer surrounding the core. In another embodiment, the solid core is comprised of noble metals, including gold and silver, transition metals including iron and cobalt, metal oxides including silica, polymers or combinations thereof. In some embodiments, the core is a polymeric core and wherein the polymeric core is comprised of amphiphilic block copolymers, hydrophobic polymers including polystyrene, poly(lactic acid), poly(lactic co-glycolic acid), poly(glycolic acid), poly(caprolactone) and other biocompatible polymers.

In other embodiments, the core is a liposomal core. In some embodiments, the liposomal core is comprised of one or more lipids selected from: 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE), sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and derivatives thereof.

The present disclosure, in some aspects, includes a multiplex antisense oligonucleotide spherical nucleic acid (mASO-SNA), comprising a core having an oligonucleotide shell comprised of an antisense oligonucleotide 10 to 30 linked nucleosides in length targeted to a first gene and an antisense oligonucleotide 10 to 30 linked nucleosides in length targeted to a second gene, wherein the core is a solid surrounded by a lipid bilayer or a liposome or lipoplex complex core and the oligonucleotide shell is positioned on the exterior of the core.

In some embodiments, the first gene and the second gene are associated with a disease. In an embodiment, the disease is an inflammatory disorder. In another embodiment, the disease is psoriasis.

In some embodiments, the first gene and the second gene are associated with a target pathway.

In another embodiment, the mASO-SNA further comprises an antisense oligonucleotide 10 to 30 linked nucleosides in length targeted to a third gene. In some embodiments, the first gene is an Interleukin 17 receptor (IL-17RA). In other embodiments, the second gene is TNF. In some embodiments, the first gene and the second gene are present in an approximate equimolar amount in the oligonucleotide shell.

In another embodiment, the mASO-SNA comprises an antisense oligonucleotide 10 to 30 linked nucleosides in length targeted to four or more genes.

The present disclosure, in some aspects, provides a method for treating a disorder, comprising: administering to a subject having a disorder a multiplex antisense oligonucleotide spherical nucleic acid (mASO-SNA), comprising a core having an oligonucleotide shell comprised of an antisense oligonucleotide 10 to 30 linked nucleosides in length targeted to a first gene and an antisense oligonucleotide 10 to 30 linked nucleosides in length targeted to a second gene, wherein the core is a solid surrounded by a lipid bilayer or a liposome or lipoplex complex core and the oligonucleotide shell is positioned on the exterior of the core in an effective amount to treat the disorder.

In some embodiments, the disorder is an inflammatory disorder.

In other embodiments, the mASO-SNA produces simultaneous mRNA knock-down of the first and second gene. In another embodiment, the first gene and the second gene are associated with a target pathway. In some embodiments, the mASO-SNA produces additive knock-down of the target pathway.

In other embodiments, the disorder is psoriasis.

Another aspect of the present disclosure provides a method for treating an inflammatory disorder, including administering to a subject having an inflammatory disorder a composition comprising the oligonucleotide or the nanostructure described herein in an effective amount to treat the inflammatory disorder.

In some embodiments, the inflammatory disorder is selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In other embodiments, the inflammatory disorder is selected from the group consisting of rheumatoid arthritis, rheumatoid spondylitis, osteoarthritis, gouty arthritis, allergy, multiple sclerosis, autoimmune diabetes, autoimmune uveitis, and nephritic syndrome.

An additional aspect of the present disclosure includes a method for reducing expression levels of IL-17 receptor in vivo, including administering to a subject a composition comprising the oligonucleotide or the nanostructure described herein in an effective amount to reduce IL-17 receptor levels in vivo.

In some embodiments, the first gene, the second gene, and the third gene are associated with a target pathway. In some embodiments, the first gene and the second gene are associated with different target pathways. In some embodiments, the first gene, the second gene and the third gene are associated with different target pathways. In some embodiments, the first gene is an interleukin-4 receptor (IL-4R). In some embodiments, the second gene is interleukin-1 beta (IL-1β). In some embodiments, the third gene is connective tissue growth factor (CTGF).

In some embodiments, the first gene, the second gene, and the third gene are present in an approximate equimolar amount in the oligonucleotide shell.

According to another aspect, pharmaceutical compositions are provided herein. In some embodiments, the pharmaceutical composition includes a stable self-assembling nanostructure, wherein the self-assembling nanostructure comprises a core having an oligonucleotide shell comprised of an antisense oligonucleotide 18 to 21 linked nucleosides in length targeted to interleukin 17 receptor (IL-17R) positioned on the exterior of the core.

In some embodiments, the antisense oligonucleotide is 18 nucleotides in length. In some embodiments, the IL-17R has a sequence of SEQ ID NO: 302.

In some embodiments, less than all of the internucleoside linkages are phosphodiester. In some embodiments, the antisense oligonucleotide has phosphorothioate internucleoside linkages. In some embodiments, less than all of the internucleoside linkages are phosphorothioate.

In some embodiments, the antisense oligonucleotide has 2'O methyl modifications. In some embodiments, less than all of the nucleotides include a 2'O methyl modification.

In some embodiments, the antisense oligonucleotide has 17 internucleoside linkages and wherein 6 central internucleoside linkages are phosphorothioate. In some embodiments, the antisense oligonucleotide has a nucleobase sequence complementary to a sequence including at least 8 contiguous nucleobases of a sequence recited in SEQ ID NO: 302.

In some embodiments, the antisense oligonucleotide is selected from the group consisting of
  mGmCmUmUmGmGG*C*A*G*G*T*mGmGmUmGm
    AmA/isp18//isp18//3CholTEG/(SEQ ID NO: 225);
  mCmCmCmAmCmAmGG*G*G*C*A*T*mGmUmAm
    GmU/isp18//isp18//3CholTEG/(SEQ ID NO: 288); and
  mGmUmAmGmGmGmCmGmUG*T*G*T*G*G*mGm
    UmC/isp18//isp18//3CholTEG/(SEQ ID NO: 291)
    wherein—refers to a phosphodiester bond, * refers to a phosphorothioate bond, and m refers to a O methyl.

In some embodiments, the pharmaceutical composition includes a gel vehicle. In some embodiments, the pharmaceutical composition includes one or more of 1,2-dioleoyl-sn-glycero-3-phosphocholine (DOPC), diethylene glycol monoethyl ether (Transcutol P), glycerin, hydroxyethyl cellulose, methylparaben, propylparaben, disodium EDTA, sodium metabisulfite and water. In certain embodiments, the pharmaceutical composition includes at least 0.00007% mCmCmCmAmCmAmGG*G*G*C*A*T*mGmUmAm GmU/isp18//isp18//3CholTEG/(SEQ ID NO: 288), at least 0.0003801% DOPC, at least 25% diethylene glycol monoethyl ether (Transcutol P), at least 5% glycerin, at least 1% hydroxyethyl cellulose, at least 0.15% methylparaben, at least 0.05% propylparaben, at least 0.1% disodium EDTA, at least 0.2% sodium metabisulfite, and at least 68.5% water.

In some embodiments, the pharmaceutical composition includes at least 0.007% mCmCmCmAmCmAmGG*G* G*C*A*T*mGmUmAmGmU/isp18//isp18//3CholTEG/ (SEQ ID NO: 288), at least 0.03801% DOPC, at least 25% diethylene glycol monoethyl ether (Transcutol P), at least 5% glycerin, at least 1% hydroxyethyl cellulose, at least 0.15% methylparaben, at least 0.05% propylparaben, at least 0.1% disodium EDTA, at least 0.2% sodium metabisulfite, and at least 68.45% water.

In some embodiments, the pharmaceutical composition comprises at least 0.01419% mCmCmCmAmCmAmGG* G*G*C*A*T*mGmUmAmGmU/isp18//isp18//3CholTEG/ (SEQ ID NO: 288), at least 0.2655% DOPC, at least 25% diethylene glycol monoethyl ether (Transcutol P), at least 5% glycerin, at least 1% hydroxyethyl cellulose, at least 0.15% methylparaben, at least 0.05% propylparaben, at least 0.1% disodium EDTA, at least 0.2% sodium metabisulfite, and at least 68.2% water.

In some embodiments, the pharmaceutical composition comprises at least 0.1419% mCmCmCmAmCmAmGG* G*G*C*A*T*mGmUmAmGmU/isp18//isp18//3CholTEG/ (SEQ ID NO: 288), at least 2.655% DOPC, at least 25% diethylene glycol monoethyl ether (Transcutol P), at least 5% glycerin, at least 1% hydroxyethyl cellulose, at least 0.15% methylparaben, at least 0.05% propylparaben, at least 0.1% disodium EDTA, at least 0.2% sodium metabisulfite, and at least 65.7% water.

In some embodiments, the pharmaceutical composition comprises at least 1.419% mCmCmCmAmCmAmGG* G*G*C*A*T*mGmUmAmGmU/isp18//isp18//3CholTEG/ (SEQ ID NO: 288), at least 26.55% DOPC, at least 25% diethylene glycol monoethyl ether (Transcutol P), at least 5% glycerin, at least 1% hydroxyethyl cellulose, at least 0.15% methylparaben, at least 0.05% propylparaben, at least 0.1% disodium EDTA, at least 0.2% sodium metabisulfite, and at least 40.5% water.

In some embodiments, the pharmaceutical composition includes an oligonucleotide described herein.

In some embodiments, the pharmaceutical composition further includes a gel vehicle. In some embodiments, the pharmaceutical composition includes one or more of 1,2-dioleoyl-sn-glycero-3-phosphocholine (DOPC), diethylene glycol monoethyl ether (Transcutol P), glycerin, hydroxyethyl cellulose, methylparaben, propylparaben, disodium EDTA, sodium metabisulfite and water.

In some embodiments, the pharmaceutical composition includes a mASO-SNA described herein.

In some embodiments, the pharmaceutical composition further includes a gel vehicle. In some embodiments, the pharmaceutical composition comprises one or more of 1,2-dioleoyl-sn-glycero-3-phosphocholine (DOPC), diethylene glycol monoethyl ether (Transcutol P), glycerin, hydroxyethyl cellulose, methylparaben, propylparaben, disodium EDTA, sodium metabisulfite and water.

According to another aspect, methods for treating a disorder using a pharmaceutical composition are also disclosed herein. In some embodiments, a method for treating a disorder comprises administering to a subject having a disorder a pharmaceutical composition including a multiplex antisense oligonucleotide spherical nucleic acid (mASO-SNA), including a core having an oligonucleotide shell comprised of an antisense oligonucleotide 10 to 30 linked nucleosides in length targeted to a first gene and an antisense oligonucleotide 10 to 30 linked nucleosides in length targeted to a second gene, wherein the core is a solid surrounded by a lipid bilayer or a liposome or lipoplex complex core and the oligonucleotide shell is positioned on the exterior of the core in an effective amount to treat the disorder.

In some embodiments, the pharmaceutical composition further comprises a gel vehicle. In some embodiments, the pharmaceutical composition comprises one or more of 1,2-dioleoyl-sn-glycero-3-phosphocholine (DOPC), diethylene glycol monoethyl ether (Transcutol P), glycerin, hydroxyethyl cellulose, methylparaben, propylparaben, disodium EDTA, sodium metabisulfite and water.

In some embodiments, the disorder is an inflammatory disorder.

In some embodiments, the mASO-SNA produces simultaneous mRNA knock-down of the first and second gene. In some embodiments, the first gene and the second gene are associated with a target pathway. In some embodiments, the mASO-SNA produces additive knock-down of the target pathway.

In some embodiments, the disorder is psoriasis.

According to another aspect, methods for treating an inflammatory disorder using a pharmaceutical composition are also disclosed herein. In some embodiments, a method for treating an inflammatory disorder includes administering to a subject having an inflammatory disorder a pharmaceutical composition including an oligonucleotide, a nanostructure or a mASO-SNA described herein in an effective amount to treat the inflammatory disorder.

In some embodiments, the pharmaceutical composition further includes a gel vehicle. In some embodiments, the pharmaceutical composition includes one or more of 1,2-dioleoyl-sn-glycero-3-phosphocholine (DOPC), diethylene glycol monoethyl ether (Transcutol P), glycerin, hydroxyethyl cellulose, methylparaben, propylparaben, disodium EDTA, sodium metabisulfite and water.

In some embodiments, the inflammatory disorder is selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In some embodiments, the inflammatory disorder is selected from the group consisting of rheumatoid arthritis, rheumatoid spondylitis, osteoarthritis, gouty arthritis, allergy, multiple sclerosis, autoimmune diabetes, autoimmune uveitis, and nephritic syndrome.

According to another aspect, methods for reducing expression of the IL-17 receptor in vivo are provided herein. In some embodiments, the method for reducing expression levels of IL-17 receptor in vivo includes administering to a subject a pharmaceutical composition including an oligonucleotide, a nanostructure, or a mASO-SNA described herein in an effective amount to reduce IL-17 receptor levels in vivo.

In some embodiments, the subject is a mammal. In some embodiments, the subject is human.

In some embodiments, the pharmaceutical composition is in contact with a cell in the subject for at least 24 hours.

In some embodiments, the pharmaceutical composition is a topical pharmaceutical composition.

According to another aspect, methods for reducing expression levels of IL-17 receptor (IL-17R) in vitro are provided herein.

In some embodiments, the method for reducing expression levels of IL-17R in vitro includes contacting a cell with an oligonucleotide, a nanostructure, or a mASO-SNA described herein in an effective amount to reduce IL-17R levels in vitro.

In some embodiments, the cell is a human foreskin keratinocyte (HFK).

In some embodiments, the cell is contacted with the oligonucleotide, the nanostructure, or the mASO-SNA at a concentration of 1 nM, 10 nM, 100 nM, or 1000 nM.

In some embodiments, the cell is contacted with the oligonucleotide, the nanostructure, or the mASO-SNA for 24 hours.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 5 shows IL17RA mRNA knockdown using a mixture of SNAs. IL17RA mRNA expression is decreased in HFK cells treated with a mixture of anti-TNF-SNAs and anti-IL17RA-SNAs. Cells treated with Control-SNAs do not demonstrate an appreciable decrease in TNF mRNA levels. Data shown are representative of two independent experiments performed.

(FIG. 6A) 33% TNF-ASO (A) and 66% control (D); (FIG. 6B) 33% IL17RA-ASO (B) and 66% control (D); (FIG. 6C) 33% TNF-ASO (A), 33% IL17RA-ASO (B), and 33% control (D); (FIG. 6D) 100% control (D).

DETAILED DESCRIPTION

Figure 1:
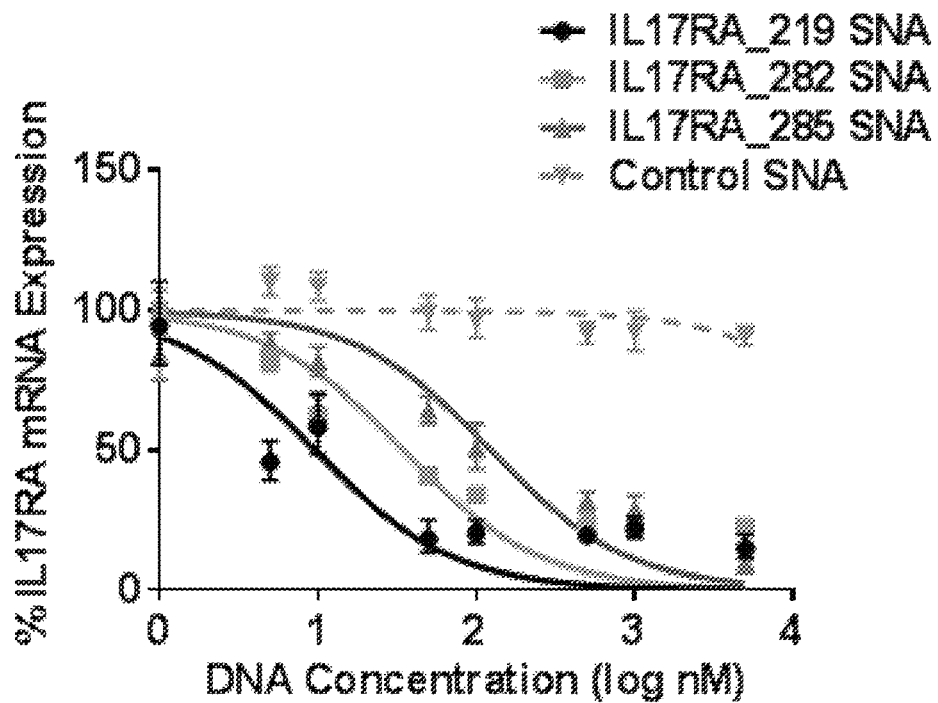
FIG. 1 depicts in vitro IL-17RA mRNA knockdown using targeted SNAs. IL-17RA mRNA expression is decreased in HFK cells treated with SNAs presenting an ASO sequence targeting IL-17RA. Cells treated with control SNAs do not demonstrate an appreciable decrease in IL-17RA mRNA expression.

The invention in some aspects relates to antisense inhibitors of a cell signaling protein receptor involved in systemic inflammation, Interleukin 17 receptor (IL-17RA). IL-17 and its target receptor IL-17RA play an important role in psoriasis. IL-17 elicits its effects by binding IL-17RA, the latter of which is expressed almost exclusively in keratinocytes within the epidermis. Antisense technology is a useful means for reducing the expression of specific gene products by targeting a messenger RNA (mRNA) and preventing translation of the mRNA. However, the selection of specific therapeutically functional antisense oligonucleotides (ASOs) can be challenging. Further, ASO that are therapeutically active in a linear form do not necessarily retain activity when formulated as a nanoparticle or other type of three dimensional presentation format.

It has been discovered in aspects of the invention that Spherical Nucleic Acids (SNAs) surface functionalized with antisense oligonucleotides (ASOs) having appropriate structural properties can mediate highly effective gene knockdown of the intended target mRNA. For example, it is demonstrated herein that IL-17RA expression can be inhibited through the use of SNAs targeting human IL-17RA (anti-IL17RA-SNAs) (see for instance GeneBank accession number NM_014339.6) mRNA in primary human foreskin keratinocytes (HFK) with no associated toxicity or immune-stimulatory effects. Further, it is shown that anti-IL-17RA SNAs inhibit mRNA expression in a human skin equivalent model and human skin explants. In some embodiments, the response the anti-IL-17RA SNAs inhibit IL-17RA mRNA expression in a dose-dependent manner. As described herein, the oligonucleotides arranged in an SNA geometry exhibit enhanced penetration and increased cellular uptake.

It has also been discovered that multiplex SNAs having different ASOs directed at different therapeutic targets can produce significant target knockdown and therapeutic effects. The ability to load specific amounts of different ASOs on the surface of an SNA in a way such that they do not interfere with the activity of the other ASOs was unexpected. As shown in the Examples, when anti-IL-17RA-SNAs were mixed with anti-TNF-SNAs and co-administered to cells, simultaneous mRNA knockdown of each targeted gene was achieved. Additionally when SNAs presenting two or more ASO sequences each targeting different mRNAs on the same particle were administered to cells the simultaneous mRNA knockdown of each gene targeted using a single particle in the same cell was achieved. These SNAs are referred to as multiplexed ASO-SNAs (mASO-SNA). Furthermore, when mASO-SNAs were multiplexed with ASOs targeting two mRNAs of genes involved in a related biological pathway, additive knockdown effects were observed. Not only did the co-presentation of the two ASOs not interfere with the activity of the other co-presented ASO but when targeting a common pathway the therapeutic effect observed with the mASO-SNAs was greater than that observed with either ASO-SNA alone.

The invention in some aspects relates to compositions for reducing IL-17RA and methods for treating an inflammatory disorder using those compositions. Highly effective IL-17RA inhibitors have been identified according to aspects of the invention. The IL-17RA inhibitors are nucleic acid based antisense compositions. The term "IL-17RA" refers to a receptor for the cytokine IL-17.

An "IL-17RA inhibitor" as used herein refers to a nucleic acid based agent which interferes with IL-17RA activity. In particular, the IL-17RA antisense inhibitors or IL-17RA antisense oligonucleotides of the invention reduce the expression of the IL-17RA gene. By reducing expression of the IL-17RA gene the endogenous IL-17 is not able to promote cell signaling through its interaction with the receptor. When IL-17RA is available for binding to IL-17, IL17RA is activated leading to induction of expression of inflammatory chemokines and cytokines such as CXCL1, CXCL8/IL8 and IL6. These signaling cascades can be blocked using the ASO-SNA of the invention.

The IL17RA inhibitors of the invention are antisense nucleic acids. Antisense nucleic acids typically include modified or unmodified RNA, DNA, or mixed polymer nucleic acids, and primarily function by specifically binding to matching sequences resulting in modulation of peptide synthesis. Antisense nucleic acids bind to target RNA by Watson Crick base-pairing and block gene expression by preventing ribosomal translation of the bound sequences either by steric blocking or by activating RNase H enzyme. Antisense molecules may also alter protein synthesis by interfering with RNA processing or transport from the nucleus into the cytoplasm.

In some embodiments, the invention relates to compositions for reducing interleukin-4 receptor (IL-4R) (see e.g., GenBank: NM_000418 (SEQ ID NO: 306)) and methods for treating an inflammatory disorder using those compositions. Highly effective IL-4R inhibitors have been identified according to aspects of the invention. The IL-4R inhibitors are nucleic acid based antisense compositions. The term "IL-4R" refers to a receptor for the cytokine IL-4 or IL-13.

An "IL-4R inhibitor" as used herein refers to a nucleic acid based agent which interferes with IL-4R activity. In particular, the IL-4R antisense inhibitors or IL-4R antisense oligonucleotides of the invention reduce the expression of the IL-4R gene. In some embodiments, the antisense oligonucleotide is 18 nucleotides in length. In other embodiments, IL-17RA has a sequence of SEQ ID NO: 302. By reducing expression of the IL-4R gene the endogenous IL-4 or IL-13 is not able to promote cell signaling through its interaction with the receptor. When IL-4R is available for binding to IL-4 or IL-13, IL-4R is activated leading to coupling to the JAK1/2/3-STAT6 pathway. The IL4 response is involved in promoting Th2 differentiation. The IL-4/IL-13 responses are involved in regulating IgE production and, chemokine and mucus production at sites of allergic inflammation. In certain cell types, can signal through activation of insulin receptor substrates, IRS1/IRS2. Soluble IL4R (sIL4R) inhibits IL4-mediated cell proliferation and IL5 up-regulation by T-cells (Keegan et al., *Cell* (1994) 76:811-820). These signaling cascades can be blocked using the ASO-SNA of the invention.

The IL-4R inhibitors of the invention are antisense nucleic acids. Antisense nucleic acids typically include modified or unmodified RNA, DNA, or mixed polymer nucleic acids, and primarily function by specifically binding to matching sequences resulting in modulation of peptide synthesis. Antisense nucleic acids bind to target RNA by Watson Crick base-pairing and block gene expression by preventing ribosomal translation of the bound sequences either by steric blocking or by activating RNase H enzyme. Antisense molecules may also alter protein synthesis by interfering with RNA processing or transport from the nucleus into the cytoplasm.

In some embodiments, the invention relates to compositions for reducing interleukin-1 beta (IL-1β) (see e.g., GenBank: NM_000576 (SEQ ID NO: 307)) and methods for treating an inflammatory disorder using those compositions. Highly effective IL-1β inhibitors have been identified according to aspects of the invention. The IL-1β inhibitors are nucleic acid based antisense compositions. The term "IL-1β" refers to a proinflammatory cytokine that was initially discovered as the major endogenous pyrogen, induces prostaglandin synthesis, neutrophil influx and activation, T-cell activation and cytokine production, B-cell activation and antibody production, and fibroblast proliferation and collagen production. Promotes Th17 differentiation of T-cells.

An "IL-1β inhibitor" as used herein refers to a nucleic acid based agent which interferes with IL-1β activity. In particular, the IL-1β antisense inhibitors or IL-1β antisense oligonucleotides of the invention reduce the expression of the IL-1β gene. By reducing expression of the IL-1β gene, signaling is reduced or not carried out (Van Damme et al., *Nature* (1985) 314:266-268; Piccioli et al., *Semin Immunol* (2013) 25(6):425-9). The signaling cascades that involve IL-1 β can be blocked using the ASO-SNA of the invention.

The IL-1β inhibitors of the invention are antisense nucleic acids. Antisense nucleic acids typically include modified or unmodified RNA, DNA, or mixed polymer nucleic acids, and primarily function by specifically binding to matching sequences resulting in modulation of peptide synthesis. Antisense nucleic acids bind to target RNA by Watson Crick base-pairing and block gene expression by preventing ribosomal translation of the bound sequences either by steric blocking or by activating RNase H enzyme. Antisense molecules may also alter protein synthesis by interfering with RNA processing or transport from the nucleus into the cytoplasm.

In some embodiments, the invention relates to compositions for reducing connective tissue growth factor (CTGF) (see e.g., GenBank: NM_001901 (SEQ ID NO: 308)) and methods for treating a disorder (e.g., atherosclerosis, pulmonary and renal fibrotic disorders and cancer) using those compositions. Highly effective CTGF inhibitors have been identified according to aspects of the invention. The CTGF inhibitors are nucleic acid based antisense compositions.

The term "CTGF" refers to a connective tissue mitoattractant secreted by cells (e.g., vascular endothelial cells) that, among other things, promotes proliferation and differentiation of chondrocytes; mediates heparin- and divalent cation-dependent cell adhesion in many cell types including fibroblasts, myofibroblasts, endothelial and epithelial cells; and enhances fibroblast growth factor-induced DNA synthesis.

An "CTGF inhibitor" as used herein refers to a nucleic acid based agent which interferes with CTGF activity. In particular, the CTGF antisense inhibitors or CTGF antisense oligonucleotides of the invention reduce the expression of the CTGF gene. By reducing expression of the CTGF gene, cell signaling is not promoted. For instance, CTGF interacts with growth factors, surface receptors and matrix components, with important roles in embryonic development and the maintenance of normal cell and connective tissue function, due to its widespread expression. CTGF is also important for tissue repair following injury, and has been implicated in common diseases including atherosclerosis, pulmonary and renal fibrotic disorders and cancer (de Winter et al., *Growth Factors* (2008) 26(2):80-91). The signaling cascades that CTGF is involved in can be blocked using the ASO-SNA of the invention.

The CTGF inhibitors of the invention are antisense nucleic acids. Antisense nucleic acids typically include modified or unmodified RNA, DNA, or mixed polymer nucleic acids, and primarily function by specifically binding to matching sequences resulting in modulation of peptide synthesis. Antisense nucleic acids bind to target RNA by Watson Crick base-pairing and block gene expression by preventing ribosomal translation of the bound sequences either by steric blocking or by activating RNase H enzyme. Antisense molecules may also alter protein synthesis by interfering with RNA processing or transport from the nucleus into the cytoplasm.

As used herein, the term "antisense nucleic acid" or "antisense oligonucleotide" describes a nucleic acid that hybridizes under physiological conditions to DNA comprising a particular gene or to an mRNA transcript of that gene in this case IL17RA and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

"Inhibition of gene expression" refers to the absence or observable decrease in the level of protein and/or mRNA product from a target gene, such as the IL17RA gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

The antisense oligonucleotides of the invention inhibit IL17RA expression. Depending on the assay, quantitation of the amount of gene expression allows one to determine a degree of inhibition which is greater than 5%, 10%, 20%, 30%, 40%, 50%, 60%, 70%, 80%, 90%, 95% or 99% as compared to a cell not treated according to the present invention. As an example, the efficiency of inhibition may be determined by assessing the amount of gene product in the cell.

The ASOs described herein include bioequivalent compounds, salts and prodrugs thereof. The term bioequivalent compounds, including pharmaceutically acceptable salts and prodrugs as used herein refers to antisense oligonucleotides having the same primary structure as the antisense oligonucleotide of interest, but including salt forms or structures which can be cleaved or modified to have the same type of biological effect as the antisense oligonucleotide of interest. This is intended to encompass any pharmaceutically acceptable salts, esters, or salts of such esters, or any other compound which, upon administration to an animal including a human, is capable of providing (directly or indirectly) the biologically active metabolite or residue thereof.

"Pharmaceutically acceptable salts" are physiologically and pharmaceutically acceptable salts of the nucleic acids of the invention: i.e., salts that retain the desired biological activity of the compound of interest and do not impart undesired toxicological effects thereto. Pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The compounds of the invention may also be prepared to be delivered in a "prodrug" form. A "prodrug" is a therapeutic agent that is prepared in an inactive form that is converted to an active form (i.e., drug) within the body or cells thereof by the action of endogenous enzymes or other chemicals and/or conditions.

The antisense oligonucleotides of the invention are IL17RA antisense oligonucleotides. An antisense IL17RA oligonucleotide refers to a compound having a sequence of nucleotide bases and a subunit-to-subunit backbone that allows the antisense oligonucleotide to hybridize to a IL17RA target mRNA sequence typically by Watson-Crick base pairing, to form an RNA:oligomer heteroduplex within the target sequence.

The specific hybridization of an antisense oligonucleotide with its target nucleic acid, IL17RA mRNA, interferes with the normal function of the IL17RA mRNA. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of IL17RA protein. In the context of the present invention, "modulation" means a decrease or inhibition in the expression of a gene.

An antisense oligonucleotide "specifically hybridizes" to a target polynucleotide if the oligonucleotide hybridizes to the IL17RA target under physiological conditions, with a thermal melting temperature (Tm) substantially greater than 37° C., preferably at least 45° C., and typically 50° C.-80° C. or higher. Such hybridization preferably corresponds to stringent hybridization conditions, selected to be about 10° C., and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules. An antisense compound may be complementary to a target region of a target transcript even if the two bases sequences are not 100% complementary, as long as the heteroduplex structure formed between the compound and transcript has the desired Tm stability.

Identifying an antisense oligonucleotide that targets a particular nucleic acid may be a multistep process. The process usually begins with the identification of a nucleic acid sequence whose function is to be modulated. This may be, for example, a cellular gene (or mRNA transcribed from the gene) whose expression is associated with a particular inflammatory disorder or disease state. The targeting process also includes determination of a site or sites within this IL17RA gene for the antisense interaction to occur such that the desired effect, e.g., detection or modulation of expression of the protein, will result.

In some embodiments, antisense oligonucleotides are designed to target human Interleukin 17 receptor (IL-17RA), for instance, the nucleotide sequence of SEQ ID NO: 302, corresponding to interleukin 17 receptor A (IL-17RA), set forth below. Human IL-17RA cDNA sequence has been disclosed in Genbank accession number NM_014339.

(SEQ ID NO: 302)

```
  1 ctgggcccgg gctggaagcc ggaagcgagc aaagtggagc cgactcgaac tccaccgcgg
 61 aaaagaaagc ctcagaacgt tcgttcgctg cgtccccagc cggggccgag ccctccgcga
121 cgccagccgg gccatggggg ccgcacgcag cccgccgtcc gctgtcccgg ggccctgct
181 ggggctgctc ctgctgctcc tgggcgtgct ggccccgggt ggcgcctcc tgcgactcct
```

-continued

```
 241 ggaccaccgg gcgctggtct gctcccagcc ggggctaaac tgcacggtca agaatagtac 301 ctgcctggat gacagctgga ttcaccctcg aaacctgacc ccctcctccc caaaggacct 361 gcagatccag ctgcactttg cccacaccca acaaggagac ctgttccccg tggctcacat 421 cgaatggaca ctgcagacag acgccagcat cctgtacctc gagggtgcag agttatctgt 481 cctgcagctg aacaccaatg aacgtttgtg cgtcaggttt gagtttctgt ccaaactgag 541 gcatcaccac aggcggtggc gttttacctt cagccacttt gtggttgacc ctgaccagga 601 atatgaggtg accgttcacc acctgcccaa gcccatccct gatgggggacc caaaccacca 661 gtccaagaat tccttgtgc ctgactgtga gcacgccagg atgaaggtaa ccacgccatg 721 catgagctca ggcagcctgt gggaccccaa catcaccgtg gagaccctgg aggcccacca 781 gctgcgtgtg agcttcaccc tgtggaacga atctacccat taccagatcc tgctgaccag 841 ttttccgcac atggagaacc acagttgctt tgagcacatg caccacatac ctgcgcccag 901 accagaagag ttccaccagc gatccaacgt cacactcact ctacgcaacc ttaaagggtg 961 ctgtcgccac caagtgcaga tccagccctt cttcagcagc tgcctcaatg actgcctcag 1021 acactccgcg actgtttcct gcccagaaat gccagacact ccagaaccaa ttccggacta 1081 catgccccctg tgggtgtact ggttcatcac gggcatctcc atcctgctgg tgggctccgt 1141 catcctgctc atcgtctgca tgacctggag gctagctggg cctggaagtg aaaaatacag 1201 tgatgacacc aaatacaccg atggcctgcc tgcggctgac ctgatccccc caccgctgaa 1261 gcccaggaag gtctggatca tctactcagc cgaccacccc ctctacgtgg acgtggtcct 1321 gaaattcgcc cagttcctgc tcaccgcctg cggcacgaa gtggccctgg acctgctgga 1381 agagcaggcc atctcggagg caggagtcat gacctgggtg gccgtcaga agcaggagat 1441 ggtggagagc aactctaaga tcatcgtcct gtgctcccgc ggcacgcgcg ccaagtggca 1501 ggcgctcctg ggccgggggg cgcctgtgcg gctgcgctgc gaccacggaa agcccgtggg 1561 ggacctgttc actgcagcca tgaacatgat cctcccggac ttcaagaggc cagcctgctt 1621 cggcacctac gtagtctgct acttcagcga ggtcagctgt gacggcgacg tccccgacct 1681 gttcggcgcg cgccgcggt acccgctcat ggacaggttc gaggaggtgt acttccgcat 1741 ccaggacctg gagatgttcc agccgggccg catgcaccgc gtaggggagc tgtcggggga 1801 caactacctg cggagcccgg gcggcaggca gctccgcgcc gccctggaca ggttccggga 1861 ctggcaggtc cgctgtcccg actggttcga atgtgagaac ctctactcag cagatgacca 1921 ggatgccccg tccctggacg aagaggtgtt tgaggagcca ctgctgcctc cgggaaccgg 1981 catcgtgaag cgggcgcccc tggtgcgcga gcctggctcc caggcctgcc tggccataga 2041 cccgctggtc ggggaggaag gaggagcagc agtggcaaag ctggaacctc acctgcagcc 2101 ccggggtcag ccagcgccgc agcccctcca caccctggtg ctcgccgcag aggaggggc 2161 cctggtggcc gcggtggagc ctgggcccct ggctgacggt gccgcagtcc ggctggcact 2221 ggcggggggag ggcgaggcct gcccgctgct gggcagcccg ggcgctgggc gaaatagcgt 2281 cctcttcctc cccgtggacc ccgaggactc gccccttggc agcagcaccc ccatgcgtc 2341 tcctgacctc cttccagagg acgtgaggga gcacctcgaa ggcttgatgc tctcgctctt 2401 cgagcagagt ctgagctgcc aggcccaggg gggctgcagt agacccgcca tggtcctcac 2461 agacccacac acgccctacg aggaggagca gcggcagtca gtgcagtctg accagggcta 2521 catctccagg agctccccgc agccccccga gggactcacg gaaatggagg aagaggagga 2581 agaggagcag gacccaggga agccggccct gccactctct cccgaggacc tggagagcct 2641 gaggagcctc cagcggcagc tgcttttccg ccagctgcag aagaactcgg gctgggacac
```

```
2701  gatggggtca gagtcagagg ggcccagtgc atgagggcgg ctccccaggg accgcccaga 2761  tcccagcttt gagagaggag tgtgtgtgca cgtattcatc tgtgtgtaca tgtctgcatg 2821  tgtatatgtt cgtgtgtgaa atgtaggctt taaaatgtaa atgtctggat tttaatccca 2881  ggcatccctc ctaacttttc tttgtgcagc ggtctggtta tcgtctatcc ccaggggaat 2941  ccacacagcc cgctcccagg agctaatggt agagcgtcct tgaggctcca ttattcgttc 3001  attcagcatt tattgtgcac ctactatgtg gcgggcattt gggataccaa gataaattgc 3061  atgcggcatg gccccagcca tgaaggaact taaccgctag tgccgaggac acgttaaacg 3121  aacaggatgg gccgggcacg gtggctcacg cctgtaatcc cagcacactg ggaggccgag 3181  gcaggtggat cactctgagg tcaggagttt gagccagcct ggccaacatg gtgaaacccc 3241  atctccacta aaaatagaaa aattagccgg gcatggtgac acatgcctgt agtcctagct 3301  acttgggagg ctgaggcagg agaattgctt gaatctggga ggcagaggtt gcagtgagcc 3361  gagattgtgc cattgcactg cagcctggat gacagagcga gactctatct caaaaaaaaa 3421  aaaaaaaaaa gatggtcacg cgggatgtaa acgctgaatg ggccaggtgc agtggctcat 3481  gcttgtaatc ccagcacttt gggaaggcga ggcaggtgga ttgcttgagc tcaggagttc 3541  aagaccagcc tgggcgacat agtgagacct catctctacc taaattttt tttagtcagt 3601  catggtggca catgcctgta gtcccagcta ctcgggaggc tgatgccaga tgatcacttg 3661  agcccaggag gtagaggctg cagtgagcta taatggtacc attgcaatcc agcctgggca 3721  gcagagtgag accctgtctc aaaaaaaata aaaagtaga agatggagt ggaagcctgc 3781  ccagggttgt gagcatgcac gggaaaggca cccaggtcag gggggatccc cgaggagatg 3841  cctgagctga aggattgtgg ttggggaaag cgtagtccca gcaaggaagc agtttgtggg 3901  taagtgctgg gaggtgagtg gagtgagctt gtcagggagc tgctggtgga gcctggaggg 3961  gaaggaggga ggcagtgaga gagatcgggg tgggggtgg ggggatgtcg ccagagctca 4021  ggggtgggga cagccttgtg cgcatcagtc ctgaggcctg gggcaccttt cgtctgatga 4081  gcctctgcat ggagagaggc tgagggctaa acacagctgg atgtcacctg agttcattta 4141  taggaagaga gaaatgtcga ggtgaaacgt aaaagcatct ggcaggaagg tgagtctgaa 4201  gccctgcacc cgcgttccga ctatcagtgg ggagctgtta gcacgtagga ttcttcagag 4261  cagctgggct ggagctcccc tgagctcagg aagccccagg gtgcaagggc aaggaaatga 4321  ggggtggtgg gtcagtgaag atctgggcag accttgtgtg gggaaggggt gctgctgtga 4381  cttcagggtc tgaggtccaa agacagcatt tgaaaagagg ctctgaagcc agtgtttgaa 4441  gaatttgttc ctgaagtacc tcctgggggt aggctagagg cttctggctt cagggtcctg 4501  aagaacacat tgaggtgccg tctgacactg gaataggtgt cccttcattc ctatgcctga 4561  gtccttaact atatttccaa cctccagtga ggaggagaag attcggaaat gtgacaggag 4621  agcaaacagg acagtttgca tgtgtgtgtg cgcacacata catgtgcgtg aaagattatc 4681  aataaaagtg cataaatttg ttgatctggt aagagtttct agcaggaagg tcgagccact 4741  tactgtaggt caagaagttg ctagttgcgg agttttttct tgcagttaga ctttacctag 4801  tggtagcagg gccaccaaag ctctgtgtcc cagatggtgt atggcccata atccacccaa 4861  cagcagcaaa ggaccaggca aaggagaaca ggagcagaag cctcccagcc actagccttt 4921  tgggctcagt ctctccaata atcctggaga ggggcttcgt tgggtctgga cacctaccat 4981  gcattctgtg acctttccct agcttccaat aaataactgt ttgacgccca gagtacagga 5041  taccacaatg cactcttcct gcgtagagca catgttccca tctgctccca ttcctcagga
```

-continued

```
5101 accttgaatt ctagctctgc tggcctttga gcccatgcca gtaaatgtcc tgatgggcat
5161 tgcctactat ctccagggca gctgcctttg tcctcctaac agctttattg gagtacagtt
5221 cacttaccat acaatccaca attgaccctg cacaatttga tgccggttta gtatagtcac
5281 agttcagcag ccatcagcac agtcagtctt agagtttact accccaaaa gaaatccagc
5341 cccccttagt caccacccca acctccccat ccctaggcac ccctaggcta ctttgatctc
5401 tgtagacttg cctcttctgg acatgacata gagaaaggag tcataaattc tccaaggtgt
5461 ctgtttcttc tttaatgtca ttccctgttt ctcctcacat tccctcccca tttcctgggc
5521 ccagtctcac actggtcctt gcttaccta aatgctatta attccatcac tctgagtatg
5581 gtgtttgctg tccgctgaat gccaagagct tcaagagtgt gtgtaaataa agccacacct
5641 ttattttgt attattctga accatggcta ataaattgtt tcaccaagaa atgtctctct
5701 aagaacaggt gccctccacg ctgtgcccct cccacctctt cagctcgtct cctgagtgtg
5761 cagaggtggt tccggttggg aaagaagcag cggagcatct aaccatgcct gtgtccaggc
5821 cgattatgca cgcagccacc aacaagctcc caactcccgc gtagagtttc atgacttttt
5881 cctgcctact atcttgatcc tagtttttt tttgttttt tttttttaa ggaataatta
5941 ctttgattca aaaccagttt ctcttttctg cataggaagg tccttgaagg tgtttagggt
6001 ctaaaaaggg tggtgttcgg tctctgaaac atccattcag cagtttgagc tgggatctct
6061 gaatgcaagg gtatgatgga tatacttctt tcttgctttt gttgtgtttt ggttttttgt
6121 ttgttttaa gtcagggtct ctctgtcacc aggctgtatt acagtggtgc aatcatggct
6181 cactgcagcc tcgacctccc aggctcaagc catctttcca cctcagcctc ccagtggcta
6241 gaactacagg cgtgcaccac tgtgcccggc taatttgtgt gtatatattt tgtagaaatg
6301 gggtttcacc atgttgtcca ggctggtcac gaactcctgg gctcaagcca tctgcccgcc
6361 tcatcctccc aaagtgctgg gattataggc ctgagcccac cgtgcctggc cttctctgtt
6421 tatctttgaa aattaaatag ggcataagag agaagaagat gtacttacaa tgcagtgggt
6481 ggttttaact ctatagcctt tgggctctgt ggttggtgct ccccttccta aataaatgag
6541 gtgtatgcag ggccctcttc tgccttagcg ccctgccagc tgggactcca gcaaggcccg
6601 gggcacctga ggacagagtg agatggaggg ccgctgctcc agcagccggg cctgcatccc
6661 acaagtcaac tgtgtcggac agaggatcct tacaaagaag aggcagcagg gttgggggct
6721 ggccagctgc tcgtccgccc taggtagctt gctcatctgt aaagtgggtg gggcaggagt
6781 tcccacctca tggggtcctg gcaagcctgc agtatcccg agtggcacca gcctgcttct
6841 ggggcagagc agtttgtgcc ccctgaggta ccactgatcc tctttccctg ctattaggta
6901 ttgctctctt cctccggtgt ttgccttttc agattataga agtaatatgt gttcccatat
6961 ttggcgtctc tcaggagctc aggaagtact tggctgagtg aacatgtcca ttgtggaaaa
7021 atggcaacaa tatggattcc atgggtatat tttatagaag aatatgaaga aaagcagcta
7081 cccctaaacc cattgcacaa gctgttcatg ttaattctgt acccgacgct ttccccacgg
7141 ggcctcccct cactctgaaa tggcatccag gtccatcttg ccctccacct ctgcatggct
7201 ctccatgccc catcgcctct cccagatcct agcactgggt ccacactctc gccctgtcca
7261 tttaggttga tgaaagcagg cagtcacccg ggtgggccag tcttgcctgt gggaggaaca
7321 tgcagtctcc tgtctcatgg tttgaagtgt gccaggaagc ctggcccagc ccacctcccc
7381 ctggagtcct tcccaggagg aataacccct taggtcattg actataagat gagttcgctc
7441 actggatcct tcctctctga tgagacagga agaaggtaca cagtgaccag gtaggaggag
7501 gagagggagt agaaaggagg gatgcgggtg gctggtccct gcatttgcct gcttccctgc
```

```
7561 acgggtgtcc cactggccgc ctctgctcac cagtgtcatg ggattctctc agaagatgaa 7621 aacagcccct gcttttttgc tagaatggct gagctttcat ggaaaggaag ctggacccaa 7681 gcaacagccg actaccgaag gttgcctgga gcagtgcaga tgtgggagga agaagggcct 7741 tggtgcacac tggctttttct tcctgactgc aatgtggcat tgtgccagct acctcctctt 7801 tctcggcctc aggaaaatgg agagaaagca gccctgaagg tggctgtgac gagggaaggg 7861 gcagagggcc tgacagtcaa ccacgcgcta tattttcctg ttcttcctta gggcaagaac 7921 tgcatggcca gactcaggca aggcctaggt gtgggctggg cattgcctac acgtgaagag 7981 atcactccgc gtccctactg cacctgtcac aaagtgcctt ctgatatgcc tggcaaacca 8041 aaatcggtga gcgccagctt gcttccctag aagacatttc taaatattca taacatgctt 8101 gctcaaatca atcaccttat tttacatccg ctccagggag aaatgaagac atggtcctac 8161 gttgttctgt aattattttc tatgtaaatt ttgttccttg ttacaattat atatgtctta 8221 ggggaaagga ccatttcaca tgtgtcacct catgtgattc tcaccacagc cctgtgattg 8281 ctcctgtttt ataaataatg acatagttcc agttgatggc caaagccaca gctaacgaga 8341 ggcagagaga gctcaggctc ccaggagctt ccactctcag accttgcctc ccgggctgcc 8401 ctgagtgaaa cgcctgctta gcatttggca cagccagaag cagcaagcta gggtcacaac 8461 acagagaggg gctgtgtaat actggctgcc tctgtgctaa gaaaaaaaaa aaatcactgt 8521 gtgtttgttt attttggtgc aggcccagtg ttcttgctta gacttaatac taccottcat 8581 gttaaaataa aaccaaacaa aaacccat
```

In some embodiments the IL-17RA ASO is complementary to a nucleic acid encoding the following protein sequence:

(SEQ ID NO: 305)
MGAARSPPSAVPGPLLGLLLLLLGVLAPGGASLRLLDHRALVCSQPGLNC
TVKNSTCLDDSWIHPRNLTPSSPKDLQIQLHFAHTQQGDLFPVAHIEWTL
QTDASILYLEGAELSVLQLNTNERLCVRFEFLSKLRHHHRRWRFTFSHFV
VDPDQEYEVTVHHLPKPIPDGDPNHQSKNFLVPDCEHARMKVTTPCMSSG
SLWDPNITVETLEAHQLRVSFTLWNESTHYQILLTSFPHMENHSCFEHMH
HIPAPRPEEFHQRSNVTLTLRNLKGCCRHQVQIQPFFSSCLNDCLRHSAT
VSCPEMPDTPEPIPDYMPLWVYWFITGISILLVGSVILLIVCMTWRLAGP
GSEKYSDDTKYTDGLPAADLIPPPLKPRKVWIIYSADHPLYVDVVLKFAQ
FLLTACGTEVALDLLEEQAISEAGVMTWVGRQKQEMVESNSKIIVLCSRG
TRAKWQALLGRGAPVRLRCDHGKPVGDLFTAAMNMILPDFKRPACFGTYV
VCYFSEVSCDGDVPDLFGAAPRYPLMDRFEEVYFRIQDLEMFQPGRMHRV
GELSGDNYLRSPGGRQLRAALDRFRDWQVRCPDWFECENLYSADDQDAPS
LDEEVFEEPLLPPGTGIVKRAPLVREPGSQACLAIDPLVGEEGGAAVAKL
EPHLQPRGQPAPQPLHTLVLAAEEGALVAAVEPGPLADGAAVRLALAGEG
EACPLLGSPGAGRNSVLFLPVDPEDSPLGSSTPMASPDLLPEDVREHLEG
LMLSLFEQSLSCQAQGGCSRPAMVLTDPHTPYEEEQRQSVQSDQGYISRS
SPQPPEGLTEMEEEEEEQDPGKPALPLSPEDLESLRSLQRQLLFRQLQK
NSGWDTMGSESEGPSA.

In some embodiments the ASOs used herein include any one or more of the following IL-17RA ASOs:

mGmCmUmUmGmGG*C*A*G*G*T*mGmGmUmGm
AmA/isp18//isp18//3CholTEG/(SEQ ID NO: 225);

mCmCmCmAmCmAmGG*G*G*C*A*T*mGmUmAm
GmU/isp18//isp18//3CholTEG/(SEQ ID NO: 288);

mGmUmAmGmGmGmCmGmUG*T*G*T*G*G*mGm
UmC/isp18//isp18//3CholTEG/(SEQ ID NO: 291);
mGmCmUmUmGmGG*C*A*G*G*T*mGmGmUm
GmAmA (SEQ ID NO: 225);

mCmCmCmAmCmAmGG*G*G*C*A*T*mGmUmAm
GmU (SEQ ID NO: 288);

mGmUmAmGmGmGmCmGmUG*T*G*T*G*G*mGm
UmC (SEQ ID NO: 291); GCUUGGGCAGGTG-
GUGAA (SEQ ID NO: 225); CCCACAGGGGCAT-
GUAGU (SEQ ID NO: 288); or
GUAGGGCGUGTGTGGGUC (SEQ ID NO: 291) or
salts thereof.

In some embodiments antisense oligonucleotides are designed to target the nucleotide sequence corresponding to IL-4R, set forth below. Human IL-4R cDNA sequence has been disclosed in Genbank accession number NM_000418.

(SEQ ID NO: 306)

```
   1 gggtctccgc gcccaggaaa gccccgcgcg gcgcgggcca gggaagggcc acccaggggt
  61 cccccacttc ccgcttgggc gcccggacgg cgaatggagc aggggcgcgc agataattaa
 121 agatttacac acagctggaa gaaatcatag agaagccggg cgtggtggct catgcctata
 181 atcccagcac ttttggaggc tgaggcgggc agatcacttg agatcaggag ttcgagacca
 241 gcctggtgcc ttggcatctc ccaatggggt ggctttgctc tgggctcctg ttccctgtga
 301 gctgcctggt cctgctgcag gtggcaagct ctgggaacat gaaggtcttg caggagccca
 361 cctgcgtctc cgactacatg agcatctcta cttgcgagtg aagatgaat ggtcccacca
 421 attgcagcac cgagctccgc ctgttgtacc agctggtttt tctgctctcc gaagcccaca
 481 cgtgtatccc tgagaacaac ggaggcgcgg ggtgcgtgtg ccacctgctc atggatgacg
 541 tggtcagtgc ggataactat acactggacc tgtgggctgg gcagcagctg ctgtggaagg
 601 gctccttcaa gcccagcgag catgtgaaac ccagggcccc aggaaacctg acagttcaca
 661 ccaatgtctc cgacactctg ctgctgacct ggagcaaccc gtatcccct gacaattacc
 721 tgtataatca tctcacctat gcagtcaaca tttggagtga aaacgacccg gcagatttca
 781 gaatctataa cgtgacctac ctagaaccct ccctccgcat cgcagccagc accctgaagt
 841 ctgggatttc ctacagggca cgggtgaggg cctgggctca gtgctataac accacctgga
 901 gtgagtggag ccccagcacc aagtggcaca actcctacag ggagcccttc gagcagcacc
 961 tcctgctggg cgtcagcgtt tcctgcattg tcatcctggc cgtctgcctg ttgtgctatg
1021 tcagcatcac caagattaag aaagaatggt gggatcagat tcccaaccca gcccgcagcc
1081 gcctcgtggc tataataatc caggatgctc aggggtcaca gtgggagaag cggtcccgag
1141 gccaggaacc agccaagtgc ccacactgga gaattgtctc taccaagctc ttgccctgtt
1201 ttctggagca acatgaaa agggatgaag atcctcacaa ggctgccaaa gagatgcctt
1261 tccagggctc tggaaaatca gcatggtgcc cagtggagat cagcaagaca gtcctctggc
1321 cagagagcat cagcgtggtg cgatgtgtgg agttgtttga ggccccggtg gagtgtgagg
1381 aggaggagga ggtagaggaa gaaaaaggga gcttctgtgc atcgcctgag agcagcaggg
1441 atgacttcca ggagggaagg gagggcattg tggcccggct aacagagagc ctgttcctgg
1501 acctgctcgg agaggagaat gggggcttt gccagcagga catgggggag tcatgccttc
1561 ttccaccttc gggaagtacg agtgctcaca tgccctggga tgagttccca agtgcagggc
1621 ccaaggaggc acctccctgg ggcaaggagc agcctctcca cctggagcca gtcctcctg
1681 ccagcccgac ccagagtcca gacaacctga cttgcacaga gacgccctc gtcatcgcag
1741 gcaaccctgc ttaccgcagc ttcagcaact ccctgagcca gtcaccgtgt cccagagagc
1801 tgggtccaga cccactgctg ccagacacc tggaggaagt agaacccgag atgccctgtg
1861 tcccccagct ctctgagcca accactgtgc cccaacctga gccagaaacc tgggagcaga
1921 tcctccgccg aaatgtcctc cagcatgggg cagctgcagc cccgtctcg gccccccacca
1981 gtggctatca ggagtttgta catgcggtgg agcagggtgg cacccaggcc agtgcggtgg
2041 tgggcttggg tccccaggga gaggctggtt acaaggcctt ctcaagcctg cttgccagca
2101 gtgctgtgtc cccagagaaa tgtgggtttg gggctagcag tggggaagag gggtataagc
2161 ctttccaaga cctcattcct ggctgccctg ggaccctgc cccagtccct gtcccttgt
2221 tcacctttgg actggacagg gagccacctc gcagtccgca gagctcacat ctcccaagca
2281 gctccccaga gcacctgggt ctggagccgg gggaaaaggt agaggacatg ccaaagcccc
2341 cacttcccca ggagcaggcc acagaccccc ttgtgacag cctgggcagt ggcattgtct
```

```
-continued
2401 actcagccct tacctgccac ctgtgcggcc acctgaaaca gtgtcatggc caggaggatg 2461 gtggccagac ccctgtcatg gccagtcctt gctgtggctg ctgctgtgga gacaggtcct 2521 cgccccctac aaccccctg agggccccag acccctctcc aggtgggtt ccactggagg 2581 ccagtctgtg tccggcctcc ctggcaccct cgggcatctc agagaagagt aaatcctcat 2641 catccttcca tcctgcccct ggcaatgctc agagctcaag ccagacccc aaaatcgtga 2701 actttgtctc cgtgggaccc acatacatga gggtctctta ggtgcatgtc ctcttgttgc 2761 tgagtctgca gatgaggact agggcttatc catgcctggg aaatgccacc tcctggaagg 2821 cagccaggct ggcagatttc caaaagactt gaagaaccat ggtatgaagg tgattggccc 2881 cactgacgtt ggcctaacac tgggctgcag agactggacc ccgcccagca ttgggctggg 2941 ctcgccacat cccatgagag tagagggcac tgggtcgccg tgccccacgg caggccctg 3001 caggaaaact gaggcccttg gcacctcga cttgtgaacg agttgttggc tgctccctcc 3061 acagcttctg cagcagactg tccctgttgt aactgcccaa ggcatgtttt gcccaccaga 3121 tcatgcccca cgtggaggcc cacctgcctc tgtctcactg aactagaagc cgagcctaga 3181 aactaacaca gccatcaagg gaatgacttg gcggccttg ggaaatcgat gagaaattga 3241 acttcaggga gggtggtcat tgcctagagg tgctcattca tttaacagag cttccttagg 3301 ttgatgctgg aggcagaatc ccggctgtca aggggtgttc agttaagggg agcaacagag 3361 gacatgaaaa attgctatga ctaaagcagg gacaatttgc tgccaaacac ccatgcccag 3421 ctgtatggct gggggctcct cgtatgcatg gaaccccag aataaatatg ctcagccacc 3481 ctgtgggccg ggcaatccag acagcaggca taaggcacca gttaccctgc atgttggccc 3541 agacctcagg tgctagggaa ggcgggaacc ttgggttgag taatgctcgt ctgtgtgttt 3601 tagtttcatc acctgttatc tgtgtttgct gaggagagtg gaacagaagg ggtggagttt 3661 tgtataaata agtttctttt gtctctttaa aaaaaaaaaa aaaaaaaaa
```

In some embodiments the IL-4R ASO is complementary to a nucleic acid encoding the following protein sequence:

```
                                        (SEQ ID NO: 309)
MGWLCSGLLF PVSCLVLLQV ASSGNMKVLQ EPTCVSDYMS

ISTCEWKMNG PTNCSTELRL LYQLVFLLSE AHTCIPENNG

GAGCVCHLLM DDVVSADNYT LDLWAGQQLL WKGSFKPSEH

VKPRAPGNLT VHTNVSDTLL LTWSNPYPPD NYLYNHLTYA

VNIWSENDPA DFRIYNVTYL EPSLRIAAST LKSGISYRAR

VRAWAQCYNT TWSEWSPSTK WHNSYREPFE QHLLLGVSVS

CIVILAVCLL CYVSITKIKK EWWDQIPNPA RSRLVAIIIQ

DAQGSQWEKR SRGQEPAKCP HWKNCLTKLL PCFLEHNMKR

DEDPHKAAKE MPFQGSGKSA WCPVEISKTV LWPESISVVR

CVELFEAPVE CEEEEEVEEE KGSFCASPES SRDDFQEGRE

GIVARLTESL FLDLLGEENG GFCQQDMGES CLLPPSGSTS

AHMPWDEFPS AGPKEAPPWG KEQPLHLEPS PPASPTQSPD

NLTCTETPLV IAGNPAYRSF SNSLSQSPCP RELGPDPLLA

RHLEEVEPEM PCVPQLSEPT TVPQPEPETW EQILRRNVLQ

HGAAAAPVSA PTSGYQEFVH AVEQGGTQAS AVVGLGPPGE

AGYKAFSSLL ASSAVSPEKC GFGASSGEEG YKPFQDLIPG

CPGDPAPVPV PLFTFGLDRE PPRSPQSSHL PSSSPEHLGL

EPGEKVEDMP KPPLPQEQAT DPLVDSLGSG IVYSALTCHL

CGHLKQCHGQ EDGGQTPVMA SPCCGCCCGD RSSPPTTPLR

APDPSPGGVP LEASLCPASL APSGISEKSK SSSSFHPAPG

NAQSSSQTPK IVNEVSVGPT YMRVS
```

In some embodiments antisense oligonucleotides are designed to target the nucleotide sequence corresponding to IL-1β, set forth below. Human IL-1β cDNA sequence has been disclosed in Genbank accession number NM_000576.

```
                                        (SEQ ID NO: 307)
  1 accaaacctc ttcgaggcac aaggcacaac aggctgctct
    gggattctct tcagccaatc 61 ttcattgctc aagtgtctga agcagccatg gcagaagtac
    ctgagctcgc cagtgaaatg 121 atggcttatt acagtggcaa tgaggatgac ttgttctttg
    aagctgatgg ccctaaacag 181 atgaagtgct ccttccagga cctggacctc tgccctctgg
    atggcggcat ccagctacga 241 atctccgacc accactacag caagggcttc aggcaggccg
    cgtcagttgt tgtggccatg
```

-continued

```
 301 gacaagctga ggaagatgct ggttccctgc ccacagacct
     tccaggagaa tgacctgagc 361 accttctttc ccttcatctt tgaagaagaa cctatcttct
     tcgacacatg ggataacgag 421 gcttatgtgc acgatgcacc tgtacgatca ctgaactgca
     cgctccggga ctcacagcaa 481 aaaagcttgg tgatgtctgt tccatatgaa ctgaaagctc
     tccacctcca gggacaggat 541 atggagcaac aagtggtgtt ctccatgtcc tttgtacaag
     gagaagaaag taatgacaaa 601 atacctgtgg ccttgggcct caaggaaaag aatctgtacc
     tgtcctgcgt gttgaaagat 661 gataagccca ctctacagct ggagagtgta gatcccaaaa
     attacccaaa gaagaagatg 721 gaaaagcgat ttgtcttcaa caagatagaa atcaataaca
     agctggaatt tgagtctgcc 781 cagttcccca actggtacat cagcacctct caagcagaaa
     acatgcccgt cttcctggga 841 gggaccaaag gcggccagga tataactgac ttcaccatgc
     aatttgtgtc ttcctaaaga 901 gagctgtacc cagagagtcc tgtgctgaat gtggactcaa
     tccctagggc tggcagaaag 961 ggaacagaaa ggttttttgag tacggctata gcctggactt
     tcctgttgtc tacaccaatg 1021 cccaactgcc tgccttaggg tagtgctaag aggatctcct
     gtccatcagc caggacagtc 1081 agctctctcc tttcagggcc aatccccagc ccttttgttg
     agccaggcct ctctcacctc 1141 tcctactcac ttaaagcccg cctgacagaa accacggcca
     catttggttc taagaaaccc 1201 tctgtcattc gctcccacat tctgatgagc aaccgcttcc
     ctatttattt atttatttgt 1261 ttgtttgttt tattcattgg tctaatttat tcaaaggggg
     caagaagtag cagtgtctgt 1321 aaaagagcct agttttttaat agctatggaa tcaattcaat
     ttggactggt gtgctctctt 1381 taaatcaagt cctttaatta agactgaaaa tatataagct
     cagattattt aaatgggaat 1441 atttataaat gagcaaatat catactgttc aatggttctg
     aaataaactt cactgaag
```

In some embodiments the IL-1β ASO is complementary to a nucleic acid encoding the following protein sequence:

```
                                  (SEQ ID NO: 310)
MAEVPELASE MMAYYSGNED DLFFEADGPK QMKCSFQDLD

LCPLDGGIQL RISDHHYSKG FRQAASVVVA MDKLRKMLVP

CPQTFQENDL STFFPFIFEE EPIFFDTWDN EAYVHDAPVR

SLNCTLRDSQ QKSLVMSGPY ELKALHLQGQ DMEQQVVFSM

SFVQGEESND KIPVALGLKE KNLYLSCVLK DDKPTLQLES

VDPKNYPKKK MEKRFVFNKI EINNKLEFES AQFPNWYIST

SQAENMPVFL GGTKGGQDIT DFTMQFVSS
```

In some embodiments antisense oligonucleotides are designed to target the nucleotide sequence corresponding to CTGF, set forth below. Human CTGF cDNA sequence has been disclosed in Genbank accession number NM_001901.

```
                                 (SEQ ID NO: 308)
   1 aaactcacac aacaactctt ccccgctgag aggagacagc
     cagtgcgact ccaccctcca 61 gctcgacggc agccgccccg gccgacagcc ccgagacgac
     agcccggcgc gtcccggtcc 121 ccacctccga ccaccgccag cgctccaggc cccgccgctc
     cccgctcgcc gccaccgcgc 181 cctccgctcc gcccgcagtg ccaaccatga ccgccgccag
     tatgggcccc gtccgcgtcg 241 ccttcgtggt cctcctcgcc ctctgcagcc ggccggccgt
     cggccagaac tgcagcgggc 301 cgtgccggtg cccggacgag ccggcgccgc gctgcccggc
     gggcgtgagc ctcgtgctgg 361 acggctgcgg ctgctgccgc gtctgcgcca agcagctggg
     cgagctgtgc accgagcgcg 421 accccctgcg a cccgcacaag ggcctcttct gtgacttcgg
     ctccccgcc aaccgcaaga 481 tcggcgtgtg caccgccaaa gatggtgctc cctgcatctt
     cggtggtacg gtgtaccgca 541 gcggagagtc cttccagagc agctgcaagt accagtgcac
     gtgcctggac ggggcggtgg 601 gctgcatgcc cctgtgcagc atggacgttc gtctgccag
     ccctgactgc cccttcccga 661 ggagggtcaa gctgccgggg aaatgctgcg aggagtgggt
     gtgtgacgag cccaaggacc 721 aaaccgtggt tgggcctgcc ctcgcggctt accgactgga
     agacacgttt ggcccagacc 781 caactatgat tagagccaac tgcctggtcc agaccacaga
     gtggagcgcc tgttccaaga 841 cctgtgggat gggcatctcc acccgggtta ccaatgacaa
     cgcctcctgc aggctagaga 901 agcagagccg cctgtgcatg gtcaggcctt gcgaagctga
     cctggaagag aacattaaga 961 agggcaaaaa gtgcatccgt actcccaaaa tctccaagcc
     tatcaagttt gagctttctg 1021 gctgcaccag catgaagaca taccgagcta aattctgtgg
     agtatgtacc gacggccgat 1081 gctgcacccc ccacagaacc accaccctgc cggtggagtt
     caagtgccct gacggcgagg 1141 tcatgaagaa gaacatgatg ttcatcaaga cctgtgcctg
     ccattacaac tgtcccggag 1201 acaatgacat ctttgaatcg ctgtactaca ggaagatgta
     cggagacatg gcatgaagcc 1261 agagagtgag agacattaac tcattagact ggaacttgaa
     ctgattcaca tctcattttt 1321 ccgtaaaaat gatttcagta gcacaagtta tttaaatctg
     ttttttctaac tgggggaaaa 1381 gattcccacc caattcaaaa cattgtgcca tgtcaaacaa
     atagtctatc aacccagac 1441 actggtttga agaatgttaa gacttgacag tggaactaca
     ttagtacaca gcaccagaat
```

```
1501 gtatattaag gtgtggcttt aggagcagtg ggagggtacc
     agcagaaagg ttagtatcat 1561 cagatagcat cttatacgag taatatgcct gctatttgaa
     gtgtaattga gaaggaaaat 1621 tttagcgtgc tcactgacct gcctgtagcc ccagtgacag
     ctaggatgtg cattctccag 1681 ccatcaagag actgagtcaa gttgttcctt aagtcagaac
     agcagactca gctctgacat 1741 tctgattcga atgacactgt tcaggaatcg gaatcctgtc
     gattagactg gacagcttgt 1801 ggcaagtgaa tttgcctgta acaagccaga ttttttaaaa
     tttatattgt aaatattgtg 1861 tgtgtgtgtg tgtgtgtata tatatatata tgtacagtta
     tctaagttaa tttaaagttg 1921 tttgtgcctt tttatttttg tttttaatgc tttgatattt
     caatgttagc ctcaatttct 1981 gaacaccata ggtagaatgt aaagcttgtc tgatcgttca
     aagcatgaaa tggatactta 2041 tatggaaatt ctgctcagat agaatgacag tccgtcaaaa
     cagattgttt gcaaagggga

2101 ggcatcagtg tccttggcag gctgatttct aggtaggaaa
     tgtggtagcc tcacttttaa 2161 tgaacaaatg gcctttatta aaaactgagt gactctatat
     agctgatcag ttttttcacc 2221 tggaagcatt tgtttctact ttgatatgac tgttttcgg
     acagtttatt tgttgagagt 2281 gtgaccaaaa gttacatgtt tgcacctttc tagttgaaaa
     taaagtgtat atttttcta 2341 taaaaaaaaa aaaaaaa
```

In some embodiments the CTGF ASO is complementary to a nucleic acid encoding the following protein sequence:

(SEQ ID NO: 311)
MTAASMGPVR VAFVVLLALC SRPAVGQNCS GPCRCPDEPA

PRCPAGVSLV LDGCGCCRVC AKQLGELCTE RDPCDPHKGL

FCHFGSPANR KIGVCTAKDG APCIFGGTVY RSGESFQSSC

KYQCTCLDGA VGCMPLCSMD VRLPSPDCPF PRRVKLPGKC

CEEWVCDEPK DQTVVGPALA AYRLEDTFGP DPTMIRANCL

VQTTEWSACS KTCGMGISTR VTNDNASCRL EKQSRLCMVR

PCEADLEENI KKGKKCIRTP KISKPIKFEL SGCTSMKTYR

AKFCGVCTDG RCCTPHRTTT LPVEFKCPDG EVMKKNMMFI

KTCACHYNCP GDNDIFESLY YRKMYGDMA

The invention in some aspects relates to multiplex ASO-SNAs for reducing the expression of multiple gene targets. In some embodiments the mASO-SNAs include ASOs that target IL-17RA and TNFα. These particular mASOs-SNAs are particularly useful for treating inflammatory disorders. A "TNFα antisense oligonucleotide" or "TNF-α ASO" as used herein refers to a nucleic acid based agent which interferes with TNFα activity. In particular, the TNFα antisense inhibitors or TNFα antisense oligonucleotides of the invention reduce the expression of the TNFα gene.

TNF-α (tumor necrosis factor-alpha) is a pleiotropic cytokine produced by activated macrophages/monocytes and lymphocytes which often promotes inflammatory responses leading to a variety of diseases. TNF-α is released from macrophages, monocytes and natural killer cells and play an important role in inflammatory and immune responses, including the recruitment of leukocytes to injured tissues during bacterial and other microbial infections, and following stimulation with inflammatory substances. When present in excessive quantities, TNF-α is known to cause tissue injury, and has been implicated in the pathology associated with inflammatory and autoimmune diseases.

TNF-α mediates biological effects through two distinct membrane-protein receptors, TNF-RI and TNF-RII, which differ in sequence and molecular mass. TNF-RI is reported to be present at low levels in most, if not all, human cell types, and expression of the TNF-RI gene in humans can be upregulated by infection, interferons, and modulators of second messengers, such as phorbol esters. The extracellular portions of both TNF receptors also exist in soluble forms, which are derived from membrane-bound forms of the receptors by proteolytic cleavage at the cell surface. The soluble TNF receptors retain the ability to bind TNF-α in solution. Soluble TNF receptors have been identified in urine and sera from healthy individuals, and have been shown to be elevated in some chronic diseases and following inoculation with agents that induce TNF-α.

In some embodiments, antisense oligonucleotides are designed to target human TNFα, for instance, the nucleotide sequence of SEQ ID NO: 304, set forth below. Human TNF-α cDNA sequence has been published by Nedwin, G. E. et al. (Nucleic Acids Res. 1985, 13, 6361-6373); and is disclosed in Genbank accession number X02910 and NM_000594.

```
                                                      (SEQ ID NO: 304)
  1 gaattccggg tgatttcact cccggctgtc caggcttgtc ctgctacccc acccagcctt 61 tcctgaggcc tcaagcctgc caccaagccc ccagctcctc ctccccgcag gacccaaaca 121 caggcctcag gactcaacac agcttttccc tccaacccgt tttctctccc tcaacggact 181 cagctttctg aagcccctcc cagttctagt tctatctttt tcctgcatcc tgtctggaag 241 ttagaaggaa acagaccaca gacctggtcc ccaaaagaaa tggaggcaat aggttttgag 301 gggcatgggg acggggttca gcctccaggg tcctacacac aaatcagtca gtggcccaga 361 agacccccct cggaatcgga gcagggagga tgggagtgt gagggtatc cttgatgctt 421 gtgtgtcccc aactttccaa atccccgccc ccgcgatgga gaagaaaccg agacagaagg 481 tgcagggccc actaccgctt cctccagatg agctcatggg tttctccacc aaggaagttt
```

-continued

```
 541 tccgctggtt gaatgattct ttccccgccc tcctctcgcc ccagggacat ataaaggcag
 601 ttgttggcac acccagccag cagacgctcc ctcagcaagg acagcagagg accagctaag
 661 agggagagaa gcaactacag acccccccctg aaaacaaccc tcagacgcca catcccctga
 721 caagctgcca ggcaggttct cttcctctca catactgacc cacggcttca ccctctctcc
 781 cctggaaagg acaccatgag cactgaaagc atgatccggg acgtggagct ggccgaggag
 841 gcgctcccca agaagacagg ggggccccag ggctccaggg ggtgcttgtt cctcagcctc
 901 ttctccttcc tgatcgtggc aggcgccacc acgctcttct gcctgctgca ctttggagtg
 961 atcggccccc agagggaaga ggtgagtgcc tggccagcct tcatccactc tcccacccaa
1021 ggggaaatga gagacgcaag agagggagag agatgggatg ggtgaaagat gtgcgctgat
1081 agggagggat gagagagaaa aaaacatgga gaaagacggg gatgcagaaa gagatgtggc
1141 aagagatggg gaagagagag agagaaagat ggagagacag gatgtctggc acatggaagg
1201 tgctcactaa gtgtgtatgg agtgaatgaa tgaatgaatg aatgaacaag cagatatata
1261 aataagatat ggagacagat gtggggtgtg agaagagaga tgggggaaga aacaagtgat
1321 atgaataaag atggtgagac agaaagagcg ggaaatatga cagctaagga gagagatggg
1381 ggagataagg agagaagaag atagggtgtc tggcacacag aagacactca gggaaagagc
1441 tgttgaatgc tggaaggtga atacacagat gaatggagag agaaaccag acacctcagg
1501 gctaagagcg caggccagac aggcagccag ctgttcctcc tttaagggtg actccctcga
1561 tgttaaccat tctccttctc cccaacagtt ccccagggac ctctctctaa tcagccctct
1621 ggcccaggca gtcagtaagt gtctccaaac ctctttccta attctgggtt tgggtttggg
1681 ggtagggtta gtaccggtat ggaagcagtg ggggaaattt aaagttttgg tcttggggga
1741 ggatggatgg aggtgaaagt aggggggtat tttctaggaa gtttaagggt ctcagctttt
1801 tcttttctct ctcctcttca ggatcatctt ctcgaacccc gagtgacaag cctgtagccc
1861 atgttgtagg taagagctct gaggatgtgt cttggaactt ggagggctag gatttgggga
1921 ttgaagcccg gctgatggta ggcagaactt ggagacaatg tgagaaggac tcgctgagct
1981 caagggaagg gtggaggaac agcacaggcc ttagtgggat actcagaacg tcatggccag
2041 gtgggatgtg ggatgacaga cagagaggac aggaaccgga tgtggggtgg gcagagctcg
2101 agggccagga tgtggagagt gaaccgacat ggccacactg actctcctct ccctctctcc
2161 ctccctccag caaaccctca agctgagggg cagctccagt ggctgaaccg ccgggccaat
2221 gccctcctgg ccaatggcgt ggagctgaga gataaccagc tggtggtgcc atcagagggc
2281 ctgtacctca tctactccca ggtcctcttc aagggccaag gctgcccctc cacccatgtg
2341 ctcctcaccc acaccatcag ccgcatcgcc gtctcctacc agaccaaggt caacctcctc
2401 tctgccatca agagcccctg ccagagggag accccagagg gggctgaggc caagccctgg
2461 tatgagccca tctatctggg aggggtcttc cagctggaga agggtgaccg actcagcgct
2521 gagatcaatc ggcccgacta tctcgacttt gccgagtctg ggcaggtcta ctttgggatc
2581 attgccctgt gaggaggacg aacatccaac cttcccaaac gcctcccctg ccccaatccc
2641 tttattaccc cctccttcag acaccctcaa cctcttctgg ctcaaaaaga gaattggggg
2701 cttagggtcg gaacccaagc ttagaacttt aagcaacaag accaccactt cgaaacctgg
2761 gattcaggaa tgtgtggcct gcacagtgaa gtgctggcaa ccactaagaa ttcaaactgg
2821 ggcctccaga actcactggg gcctacagct ttgatccctg acatctggaa tctggagacc
2881 agggagcctt tggttctggc cagaatgctg caggacttga gaagacctca cctagaaatt
```

```
-continued
2941 gacacaagtg gaccttaggc cttcctctct ccagatgttt ccagacttcc ttgagacacg 3001 gagcccagcc ctccccatgg agccagctcc ctctatttat gtttgcactt gtgattattt 3061 attatttatt tattatttat ttatttacag atgaatgtat ttatttggga gaccggggta 3121 tcctggggga cccaatgtag gagctgcctt ggctcagaca tgttttccgt gaaaacggag 3181 ctgaacaata ggctgttccc atgtagcccc ctggcctctg tgccttcttt tgattatgtt 3241 ttttaaaata tttatctgat taagttgtct aaacaatgct gatttggtga ccaactgtca 3301 ctcattgctg agcctctgct ccccagggga gttgtgtctg taatcgccct actattcagt 3361 ggcgagaaat aaagtttgct tagaaaagaa acatggtctc cttcttggaa ttaattctgc 3421 atctgcctct tcttgtgggt gggaagaagc tccctaagtc ctctctccac aggctttaag 3481 atccctcgga cccagtccca tccttagact cctagggccc tggagaccct acataaacaa 3541 agcccaacag aatattcccc atcccccagg aaacaagagc ctgaacctaa ttacctctcc 3601 ctcagggcat gggaatttcc aactctggga attc
```

The nanostructures descried herein may be stable self-assembling nanostructures. For instance the nanostructure may be an antisense oligonucleotide of 18-21 nucleotides in length having a sequence described herein, wherein a hydrophobic group at the 3' or 5' terminus self-associates to form the core of the nanostructure in water or other suitable solvents. A hydrophobic group as used herein may include cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen.

The antisense oligonucleotides typically have a length of 10-30 or 15-20 bases, which is generally long enough to have one complementary sequence in the mammalian genome. Additionally, antisense compounds having a length of at least 12, typically at least 15 nucleotides in length hybridize well with their target mRNA. Thus, the antisense oligonucleotides of the invention are typically in a size range of 8-100 nucleotides, more preferably 12-50 nucleotides in length. In some embodiments of the invention the antisense oligonucleotides are of 18-19 nucleotides in length. The antisense oligonucleotides may include further nucleotides on the 5' and/or 3' end of the oligonucleotide. However an antisense oligonucleotide that is limited to 18 nucleotides in length, for example, does not have any additional nucleotides on the 5' or 3' end of the molecule. Other non-nucleotide molecules may be linked covalently or non-covalently to the 5' and/or 3' end of those oligonucleotides.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules are preferably synthetic (e.g., produced by nucleic acid synthesis). The oligonucleotides may be any size useful for producing antisense effects. In some embodiments they are 18-23 nucleotides in length. In other embodiments the antisense oligonucleotide is 18 nucleotides in length.

The terms "nucleic acid" and "oligonucleotide" may also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as hexose, 2'-F hexose, 2'-amino ribose, CEt-LNA, arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases). Other examples are described in more detail below.

The oligonucleotides may be DNA, RNA, PNA, LNA, ENA or hybrids including any chemical or natural modification thereof. Chemical and natural modifications are well known in the art. Such modifications include, for example, modifications designed to increase binding to a target strand (i.e., increase their melting temperatures), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50%, 60%, 70%, 80%, or 90% or more in translation relative to the lack of the modification—e.g., in an in vitro translation assay), the modification may not be optimal for the methods and compositions described herein.

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In some embodiments, the modified oligonucleotide is a single-stranded modified oligonucleotide. In some embodiments, the single-stranded modified oligonucleotide consists of 10-30, 10-35, 10-40, 10-45, 10-50, 10-60, 10-70, 10-80, 10-90, 10-100 or more than 100 linked nucleosides and has a gap segment. In some embodiments, a gap segment refers to one or more linked nucleic acids consisting of deoxynucleosides located at the center or near the center of a modified oligonucleotide, such as a single-stranded modified oligonucleotide. In some embodiments, the gap segment consists of 2-3, 2-4, 2-5, 2-6, 2-7, 2-8, 2-9, 2-10, 2-20, 2-30, 2-40 2-50, 10-20, 10-30, 10-40 or 10-50 linked deoxynucleosides.

A 5' wing segment corresponds to the linked nucleic acids (e.g., nucleosides) from the 5'-end of a modified oligonucleotide to the nucleic acid before the first nucleic acid at the 5'-end of the gap segment. A 3' wing segment corresponds to the linked nucleic acids (e.g., nucleosides) after the last nucleic acid at the 3' end of the gap segment to the last nucleic acid at the 3' end of the modified oligonucleotide.

The gap segment is positioned between the 5' wing segment and the 3' wing segment. In some embodiments, at least one nucleoside of the 5' wing segment and/or at least one nucleoside of the 3' wing segment comprises a modified nucleoside. In some embodiments, the internucleoside linkages within the gap segment and the linkages connecting the gap segment to the 3' wing segment and/or the 5' wing segment are all phosphorothioate linkages (*). In some embodiments, the internucleoside linkages connecting the rest of the nucleosides of both the 5' and 3' wing segments are phosphodiester linkages. In some embodiments, the nucleosides in the modified oligonucleotide are modified with a 2' O-methyl group. The nucleosides in the modified oligonucleoside can also be modified with any other modification described herein.

In some embodiments, the nucleobase sequence of the modified oligonucleotide consists of 10-30, 10-35, 10-40, 10-45, 10-50, 10-60, 10-70, 10-80, 10-90, 10-100 or more than 100 linked nucleosides and has a gap segment complementary to an equal length portion of the coding sequence (e.g., cDNA) of the IL-17R, such as IL-17RA (e.g., cDNA sequence of IL-17RA is represented by SEQ ID NO: 302), IL-17RB, IL-17RC, IL-17RD, or IL-17RE) (see e.g., Johansen et al., Br J Dermatol (2009) 160(2):319-24, or a pharmaceutically acceptable salt thereof.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Substituted sugar moieties include, but are not limited to one of the following at the 2' position: H (deoxyribose); OH (ribose); F; 0-, S-, or N-alkyl; 0-, S-, or N-alkenyl; 0-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl.

A chemically or naturally modified oligonucleotide may include, for example, at least one nucleotide modified at the 2' position of the sugar, most preferably a 2'-O-alkyl, 2'-O-alkyl-O-alkyl or 2'-fluoro-modified nucleotide or an end cap. In other embodiments, RNA modifications include 2'-fluoro, 2'-amino and 2' O-methyl modifications on the ribose of pyrimidines, abasic residues or an inverted base at the 3' end of the RNA.

The oligonucleotides useful according to the invention may include a single modified nucleoside. In other embodiments the oligonucleotide may include at least two modified nucleosides, at least 3, at least 4, at least 5, at least 6, at least 7, at least 8, at least 9, at least 10, at least 15, at least 20 or more nucleosides, up to the entire length of the oligonucleotide.

Nucleosides or nucleobases include the natural purine bases adenine (A) and guanine (G), and the pyrimidine bases thymine (T), cytosine (C) and uracil (U). Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl) adenine, 2 (amino)adenine, 2-(aminoalkyll)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl) adenine, 8-(thiol)adenine, N6-(isopentyl)adenine, N6 (methyl)adenine, N6, N6 (dimethyl)adenine, 2-(alkyl)guanine, 2 (propyl)guanine, 6-(alkyl)guanine, 6 (methyl)guanine, 7 (alkyl)guanine, 7 (methyl)guanine, 7 (deaza)guanine, 8 (alkyl)guanine, 8-(alkenyl)guanine, 8 (alkynyl)guanine, 8-(amino)guanine, 8 (halo)guanine, 8-(hydroxyl)guanine, 8 (thioalkyl)guanine, 8-(thiol)guanine, N (methyl)guanine, 2-(thio)cytosine, 3 (deaza) 5 (aza) cytosine, 3-(alkyl)cytosine, 3 (methyl)cytosine, 5-(alkyl) cytosine, 5-(alkynyl)cytosine, 5 (halo)cytosine, 5 (methyl) cytosine, 5 (propynyl)cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)

uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl)uracil, 5-(cyanoalkyl) uracil, 5-(dialkylaminoalkyl)uracil, 5 (dimethylaminoalkyl) uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio) pseudouracil, 5-(alkyl)-2,4 (dithio)pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio)pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 aminocarbonylethylenyl)-2,4-(dithio)pseudouracil, 1 (arninoalkylarninocarbonylethylenyl)-pseudouracil, 1 (arninoalkylarnino-carbonylethylenyl)-2(thio)-pseudouracil, 1(arninoalkylarninocarbonylethylenyl)-4 (thio)pseudouracil, 1 (arninoalkylarninocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(arninoalkylhydroxy)-1,3-(diaza)-2-(oxo)-phenoxazin-1-yl, 7-(arninoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(arninoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkylhydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deazainosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, diiluorotolyl, 4-(iluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino) purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolopyrimidin-2-on-3-yl, ortho-substituted-6-phenyl-pyrrolopyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

The antisense oligonucleotides of the invention may be chimeric oligonucleotides. Chimeric antisense compounds of the invention may be formed as composite structures of two or more oligonucleotides, modified oligonucleotides, oligonucleotides and/or oligonucleotide mimetics as described above. Such compounds have also been referred to in the art as hybrids or mixed backbone or chimeric or gapmers. In particular a gapmer is an oligonucleotide that has at least three discrete portions, two of which are similar i.e. include one or more backbone modifications, and surround a region that is distinct, i.e., does not include backbone modifications.

The oligonucleotides may include a molecular species at one or both ends, i.e., at the 3' and/or 5' end. A molecular species as used herein refers to any compound that is not a naturally occurring or non-naturally occurring nucleotide. Molecular species include but are not limited to a spacer, a lipid, a sterol, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, an octadecylamine or hexylamino-carbonyl-oxycholesterol moiety, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy576), Hoechst 33258 dye, psoralen, or ibuprofen.

The molecular species may be attached at various positions of the oligonucleotide. As described above, the molecular species may be linked to the 2'-end, 3'-end or 5'-end of the oligonucleotide, where it also serves the purpose to enhance the stability of the oligomer against 3'- or 5'-exonucleases. Alternatively, it may be linked to an internal nucleotide or a nucleotide on a branch. The molecular species may be attached to a 2'-position of the nucleotide. The molecular species may also be linked to the heterocyclic base of the nucleotide.

The molecular species may be connected to the oligonucleotide by a linker moiety. Optionally the linker moiety is a non-nucleotidic linker moiety. Non-nucleotidic linkers are e.g. abasic residues (dSpacer), oligoethyleneglycol, such as triethyleneglycol or hexaethylenegylcol, or alkane-diol, such as butanediol. The spacer units are preferably linked by phosphodiester, phosphorodithioate or phosphorothioate bonds. The linker units may appear just once in the molecule or may be incorporated several times, e.g. via phosphodiester, phosphorothioate, methylphosphonate, or amide linkages.

The oligonucleotide of the invention (separate from the linkers connecting nucleotides to the molecular species) may also contain non-nucleotidic linkers, in particular abasic linkers (dSpacers), trietyhlene glycol units or hexaethylene glycol units. Further preferred linkers are alkylamino linkers, such as C3, C6, C12 aminolinkers, and also alkylthiol linkers, such as C3 or C6 thiol linkers.

IL-17RA and TNFα play a role in a wide variety of inflammatory disorders. An inflammatory disorder as used herein refers to a disorder in which IL-17 or TNFα activity is detrimental to a particular physiological function in a subject. As used herein, the term "a disorder in which IL-17 or TNFα activity is detrimental" is intended to include diseases and other disorders in which the levels of these cytokines expressed in a subject suffering from the disorder plays a role in the pathophysiology of the disorder or as a factor that contributes to a worsening of or maintenance of the disorder. Accordingly, a disorder in which IL-17 or TNFα activity is detrimental is a disorder in which inhibition of IL-17/IL-17RA or TNFα activity is expected to alleviate at least one symptom and/or progression or worsening of the disorder. Such disorders may be evidenced, for example, by an increase in the concentration of IL-17 or TNFα in a biological fluid of a subject suffering from the disorder (e.g., an increase in the concentration of IL-17 or TNFα in serum, plasma, synovial fluid, etc. of the subject), which can be detected, for example, using a probe or an antibody for detecting IL-17 or TNFα message or protein respectively.

Inflammatory disorders include but are not limited to sepsis, infections, autoimmune diseases, cancer, transplant rejection and graft-versus-host disease, transplant rejection, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

The biological role played by IL-17 or TNFα in these diseases is known. Inhibiting IL-17RA and/or TNFα expression in these diseases provides a therapeutic treatment for the disorder.

The ASO-SNAs and mASO-SNAs may be administered alone or in conjunction with another therapeutic agent for the treatment of an inflammatory disorder. Non-limiting examples of therapeutic agents with which the ASO-SNAs and mASO-SNAs of the invention can be combined include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; 55 kdTNF-IgG (55 kD TNF receptor-IgG fusion protein; Hoffmann-LaRoche); IDEC-CE9/SB 210396 (non-depleting primatized anti-CD4 antibody; IDEC/SmithKline; DAB 486-IL-2 and/or DAB 389-IL-2 (IL-2 fusion proteins; Seragen; Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1 RA (IL-1 receptor antagonist; Synergen/Amgen); anakinra (Kineret/Amgen); TNF-bp/s-TNF (soluble TNF binding protein); R973401 (phosphodiesterase Type IV inhibitor; MK-966 (COX-2 Inhibitor; Iloprost; methotrexate; thalidomide and thalidomide-related drugs (e.g., Celgen); leflunomide (anti-inflammatory and cytokine inhibitor; tranexamic acid (inhibitor of plasminogen activation; T-614 (cytokine inhibitor; prostaglandin E1; Tenidap (non-steroidal anti-inflammatory drug; Naproxen (non-steroidal anti-inflammatory drug; Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1-beta-converting enzyme); zap-70 and/or Ick inhibitor (inhibitor of the tyrosine kinase zap-70 or Ick); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11; interleukin-13; interleukin-17 inhibitors; gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. A number of studies have examined the optimal dosages for antisense oligonucleotides.

In certain embodiments, pharmaceutical compositions may comprise, for example, at least about 0.000001% (w/w) of an active compound. In other embodiments, the active compound may comprise between about 2% to about 75% of the weight of the unit (w/w), or between about 25% to about 60%, for example, and any range derivable therein. In some embodiments, the active compound (e.g., oligonucleotide or nanostructure) described herein comprises between 0.000001% and 0.00001%, between 0.00001% and 0.0001%, between 0.0001% and 0.001%, between 0.001% and 0.01%, between 0.01% and 0.1%, between 0.1% and 1%, between 1% and 5%, between 5% and 10%, between 10% and 15%, between 15% and 20%, between 20% and 25%, between 25% and 30%, between 30% and 40%, between 40% and 50% (w/w), and any range derivable in between. In some embodiments, the active compound (e.g., oligonucleotide or nanostructure) described herein comprises 0.00007%, 0.007%, 0.01%, 0.1%, 1% (w/w)

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, an anti-inflammatory agent, a sub-therapeutic dosage of either the molecules or the other agent, or a sub-therapeutic dosage of both, is used in the treatment of a subject having, or at risk of developing an inflammatory disorder. When the two classes of drugs are used together, the other agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a therapeutic agent is one which would not produce the desired therapeutic result in the subject in the absence of the administration of the molecules of the invention. Therapeutic doses of agents useful for treating inflammatory disorders are well known in the field of medicine. These dosages have been extensively described in references such as Remington's Pharmaceutical Sciences; as well as many other medical references relied upon by the medical profession as guidance for the treatment of infectious disease, cancer, and autoimmune disease. Therapeutic dosages of oligonucleotides have also been described in the art.

Dosing regimens may be several times a day, daily, every other day, weekly, biweekly any of the times there between or less frequently. The term "biweekly dosing" as used herein, refers to the time course of administering a substance (e.g., an anti-IL-17RA nucleic acid) to a subject once every two weeks. The oligonucleotides may be administered every 7-20 days, every 11-17 days, or every 13-15 days, for example.

In some embodiments, a compound (e.g., oligonucleotide, nanostructure, etc.) described herein is administered for 4, 8, 12, 16, 20, 24, 28, 32, 36, 40, 44, 48, 72, 96, 120, 240, 480 hours, or any ranges in between, per dose in a dosing schedule.

The oligonucleotides are administered in effective amounts. The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

In some embodiments, the cell is contacted with an oligonucleotide, a nanostructure, or a mASO-SNA described herein at a concentration of at least 0.001 nM, at least 0.01 nM, at least 0.1 nM, at least 1 nM, at least 10 nM, at least 100 nM, at least 1000 nM, at least 10 µM, at least 100 µM, at least 1000 µM, or above 1000 µM. In some embodiments, the cell is contacted with an oligonucleotide, a nanostructure, or a mASO-SNA described herein at a concentration range of 0.001 nM to 0.01 nM, 0.01 nM to 0.1 nM, 0.1 nM to 1 nM, 1 nM to 10 nM, 10 nM to 100 nM, 100 nM to 1000 nM, 1000 nM to 10 µM, 10 µM to 100 µM, or 100 µM to 1000 µM. In some embodiments, the cell is contacted with an oligonucleotide, a nanostructure, or a mASO-SNA described herein at a concentration of 0.001 nM, 0.01 nM, 0.1 nM, 1 nM, 10 nM, 100 nM, 1000 nM, 10 µM, 100 µM, 1000 µM or above 1000 µM.

The oligonucleotides described herein can be used alone or in conjugates with other molecules such as detection or cytotoxic agents in the detection and treatment methods of the invention, as described in more detail herein.

The oligonucleotide may be, for instance, coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to an oligonucleotide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the oligonucleotides described herein, or will be able to ascertain such, using routine experimentation. Furthermore, the coupling or conjugation of these labels to the oligonucleotides of the invention can be performed using standard techniques common to those of ordinary skill in the art.

Conjugation of the oligonucleotides to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In. In such instances, the use of the oligonucleotide could be observed as the oligonucleotide provides an antisense effect.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art. A variety of methods may be used to detect the label, depending on the nature of the label and other assay components.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

The agent may comprise different types of carriers depending on whether it is to be administered in solid, liquid, gel, cream, or aerosol form, and whether it need to be sterile for such routes of administration as injection. The present invention can be administered intravenously, intradermally, intraarterially, intralesionally, intratumorally, intracranially, intrathecally, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, via eyedrops, orally, topically, locally, inhalation (e.g., aerosol inhalation), injection, infusion, continuous infusion, localized perfusion bathing target cells directly, via a catheter, via a lavage, in creams, in gel, in lipid compositions (e.g., liposomes), or by other method or any combination of the forgoing as would be known to one of ordinary skill in the art.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection, topical application, or local application. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, thermoreversible hydrogels such as pluronic F-127, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The compositions of the invention may be formulated in a topical composition for administration to the skin or a body cavity. Suitable topical vehicles and vehicle components are well known in the cosmetic and pharmaceutical arts, and include such vehicles (or vehicle components) as water; thermoreversible hydrogels such as pluronic F-127, organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like.

The choice of a suitable vehicle will depend on the particular physical form and mode of delivery that the formulation is to achieve. Examples of suitable forms include liquids (e.g., gargles and mouthwashes, including dissolved forms of the strontium cation as well as suspensions, emulsions and the like); solids and semisolids such as gels, foams, pastes, creams, ointments, "sticks" (as in lipsticks or underarm deodorant sticks), powders and the like; formulations containing liposomes or other delivery vesicles; rectal or vaginal suppositories, creams, foams, gels or ointments; and other forms. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick—to the skin); spraying (including mist, aerosol or foam spraying); dropper application (as for example with ear drops); sprinkling (as with a suitable powder form of the formulation); and soaking.

Topical formulations also include formulations for rectal and vaginal administration. Formulations for rectal administration may be presented as a suppository with a suitable base comprising, for example, cocoa butter. Formulations suitable for vaginal administration may be presented as tablets, pessaries, tampons, creams, gels, pastes, foams or spray formulations containing in addition to the active ingredient such carriers as are known in the art to be appropriate.

In yet other embodiments, a delivery vehicle is a biocompatible microparticle or implant that is suitable for implantation into the mammalian recipient. Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides.

In some embodiments the antisense nucleic acids of the invention are formulated as a stable self-assembling nanostructure. The nanostructure includes a IL-17RA antisense oligonucleotide, wherein the antisense oligonucleotide is associated with a core. The core may be a solid or a hollow core, such as a liposomal core. A solid core is a spherical shaped material that does not have a hollow center. The term spherical as used herein refers to a general shape and does not imply or is not limited to a perfect sphere or round shape. It may include imperfections.

Solid cores can be constructed from a wide variety of materials known to those skilled in the art including but not limited to: noble metals (gold, silver), transition metals (iron, cobalt) and metal oxides (silica). In addition, these cores may be inert, paramagnetic, or superparamagnetic. These solid cores can be constructed from either pure compositions of described materials, or in combinations of mixtures of any number of materials, or in layered compositions of materials. In addition, solid cores can be composed of a polymeric core such as amphiphilic block copolymers, hydrophobic polymers such as polystyrene, poly(lactic acid), poly(lactic co-glycolic acid), poly(glycolic acid), poly (caprolactone) and other biocompatible polymers known to those skilled in the art.

The core may alternatively be a hollow core, which has at least some space in the center region of a shell material. Hollow cores include liposomal cores and niosomes. A liposomal core as used herein refers to a centrally located core compartment formed by a component of the lipids or phospholipids that form a lipid bilayer. "Liposomes" are artificial, self closed vesicular structure of various sizes and structures, where one or several membranes encapsulate an aqueous core. Most typically liposome membranes are formed from lipid bilayers membranes, where the hydrophilic head groups are oriented towards the aqueous environment and the lipid chains are embedded in the lipophilic core. Liposomes can be formed as well from other amphiphilic monomeric and polymeric molecules, such as polymers, like block copolymers, or polypeptides. Unilamellar vesicles are liposomes defined by a single membrane enclosing an aqueous space. In contrast, oligo- or multilamellar vesicles are built up of several membranes. Typically, the membranes are roughly 4 nm thick and are composed of amphiphilic lipids, such as phospholipids, of natural or synthetic origin. Optionally, the membrane properties can be modified by the incorporation of other lipids such as sterols or cholic acid derivatives.

The lipid bilayer is composed of two layers of lipid molecules. Each lipid molecule in a layer is oriented substantially parallel to adjacent lipid bilayers, and two layers that form a bilayer have the polar ends of their molecules exposed to the aqueous phase and the non-polar ends adjacent to each other. The central aqueous region of the liposomal core may be empty or filled fully or partially with water, an aqueous emulsion, oligonucleotides, or other therapeutic or diagnostic agents.

Niosomes are vesicles formed from non-ionic surfactant oriented in a bilayer. Niosomes commonly have cholesterol added as an excipient, but other lipid-based and non-lipid-based constituents can also be included. Methods for preparation of niosomes are known in the art. In some embodiments polyethylene glycol (PEG) is included during or following niosome preparation. Niosome vesicles are structurally and functionally analogous to liposomes, but are based on non-ionic surfactant rather than lipid as the primary constiuent. Common non-ionic surfactants used include sorbitans (spans) or polysorbates (tween); however, a wide variety of non-ionic surfactants can be used to prepare niosomes.

"Lipid" refers to its conventional sense as a generic term encompassing fats, lipids, alcohol-ether-soluble constituents of protoplasm, which are insoluble in water. Lipids usually consist of a hydrophilic and a hydrophobic moiety. In water lipids can self organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bola amphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

The liposomal core can be constructed from one or more lipids known to those in the art including but not limited to: 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE), sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

In certain embodiments, the diameter of the core is from 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, or about 1 nm to about 10 nm in mean diameter.

The oligonucleotides may be positioned on the exterior of the core, within the walls of the core and/or in the center of the core. An oligonucleotide that is positioned on the core is typically referred to as coupled to the core. Coupled may be direct or indirect. In some embodiments at least 5, 10, 15, 25, 50, 75, 100, 200, 300, 400, 500, 600, 700, 800, 900, 1000, 5000 or 10,000 oligonucleotides or any range combination thereof are on the exterior of the core. In some embodiments, 1-1000, 10-500, 50-250, or 50-300 oligonucleotides are present on the surface.

The oligonucleotides of the oligonucleotide shell may be oriented in a variety of directions. In some embodiments the oligonucleotides are oriented radially outwards. The orientation of these oligonucleotides can be either 5' distal/3' terminal in relation to the core, or 3' distal/5'terminal in relation to the core, or laterally oriented around the core. In one embodiment one or a multiplicity of different oligonucleotides are present on the same surface of a single SNA. In all cases, at least 1 oligonucleotide is present on the surface but up to 10,000 can be present.

The oligonucleotides may be linked to the core or to one another and/or to other molecules such an active agents either directly or indirectly through a linker. The oligonucleotides may be conjugated to a linker via the 5' end or the 3' end, e.g. [Sequence, 5'-3']-Linker or Linker-[Sequence, 5'-3']. Some or all of the oligonucleotides of the nanostructure may be linked to one another either directly or indirectly through a covalent or non-covalent linkage. The linkage of one oligonucleotide to another oligonucleotide may be in addition to or alternatively to the linkage of that oligonucleotide to liposomal core.

The oligonucleotide shell may be anchored to the surface of the core through one or multiple of linker molecules, including but not limited to: any chemical structure containing one or multiple thiols, such as the various chain length alkane thiols, cyclic dithiol, lipoic acid, or other thiol linkers known to those skilled in the art.

In an embodiment containing a liposomal core, the oligonucleotide shell may be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

The oligonucleotide may also be associated with the core by being embedded within the core (liposomal core) or it may be attached or linked, either indirectly (i.e. non-covalently or covalently through other molecules such a linkers) or directly (i.e. covalently).

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of inflammatory disorders.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation or pharmaceutical composition and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the inflammatory disease or disorder. In other words, the article of manufacture includes instruction means indicating or suggesting a dosing regimen including, but not limited to, actual doses, monitoring procedures and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

EXAMPLES

Example 1. Liposomal Spherical Nucleic Acid (SNA) Constructs Presenting Antisense Oligonucleotides (ASO) for Specific Knockdown of Interleukin 17 Receptor mRNA Results
Experiment 1. In Vitro IL-17RA mRNA Knockdown Using Targeted SNAs HFK cells were treated with 294 SNAs presenting one ASO sequence each of the sequences in Table 1 and human IL-17RA mRNA expression was measured by qRT-PCR. This was performed twice and the three SNAs showing the greatest inhibition of IL-17RA mRNA in multiple assays and having low off-target effects were chosen for further optimization by chemical modification. HFK cells were treated at larger dose ranges with SNAs presenting one ASO sequence of either IL17RA_219, IL17RA_282, IL17RA_285 or a non-complementary control. Targeted SNAs demonstrate target specific mRNA inhibition in a dose-dependent manner while the non-complementary control SNA has no considerable inhibition at all concentrations tested (FIG. 1). Targeted SNAs demonstrate similar IL-17RA mRNA inhibition in HEKa cells. Analyzing the dose-response data as a non-linear fit and calculating the half maximal inhibitory concentration ($IC_{50}$) results in $IC_{50}$ values of 124.2, 9.57 and 34.64 nM for IL17RA_285, IL17RA_219 and IL17RA_282, respectively. These results demonstrate that SNAs targeting IL-17RA mRNA can effectively inhibit gene expression in a specific manner in HFK cells.

Experiment 2. IL-17RA mRNA Knockdown Using Topically Applied Targeted SNAs in the Human Skin Equivalent, EpiDerm-FT™

Figure 2:
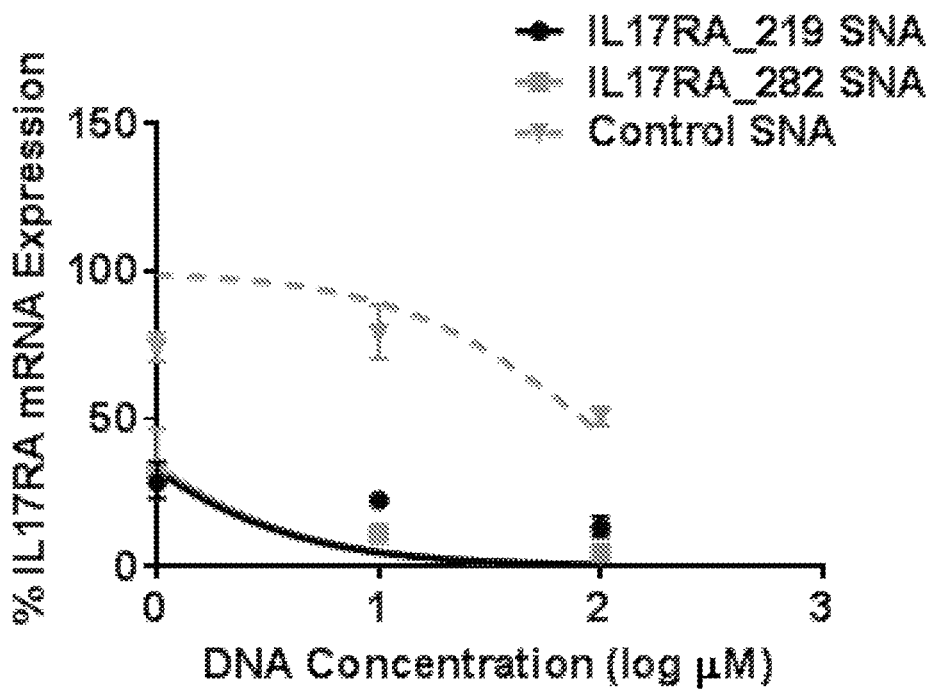
FIG. 2 shows IL-17RA mRNA knockdown using topically applied targeted SNAs in the human skin equivalent, EpiDerm-FT™. IL-17RA mRNA expression is decreased in human skin equivalent tissues treated topically with SNAs presenting either ASO IL17RA_219 or ASO IL17RA_282 for 48 hours. Tissues treated with SNAs presenting the control ASO do not demonstrate an appreciable decrease in IL-17RA mRNA expression as measured by qRT-PCR. Data shown are representative of two independent experiments performed.

A human skin equivalent model treated topically with SNAs presenting either ASO sequence IL17RA_219 or IL17RA_282 targeting human IL-17RA mRNA resulted in target mRNA specific inhibition. IL17RA_219 and IL17RA_282 were chosen as the lead candidate compounds for further testing after taking into consideration the efficacy data collected in experiment 1. ASOs IL17RA_219 and IL17RA_282 exhibited the best combination of $IC_{50}$ value, homology to other human mRNA sequences (as determined by BLAST) and cross-species conservation. IL-17RA mRNA expression is decreased in human skin equivalent tissues treated topically with SNAs presenting either ASO IL17RA_219 or ASO IL17RA_282 for 48 hours. Tissues treated with SNAs presenting the control ASO do not demonstrate an appreciable decrease in IL-17RA mRNA expression as measured by qRT-PCR (FIG. 2). Further, IL17RA_219 and IL17RA_282 exhibited no toxicity in HFKs and no cytokine induction in HFKs, HEKa cells and PBMCs from four different donors, up to 20 µM DNA concentration. For these reasons, IL17RA_219 and IL17RA_282 were chosen for further testing. SNAs targeting IL-17RA delivered topically were shown to specifically inhibit mRNA expression in a human skin equivalent model.

Figure 3:
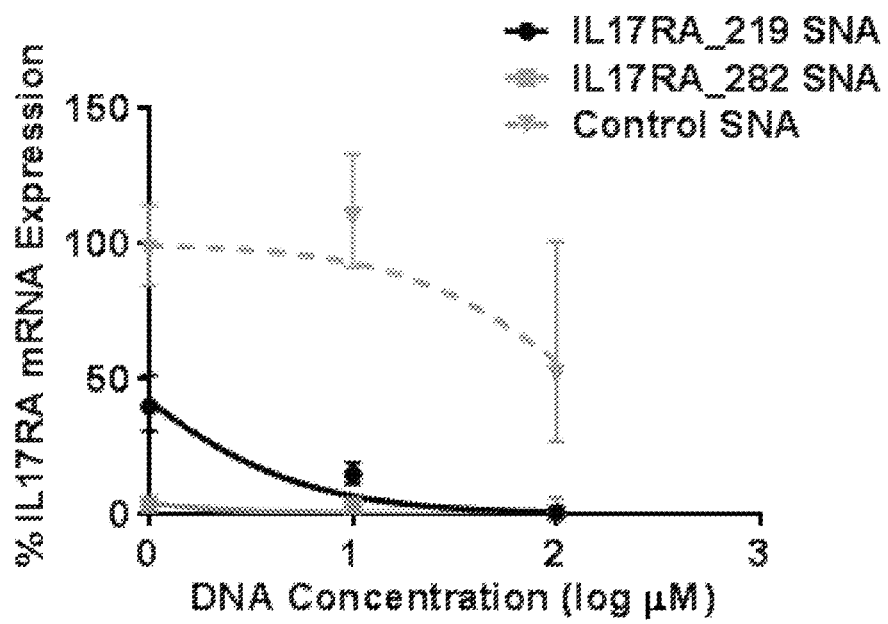
FIG. 3 shows ex vivo IL-17RA mRNA knockdown using topically applied targeted SNAs in human skin explants. IL-17RA mRNA expression is decreased in human skin explant biopsies treated topically with SNAs presenting either ASO IL17RA_219 or ASO IL17RA_282 for 96 hours. Biopsies treated with SNAs presenting the control ASO do not demonstrate an appreciable decrease in IL-17RA mRNA expression as measured by qRT-PCR.

Experiment 3. Ex Vivo IL-17RA mRNA Knockdown Using Topically Applied Targeted SNAs in Human Skin Explants Human skin explants treated topically with SNAs presenting either ASO sequence IL17RA_219 or ASO sequence IL17RA_282 targeting human IL-17RA mRNA resulted in target mRNA specific inhibition. IL-17RA mRNA expression is decreased in human skin explant biopsies treated topically with SNAs presenting either ASO IL17RA_219 or ASO IL17RA_282 for 96 hours. Biopsies treated with SNAs presenting the control ASO do not demonstrate an appreciable decrease in IL-17RA mRNA expression as measured by qRT-PCR (FIG. 3). SNAs targeting IL-17RA delivered topically can specifically inhibit mRNA expression in human skin explants.

Experiment 4. TNF mRNA Knockdown Using a Mixture of SNAs

SNAs presenting either an anti-TNF or an anti-IL17RA ASO sequence were mixed together and co-administered to HFK cells. Mixed SNAs demonstrated target mRNA specific knockdown corresponding to the ASO sequence identity (FIG. 4, FIG. 5).

Figure 4:
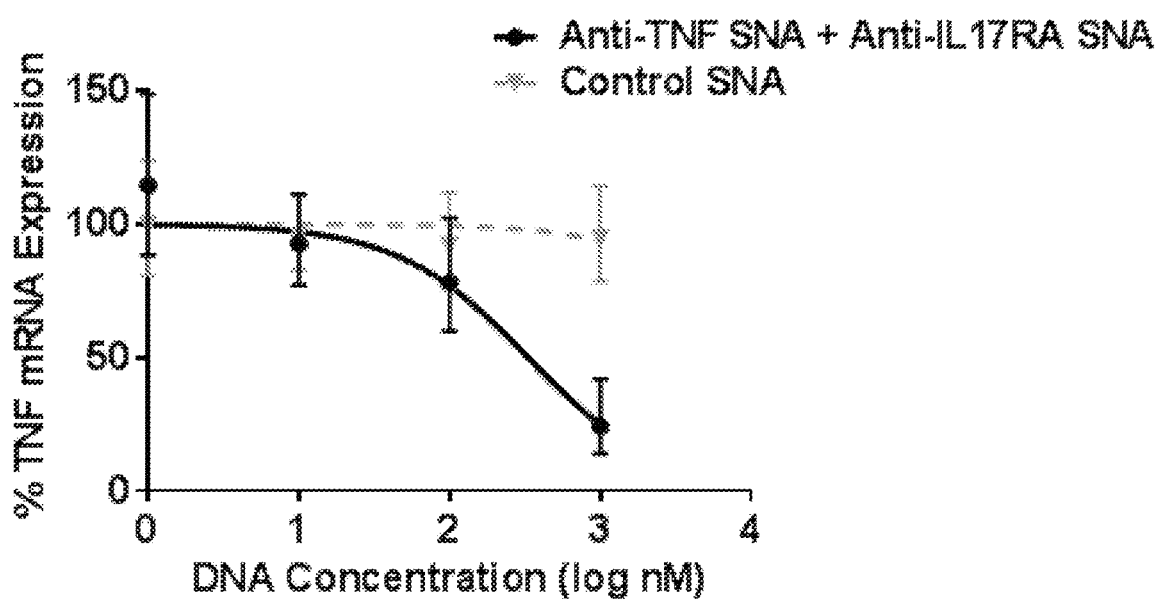
FIG. 4 shows TNF mRNA knockdown using a mixture of SNAs. TNF mRNA expression is decreased in HFK cells treated with a mixture of anti-TNF-SNAs and anti-IL17RA-SNAs. Cells treated with Control-SNAs do not demonstrate an appreciable decrease in TNF mRNA levels. Data shown are representative of two independent experiments performed.

FIG. 4 shows TNF mRNA expression decreased in HFK cells treated with a mixture of anti-TNF-SNAs and anti-IL17RA-SNAs. FIG. 5 shows IL17RA mRNA expression is decreased in HFK cells treated with a mixture of anti-TNF-SNAs and anti-IL17RA-SNAs. Cells treated with control-SNAs do not demonstrate an appreciable decrease in TNF mRNA levels.

These results demonstrate that mixtures of SNAs targeting more than one mRNA can be co-administered and perform gene knockdown with respect to each target.

Figure 7:
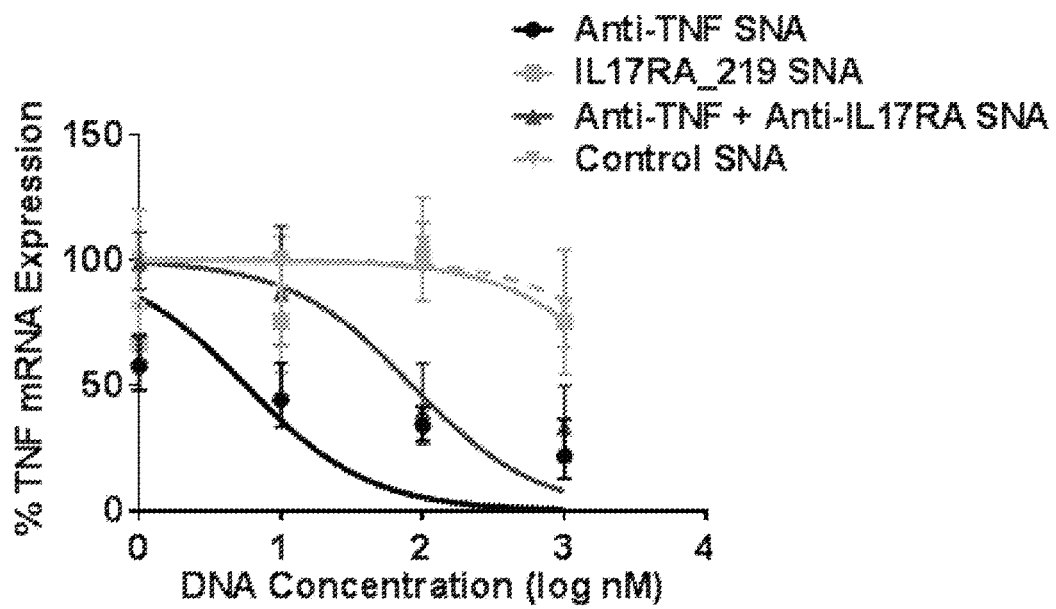
FIG. 7 shows a comparison of TNF mRNA knockdown using multiplexed SNAs. TNF mRNA expression is decreased in HFK cells treated with anti-TNF-SNAs and multiplexed SNAs containing anti-TNF and anti-IL17RA ASOs. Cells treated with anti-IL17RA-SNAs do not demonstrate an appreciable decrease in TNF mRNA levels. Data shown are representative of two independent experiments performed.

Experiment 5. Comparison of TNF mRNA Knockdown and IL17RA Knockdown Using Multiplexed SNAs SNAs presenting one, two, or three ASO sequences demonstrated target mRNA specific knockdown in HFK cells corresponding to the ASO sequence identity. Only data obtained using SNAs multiplexed with two ASO sequences. SNAs were shown to serve as a platform capable of presenting multiple therapeutic modalities. These results demonstrate that ASO sequences targeting more than one mRNA can be co-delivered on the same SNA particle and perform gene knockdown with respect to each target (FIG. 7, FIG. 8).

Figure 8:
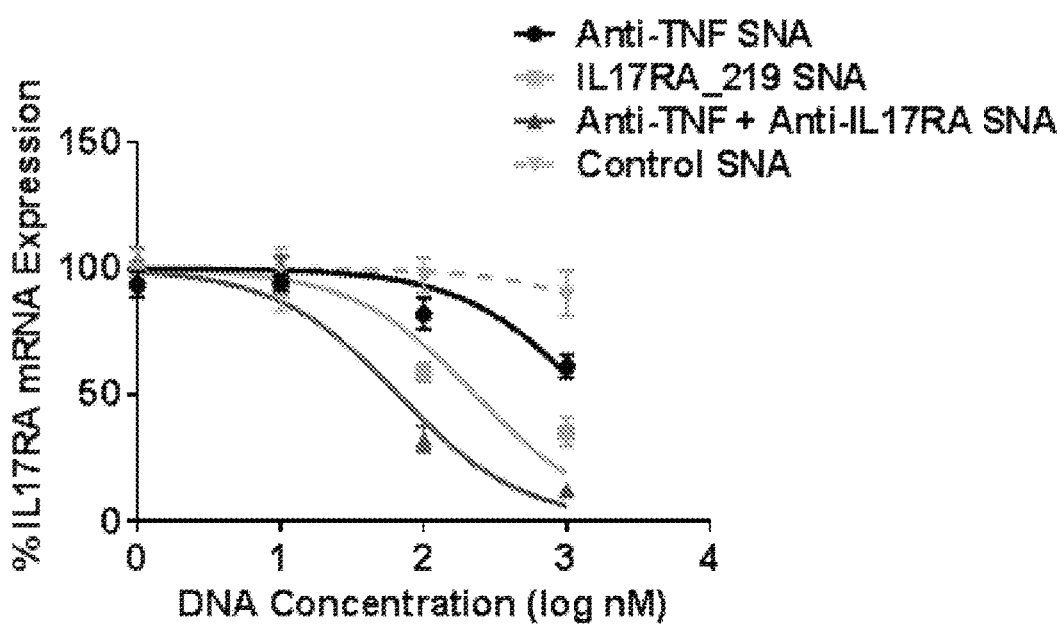
FIG. 8 shows a comparison of IL17RA mRNA knockdown using multiplexed SNAs demonstrate additive knockdown effects. IL17RA mRNA expression is decreased in HFK cells treated with anti-IL17RA-SNAs and multiplexed SNAs containing anti-TNF and anti-IL17RA ASOs. Cells treated with anti-TNF-SNAs demonstrate a slight decrease potentially due to the related biological signaling pathways of TNF and IL17RA. Greater IL17RA mRNA knockdown is observed when cells are treated with anti-IL17RA-SNAs. Multiplexed SNAs targeting both TNF and IL17RA have an additive effect and show greater knockdown of IL17RA mRNA than when SNAs targeting only anti-TNF or anti-IL17RA are used alone. Data shown are representative of at least two independent experiments performed.

When the two gene targets are in a related biological pathway, an additive knockdown effect can be observed for the downstream target (FIG. 8). TNF and IL17A cytokine signaling have been shown to have an additive and synergistic effect in their proinflammatory properties(3). This relationship indicates a shared or highly related signaling pathway, though the exact relationship is not well understood(4). The mRNA of the TNF cytokine as well as the receptor for IL17A, IL17RA were targeted. It is likely that the reduction of secreted TNF cytokine has an effect on IL17RA receptor turnover and expression.

Materials and Methods

Antisense Sequence Design. Antisense sequences, 18 nucleotides in length, targeting human IL-17RA mRNA (GeneBank Accession No. NM_014339.6) were determined based on the following parameters: Sfold Algorithm(2), % GC content, proximity to start codon, and the exclusion of CpG motifs (Table 1). Unless otherwise noted, antisense oligonucleotide sequences are divided into 3 regions: an internal, phosphorothioate linked 'gap' region flanked by two external, 2'-O-methyl 'wings'. This 'gap-mer' sequence is modified at the 3' end with two consecutive hexa(ethylene glycol) spacers and a terminal cholesterol.

Antisense oligonucleotide synthesis. All oligonucleotides were synthesized at the 1 µmole scale employing universal UnyLinker Support 1000 Å (ChemGenes) on the Bioautomation MerMade 48 oligonucleotide synthesizer. The DNA, RNA, 2'-O-Me monomers, hexa(ethylene glycol) spacers and cholesterol modifiers were obtained from ChemGenes Corporation. Coupling time was 1 minute for standard DNA bases and 3 minutes for modified bases. Linkages were either standard phosphodiesters or phosphorothioates made with 0.2 M phenylacetyl disulfide (PADS) in 1:1 lutidine: ACN as the sulfurization agent. Synthesis was performed DMT-off, in the 5' to 3' direction. After synthesis, the oligonucleotides were cleaved from the support and deprotected using a 4:1 mixture of ammonium hydroxide and ethanol at 55° C. for 16 hours. The oligonucleotides were purified via high performance liquid chromatography (HPLC) techniques. Molecular weights and extinction coefficients were determined using IDT OligoAnalyzer. Verification of oligonucleotide molecular weight was performed using matrix-assisted laser desorption/ionization (MALDI). Oligonucleotide concentration was determined by UV-absorbance at 260 nm on a microplate reader (BioTek) together with the calculated extinction coefficient from the IDT OligoAnalyzer. All oligonucleotides were sterile filtered using 0.2 µm syringe filters (VWR). The oligonucleotide sequences are listed in Table 1.

Liposome synthesis. Liposomes were synthesized by extrusion of 1,2-dioleoyl-sn-glycero-3-phosphocholine (DOPC) hydrated in phosphate buffered saline solution (PBS) (137 mM NaCl, 10 mM phosphate, 2.7 mM KCl, pH 7.4, Hyclone) using 47 mm diameter polycarbonate membranes with 50 nm pores (Sterlitech). Liposome diameters were measured using dynamic light scattering using a Malvern Zetasizer Nano (Malvern Instruments). Lipid concentration was determined using a phospholipid assay kit (Sigma).

Cell Culture. Human neonatal foreskin keratinocytes (HFKs) and adult human epidermal keratinocytes (HEKa) were cultured in M154 media (Life Technologies) supplemented with Human Keratinocyte Growth Supplement (Life Technologies), 0.07 mM $CaCl_2$, 10 µg/mL gentamicin, and 0.25m/mL amphotericin B. Cells were maintained at 37° C. in a 5% $CO_2$ humidified incubator. Fresh primary human peripheral blood mononuclear cells (PBMCs) from four different donors (Zenbio) were cultured in RPMI supplemented with 10% fetal bovine serum, 2 mM L-glutamine, 50 U/mL penicillin, and 50 mg/mL streptomycin. Cells were maintained at 37° C. in a 5% $CO_2$ humidified incubator.

EpiDerm-FT™ Human Skin Equivalent Culture. The human skin equivalent model, EpiDerm-FT™ (Mattek), tissues were cultured according to the manufacturer's instructions. Briefly, upon receipt, tissues were incubated overnight with supplied maintenance media at 37° C. in a 5% $CO_2$ humidified incubator. The following day, and every day after that for the length of the experiment, the media was replaced with fresh media. The tissues were maintained at 37° C. in a 5% $CO_2$ humidified incubator throughout the length of the experiment.

Human Skin Explant Culture. Fresh human skin explant (Zenbio) was cleaned upon receipt. 8 mm punch biopsies were taken from the explant and placed into trans-well stands for culturing. DMEM supplemented with 2% FBS, 10 μg/mL gentamicin, and 0.25 μg/mL amphotericin B was supplied to the underside of the biopsies and changed every day for the length of the experiment. The biopsies were maintained at 37° C. in a 5% $CO_2$ humidified incubator throughout the length of the experiment.

SNA Synthesis. SNAs were formulated by mixing a 100× molar excess (unless otherwise stated) of cholesterol-modified oligonucleotide to a liposome suspension in PBS and storing them overnight, protected from light, at 4° C. 294 different oligonucleotides (Table 1) were used for the synthesis process, specifically targeting human IL-17RA mRNA, and a control oligonucleotide of the same length and 'gap-mer' chemical scheme that does not have any complementarity to known human genes (confirmed by BLAST).

Figure 6A:
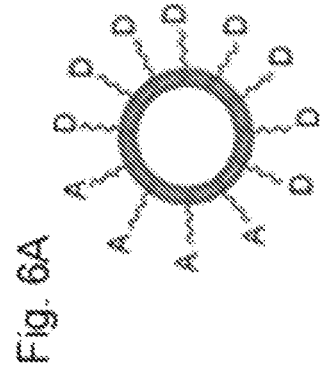
FIGS. 6A-6D show configurations of multiplexed SNAs. Liposomes were surface-functionalized in the following configurations.
Figure 6B:
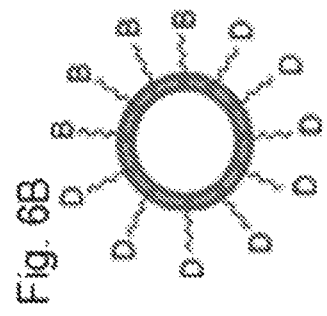
Figure 6C:
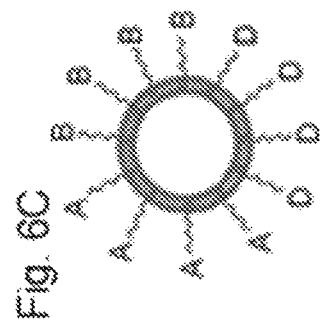
Figure 6D:
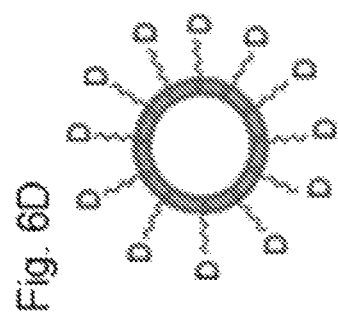

Multiplex SNA Synthesis. SNAs were formulated by mixing a 200× molar excess (unless otherwise stated) of cholesterol-modified oligonucleotide to a liposome suspension in PBS and storing them overnight, protected from light, at 4° C. Four different oligonucleotides were used for the synthesis process: an antisense oligonucleotide targeting human IL-17RA, an antisense oligonucleotide targeting human TNF, an antisense oligonucleotide targeting human IL22RA1, and a same length control oligonucleotide that does not have any complementarity to known genes (confirmed by BLAST). For monoplex SNAs, the oligonucleotide population consisted of 33% targeted antisense oligonucleotide and 66% control oligonucleotide. For multiplex SNAs containing two different targeted antisense oligonucleotides, the oligonucleotide population consisted of 33% of each targeted antisense oligonucleotide and the remaining 33% control oligonucleotide (FIG. 6). For multiplex SNAs containing three different targeted antisense oligonucleotides, the oligonucleotide population consisted of 33% of each targeted antisense oligonucleotide. Control SNAs consisted of 100% of the control oligonucleotide (FIG. 6D).

Cell Culture Studies. HFKs were seeded at passage 5 in 96-well, tissue culture plates at a cell density of 17,000 cells per well. HEKa cells were seeded at passage 5 in 96-well, tissue culture plates at a cell density of 17,000 cells per well. Fresh PBMCs were isolated from cell suspension by centrifugation and seeded in 96-well, tissue culture plates at a cell density of 200,000 cells per well. Cells were allowed to rest in the incubator overnight following plating. Cells were treated with either an IL-17RA targeted antisense SNA or a non-complementary control SNA (confirmed by NCBI Blast), comprising the same 'gap-mer' design and 3'-chemical modifications, in fresh maintenance media. Unless otherwise stated, all treatments lasted 24 hours.

For the human skin equivalent model, EpiDerm-FT™, and human skin explant tissues, treatments were applied in biological triplicate. Tissues were treated topically with either an SNA presenting the IL17RA_219 ASO, an SNA presenting the IL17RA_282 ASO, an SNA presenting the non-complementary control ASO or left untreated. The EpiDerm-FT™ tissues were treated for 48 hours and the human skin explant tissues were treated for 96 hours.

For multiplex SNA experiments, HFKs were seeded at passage 5 in 96-well, tissue culture plates at a cell density of 17,000 cells per well. Cells were allowed to rest in the incubator overnight following plating. Cells were treated in triplicate with either an IL-17RA targeted antisense SNA, TNF targeted antisense SNA, a multiplex SNA targeting more than one transcript or a non-complementary control SNA (confirmed by NCBI Blast), comprising the same 'gap-mer' design and 3'-chemical modifications, at concentrations of 1000, 100, 10 and 1 nM in fresh maintenance media.

Alamar Blue® Viability Assay. For viability studies, HFKs were seeded at passage 5 in 96-well, tissue culture plates at a cell density of 15,000 cells per well. Cells were allowed to rest in the incubator overnight following plating. Cells were treated in triplicate with either an IL-17RA targeted antisense SNA or a non-complementary control (confirmed by NCBI Blast), comprising the same 'gap-mer' design and 3' chemical modifications, at concentrations of 20, 10, 2 and 1 μM for 24 hours. Briefly, treatments were removed and replace with a 10% solution of AlamarBlue® reagent in M154 maintenance media. Cells were incubated at 37° C. for 3 hours in a 5% $CO_2$ humidified incubator before measuring the fluorescence of each well (excitation 570 nm, emission 585 nm) with a microplate reader (BioTek). Percent viability was calculated by comparing fluorescent values of each treatment to those of the untreated cells.

Cytokine Q-Plex Array. After 24 hours of treatment, the cells in the 96-well tissue culture plates were pelleted by centrifugation; the supernatants were transferred to new plates and stored at −80° C. Cytokine quantification of the supernatants was performed using a Q-Plex chemiluminescent array (Quansys) following the manufacturer's instructions. Each plate was custom built to allow for the detection of IL-12p40, TNF, IP-10, IL-6, RANTES, IL-4, IL-5, IL-10, IL-17, IL-22 and MCP-1 within each well. Briefly, a standard curve was prepared using a cytokine stock of known concentration and diluting it as indicated. The cell culture supernatants were diluted 1:2 using the provided sample buffer. The cell culture samples and standard curve samples were added to the 96-well Q-plex plate and incubated at room temperature for 1 hour with shaking. The plate was then washed three times with the provided wash buffer. Then 50 μL of provided Detection mix was added to each well and the plate was incubated again for 1 hour at room temperature with shaking. Again, the plate was washed three times with wash buffer, followed by incubation with 50 μL of provided Streptavidin-HRP solution for 15 minutes at room temperature with shaking. Finally, the plate was washed six times in wash buffer and 50 μL of a prepared substrate was added to each well. Within 15 minutes, the plate was imaged using a Bio-Rad ChemiDoc XRS+ imager and analyzed using the Q-view software (Quansys). All data was fit to the standard curves for each individual cytokine and plotted in comparison to untreated cells.

RNA Extraction and Quantitative Reverse Transcriptase Polymerase Chain Reaction (qRT-PCR). HFK and HEKa cells were lysed in RLT Buffer (Qiagen) at 24 hours post-transfection. EpiDerm-FT™ tissues and human skin explant tissues were bead homogenized in RLT buffer at 48 and 96 hours of treatment, respectively. RNA was isolated from lysates using the RNEasy 96-well kit (Qiagen) according to the manufacturer's instructions. cDNA was then synthesized from RNA isolates using the cDNA High Capacity Reverse Transcription Kit (Life Technologies). Samples were run on a thermocycler at 25° C. for 10 minutes, 37° C. for 90 minutes, 85° C. for 5 minutes and held at 4° C. to generate cDNA. qPCR was performed using 6 μL of the synthesized cDNA, 4.66 μL LightCycler480 Probes Master Mix (Roche), 0.47 μL target specific FAM-labeled probe and primers, and 0.37 μL human Glyceraldehyde-3-phosphate dehydrogenase (GAPDH) specific HEX-labeled probe and primers per reaction well of a 384-well optical reaction plate (Roche). The primer and probe sets for IL-17RA were purchased from ThermoFisher Scientific (catalogue number Hs01064648_m1). The primer and probe sets for TNF and GAPDH were designed using the known human genome sequence (NCBI reference sequences NM_000594.3 and NM_002046.5, respectively) and were found to be specific by "blastn" analysis (NCBI). The oligonucleotide sequences used for TNF were: forward 5'-GCT GCA CTT TGG AGT GAT CG-3' (SEQ ID NO: 1), reverse 5'-GTT TGC TAC AAC ATG GGC TAC AG-3' (SEQ ID NO: 2), probe 5'-FAM-CCC AGG CAG TCA GAT CAT CTT CTC GA-BHQ1-3' (SEQ ID NO: 3). The oligonucleotide sequences used for GAPDH were: forward 5'-CAA GGT CAT CCA TGA CAA CTT TG-3' (SEQ ID NO: 4), reverse 5'-GGG CCA TCC ACA GTC TTC T-3' (SEQ ID NO: 5), probe 5'-HEX-ACC ACA GTC CAT GCC ATC ACT GCC A-BHQ1-3' (SEQ ID NO: 6). FAM is 6-fluorescein amidite, HEX is hexachloro-fluorescein, and BHQ1 is a black hole quencher 1. qPCR reactions, in technical duplicate, were carried out on the Roche Lightcycler 480 under the following conditions: initial denaturation at 95° C. for 10 minutes and then 50 cycles of denaturation at 95° C. for 10 seconds, annealing at 60° C. for 30 seconds and extension at 72° C. for 1 second. Cp values were obtained by analysis with the 2nd derivative method. Relative gene expression was determined by normalization with the housekeeping gene (GAPDH) and the ΔΔ-Ct method. Each treatment was compared to its respective concentration control.

TABLE 1

Oligonucleotide Sequences
Special bases used in the oligonucleotides are as follows: mN = 2' O-methyl RNA, /iSp18/ = hexa(ethylene glycol) spacer, * = phosphorothioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_001 | mUmCmGmCmGmGA*G*G*G*C*T*mCmGm GmCmCmC/iSp18//iSp18//3CholTEG/ | 7 | 67 |
| IL17RA_002 | mGmUmCmGmCmGG*A*G*G*G*C*mUmCm GmCmCmC/iSp18//iSp18//3CholTEG/ | 8 | 35 |
| IL17RA_003 | mCmGmUmCmGmCG*G*A*G*G*G*mCmUm CmGmCmC/iSp18//iSp18//3CholTEG/ | 9 | 36 |
| IL17RA_004 | mAmCmGmGmCmGG*G*C*T*G*C*mGmUm GmCmGmG/iSp18//iSp18//3CholTEG/ | 10 | 49 |
| IL17RA_005 | mGmAmCmGmGmCG*G*G*C*T*G*mCmGm UmGmCmG/iSp18//iSp18//3CholTEG/ | 11 | 40 |
| IL17RA_006 | mAmCmUmCmUmGC*A*C*C*C*T*mCmGm AmGmGmU/iSp18//iSp18//3CholTEG/ | 12 | 35 |
| IL17RA_007 | mGmGmGmCmUmGC*C*C*A*G*C*mAmGm CmGmGmG/iSp18//iSp18//3CholTEG/ | 13 | 30 |
| IL17RA_008 | mUmGmUmGmUmGG*G*T*C*T*G*mUmGm AmGmGmA/iSp18//iSp18//3CholTEG/ | 14 | 73 |
| IL17RA_009 | mGmGmCmGmUmGT*G*T*G*G*G*mUmCm UmGmUmG/iSp18//iSp18//3CholTEG/ | 15 | 43 |
| IL17RA_010 | mGmGmGmCmGmUG*T*G*T*G*G*mGmUm CmUmGmU/iSp18//iSp18//3CholTEG/ | 16 | 35 |
| IL17RA_011 | mAmGmGmGmCmGT*G*T*G*T*G*mGmGm UmCmUmG/iSp18//iSp18//3CholTEG/ | 17 | 54 |
| IL17RAv012 | mUmAmGmGmGmCG*T*G*T*G*T*mGmGm GmUmCmU/iSp18//iSp18//3CholTEG/ | 18 | 49 |
| IL17RA_013 | mAmGmCmUmCmCT*G*G*A*G*A*mUmGm UmAmGmC/iSp18//iSp18//3CholTEG/ | 19 | 38 |
| IL17RA_014 | mGmAmGmCmUmCC*T*G*G*A*G*mAmUm GmUmAmG/iSp18//iSp18//3CholTEG/ | 20 | 49 |
| IL17RA_015 | mGmGmAmGmCmUC*C*T*G*G*A*mGmAm UmGmUmA/iSp18//iSp18//3CholTEG/ | 21 | 88 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_016 | mCmCmCmUmCmGG*G*G*G*C*mUmGm CmGmGmG/iSp18//iSp18//3CholTEG/ | 22 | 91 |
| IL17RA_017 | mGmGmGmAmGmAG*A*G*T*G*mCmAm GmGmGmC/iSp18//iSp18//3CholTEG/ | 23 | 105 |
| IL17RA_018 | mCmGmGmGmAmGA*G*A*G*T*G*mGmCm AmGmGmG/iSp18//iSp18//3CholTEG/ | 24 | 106 |
| IL17RA_019 | mAmCmGmAmUmAA*C*C*A*G*A*mCmCm GmCmUmG/iSp18//iSp18//3CholTEG/ | 25 | 103 |
| IL17RA_020 | mGmGmGmAmGmCG*G*G*C*T*G*mUmGm UmGmGmA/iSp18//iSp18//3CholTEG/ | 26 | 77 |
| IL17RA_021 | mAmCmAmUmAmGT*A*G*G*T*G*mCmAm CmAmAmU/iSp18//iSp18//3CholTEG/ | 27 | 81 |
| IL17RA_022 | mCmAmCmAmUmAG*T*A*G*G*T*mGmCm AmCmAmA/iSp18//iSp18//3CholTEG/ | 28 | 76 |
| IL17RA_023 | mGmGmGmUmCmUC*A*C*T*C*T*mGmCm UmCmCmC/iSp18//iSp18//3CholTEG/ | 29 | 57 |
| IL17RA_024 | mGmGmGmCmAmGG*C*T*T*C*C*mAmCm UmCmCmA/iSp18//iSp18//3CholTEG/ | 30 | 43 |
| IL17RA_025 | mAmAmAmGmCmUG*T*T*A*G*G*mAmGm GmAmCmA/iSp18//iSp18//3CholTEG/ | 31 | 77 |
| IL17RA_026 | mUmAmAmAmGmCT*G*T*T*A*G*mGmAm GmGmAmC/iSp18//iSp18//3CholTEG/ | 32 | 75 |
| IL17RA_027 | mAmUmAmAmAmGC*T*G*T*T*A*mGmGm AmGmGmA/iSp18//iSp18//3CholTEG/ | 33 | 91 |
| IL17RA_028 | mAmCmCmGmGmCA*T*C*A*A*A*mUmUm GmUmGmC/iSp18//iSp18//3CholTEG/ | 34 | 87 |
| IL17RA_029 | mAmAmCmCmGmGC*A*T*C*A*A*mAmUm UmGmUmG/iSp18//iSp18//3CholTEG/ | 35 | 93 |
| IL17RA_030 | mCmUmGmGmAmUT*T*C*T*T*T*mUmGm GmGmGmG/iSp18//iSp18//3CholTEG/ | 36 | 64 |
| IL17RA_031 | mGmCmUmGmGmAT*T*T*C*T*T*mUmUm GmGmGmG/iSp18//iSp18//3CholTEG/ | 37 | 53 |
| IL17RA_032 | mGmGmCmUmGmGA*T*T*T*C*T*mUmUm UmGmGmG/iSp18//iSp18//3CholTEG/ | 38 | 38 |
| IL17RA_033 | mGmGmGmCmUmGG*A*T*T*T*C*mUmUm UmUmGmG/iSp18//iSp18//3CholTEG/ | 39 | 41 |
| IL17RA_034 | mGmGmGmGmCmUG*G*A*T*T*T*mCmUm UmUmUmG/iSp18//iSp18//3CholTEG/ | 40 | 77 |
| IL17RA_035 | mGmGmGmAmGmGG*A*A*T*G*T*mGmAm GmGmAmG/iSp18//iSp18//3CholTEG/ | 41 | 58 |
| IL17RA_036 | mGmCmUmGmAmAG*A*G*T*G*mGmGm AmGmGmG/iSp18//iSp18//3CholTEG/ | 42 | 49 |
| IL17RA_037 | mGmAmGmCmCmUG*G*A*G*G*mUmCm GmAmGmG/iSp18//iSp18//3CholTEG/ | 43 | 40 |
| IL17RA_038 | mGmGmGmAmGmGA*T*G*A*G*G*mCmGm GmGmCmA/iSp18//iSp18//3CholTEG/ | 44 | 39 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_039 | mUmGmGmGmAmGG*A*T*G*A*G*mGmCmGmGmGmC/iSp18//iSp18//3CholTEG/ | 45 | 31 |
| IL17RA_040 | mUmUmUmAmGmGA*A*G*G*G*G*mAmGmCmAmCmC/iSp18//iSp18//3CholTEG/ | 46 | 60 |
| IL17RA_041 | mAmUmUmUmAmGG*A*A*G*G*G*mGmAmGmCmAmC/iSp18//iSp18//3CholTEG/ | 47 | 57 |
| IL17RA_042 | mUmAmUmUmUmAG*G*A*A*G*G*mGmGmAmGmCmA/iSp18//iSp18//3CholTEG/ | 48 | 57 |
| IL17RA_043 | mUmUmAmUmUmUA*G*G*A*A*G*mGmGmAmGmC/iSp18//iSp18//3CholTEG/ | 49 | 23 |
| IL17RA_044 | mCmAmUmUmUmAT*T*T*A*G*G*mAmAmGmGmGmG/iSp18//iSp18//3CholTEG/ | 50 | 38 |
| IL17RA_045 | mUmCmAmUmUmUA*T*T*T*A*G*mGmAmAmGmGmG/iSp18//iSp18//3CholTEG/ | 51 | 35 |
| IL17RA_046 | mGmGmGmAmUmGC*A*G*G*C*C*mCmGmGmCmUmG/iSp18//iSp18//3CholTEG/ | 52 | 53 |
| IL17RA_047 | mAmAmAmGmAmGG*A*T*C*A*G*mUmGmGmUmAmC/iSp18//iSp18//3CholTEG/ | 53 | 71 |
| IL17RA_048 | mGmAmAmAmGmAG*G*A*T*C*A*mGmUmGmGmUmA/iSp18//iSp18//3CholTEG/ | 54 | 42 |
| IL17RA_049 | mUmGmGmGmUmUT*A*G*G*G*G*mUmAmGmCmUmG/iSp18//iSp18//3CholTEG/ | 55 | 48 |
| IL17RA_050 | mAmUmGmGmGmUT*T*A*G*G*G*mGmUmAmGmCmU/iSp18//iSp18//3CholTEG/ | 56 | 43 |
| IL17RA_051 | mAmAmUmGmGmGT*T*T*A*G*G*mGmGmUmAmGmC/iSp18//iSp18//3CholTEG/ | 57 | 64 |
| IL17RA_052 | mUmGmCmAmAmUG*G*G*T*T*T*mAmGmGmGmGmU/iSp18//iSp18//3CholTEG/ | 58 | 58 |
| IL17RA_053 | mGmUmGmCmAmAT*G*G*G*T*T*mUmAmGmGmGmG/iSp18//iSp18//3CholTEG/ | 59 | 64 |
| IL17RA_054 | mUmGmUmGmCmAA*T*G*G*G*T*mUmUmAmGmGmG/iSp18//iSp18//3CholTEG/ | 60 | 79 |
| IL17RA_055 | mUmUmGmUmGmCA*A*T*G*G*G*mUmUmUmAmGmG/iSp18//iSp18//3CholTEG/ | 61 | 73 |
| IL17RA_056 | mCmUmUmGmUmGC*A*A*T*G*G*mGmUmUmUmAmG/iSp18//iSp18//3CholTEG/ | 62 | 64 |
| IL17RA_057 | mGmCmUmUmGmUG*C*A*A*T*G*mGmGmUmUmUmA/iSp18//iSp18//3CholTEG/ | 63 | 77 |
| IL17RA_058 | mAmGmCmUmUmGT*G*C*A*A*T*mGmGmGmUmUmU/iSp18//iSp18//3CholTEG/ | 64 | 11 |
| IL17RA_059 | mCmAmGmCmUmUG*T*G*C*A*A*mUmGmGmGmUmU/iSp18//iSp18//3CholTEG/ | 65 | 75 |
| IL17RA_060 | mGmGmGmCmAmUG*G*A*G*A*G*mCmCmAmUmGmC/iSp18//iSp18//3CholTEG/ | 66 | 52 |
| IL17RA_061 | mUmCmUmGmGmGA*G*A*G*C*mGmAmUmGmGmG/iSp18//iSp18//3CholTEG/ | 67 | 47 |

TABLE 1-continued

Oligonucleotide Sequences
Special bases used in the oligonucleotides are as follows: mN = 2' O-methyl RNA, /iSp18/ = hexa(ethylene glycol) spacer, * = phosphorothioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_062 | mGmGmGmAmGmGT*G*G*C*T*mGmGm GmCmCmA/iSp18//iSp18//3CholTEG/ | 68 | 59 |
| IL17RA_063 | mAmCmUmCmCmCT*C*T*C*C*T*mCmCm UmCmCmU/iSp18//iSp18//3CholTEG/ | 69 | 44 |
| IL17RA_064 | mUmAmCmUmCmCC*T*C*T*C*C*mUmCm CmUmCmC/iSp18//iSp18//3CholTEG/ | 70 | 29 |
| IL17RA_065 | mGmGmGmAmGmGC*A*A*G*T*mCmUm GmAmGmA/iSp18//iSp18//3CholTEG/ | 71 | 60 |
| IL17RA_066 | mUmCmAmGmGmGC*A*G*C*C*C*mGmGm GmAmGmG/iSp18//iSp18//3CholTEG/ | 72 | 64 |
| IL17RA_067 | mCmAmCmUmCmCA*C*T*C*A*C*mCmUm CmCmCmA/iSp18//iSp18//3CholTEG/ | 73 | 16 |
| IL17RA_068 | mGmGmGmUmGmCA*G*G*G*C*T*mUmCm AmGmAmC/iSp18//iSp18//3CholTEG/ | 74 | 26 |
| IL17RA_069 | mGmCmGmGmGmUG*C*A*G*G*mCmUm UmCmAmG/iSp18//iSp18//3CholTEG/ | 75 | 40 |
| IL17RA_070 | mCmUmGmUmUmUG*C*T*C*T*C*mCmUm GmUmCmA/iSp18//iSp18//3CholTEG/ | 76 | 22 |
| IL17RA_071 | mCmCmUmGmUmUT*G*C*T*C*T*mCmCm UmGmUmC/iSp18//iSp18//3CholTEG/ | 77 | 61 |
| IL17RA_072 | mUmCmCmUmGmUT*T*G*C*T*C*mUmCm CmUmGmU/iSp18//iSp18//3CholTEG/ | 78 | 51 |
| IL17RA_073 | mGmUmCmCmUmGT*T*T*G*C*T*mCmUm CmCmUmG/iSp18//iSp18//3CholTEG/ | 79 | 46 |
| IL17RA_074 | mUmGmUmCmCmUG*T*T*T*G*C*mUmCm UmCmCmU/iSp18//iSp18//3CholTEG/ | 80 | 45 |
| IL17RA_075 | mCmUmGmUmCmCT*G*T*T*T*G*mCmUm CmUmCmC/iSp18//iSp18//3CholTEG/ | 81 | 52 |
| IL17RA_076 | mGmGmCmUmAmGT*G*G*C*T*G*mGmGm AmGmGmC/iSp18//iSp18//3CholTEG/ | 82 | 70 |
| IL17RA_077 | mGmGmAmAmUmGG*G*A*G*C*A*mGmA mUmGmGmG/iSp18//iSp18//3CholTEG/ | 83 | 63 |
| IL17RA_078 | mGmGmGmCmUmUG*G*G*C*A*G*mGmU mGmGmUmG/iSp18//iSp18//3CholTEG/ | 84 | 32 |
| IL17RA_079 | mGmGmGmAmUmGG*G*C*T*T*G*mGmGm CmAmGmG/iSp18//iSp18//3CholTEG/ | 85 | 42 |
| IL17RA_080 | mGmGmUmCmUmCC*A*C*G*T*mGmGmAm UmGmUmU/iSp18//iSp18//3CholTEG/ | 86 | 30 |
| IL17RA_081 | mGmUmAmAmUmGG*G*T*A*G*A*mUmU mCmGmUmU/iSp18//iSp18//3CholTEG/ | 87 | 22 |
| IL17RA_082 | mGmGmUmAmAmUG*G*T*A*G*mAmU mUmCmGmU/iSp18//iSp18//3CholTEG/ | 88 | 40 |
| IL17RA_083 | mUmGmGmUmAmAT*G*G*T*A*mGmAm UmUmCmG/iSp18//iSp18//3CholTEG/ | 89 | 35 |
| IL17RA_084 | mCmUmGmGmUmAA*T*G*G*T*mAmGm AmUmUmC/iSp18//iSp18//3CholTEG/ | 90 | 37 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_085 | mGmGmCmCmGmCA*G*G*T*A*T*mGmUm GmGmUmG/iSp18//iSp18//3CholTEG/ | 91 | 55 |
| IL17RA_086 | mGmGmCmUmGmAG*T*A*G*A*T*mGmAm UmCmCmA/iSp18//iSp18//3CholTEG/ | 92 | 65 |
| IL17RA_087 | mCmGmCmGmCmCG*A*A*C*A*G*mGmUm CmGmGmG/iSp18//iSp18//3CholTEG/ | 93 | 63 |
| IL17RA_088 | mGmUmAmGmAmGG*T*T*C*T*C*mAmCm AmUmUmC/iSp18//iSp18//3CholTEG/ | 94 | 57 |
| IL17RA_089 | mCmCmGmCmCmCG*G*G*C*T*C*mCmGm CmAmGmG/iSp18//iSp18//3CholTEG/ | 95 | 83 |
| IL17RA_090 | mCmCmCmUmGmGG*C*A*G*G*C*mUmUm CmCmAmC/iSp18//iSp18//3CholTEG/ | 96 | 67 |
| IL17RA_091 | mCmAmAmUmGmGG*T*T*T*A*G*mGmGm GmUmAmG/iSp18//iSp18//3CholTEG/ | 97 | 66 |
| IL17RA_092 | mGmCmAmAmUmGG*G*T*T*T*A*mGmGm GmGmUmA/iSp18//iSp18//3CholTEG/ | 98 | 64 |
| IL17RA_093 | mGmGmAmGmGmAT*G*A*G*G*C*mGmGm GmCmAmG/iSp18//iSp18//3CholTEG/ | 99 | 68 |
| IL17RA_094 | mGmUmGmCmGmGC*C*C*C*C*A*mUmGm GmCmCmC/isp18//isp18//3CholTEG/ | 100 | 79 |
| IL17RA_095 | mCmGmUmGmCmGG*C*C*C*C*C*mAmUm GmGmCmC/isp18//isp18//3CholTEG/ | 101 | 74 |
| IL17RA_096 | mGmCmGmUmGmCG*G*C*C*C*C*mCmAm UmGmGmC/isp18//isp18//3CholTEG/ | 102 | 72 |
| IL17RA_097 | mUmGmCmGmUmGC*G*G*C*C*C*mCmCm AmUmGmG/isp18//isp18//3CholTEG/ | 103 | 77 |
| IL17RA_098 | mCmUmGmCmGmUG*C*G*G*C*C*mCmCm CmAmUmG/isp18//isp18//3CholTEG/ | 104 | 58 |
| IL17RA_099 | mCmGmGmGmCmUG*C*G*T*G*C*mGmGm CmCmCmC/isp18//isp18//3CholTEG/ | 105 | 83 |
| IL17RA_100 | mGmCmGmGmGmCT*G*C*G*T*G*mCmGm GmCmCmC/isp18//isp18//3CholTEG/ | 106 | 84 |
| IL17RA_101 | mGmGmCmGmGmGC*T*G*C*G*T*mGmCm GmGmCmC/isp18//isp18//3CholTEG/ | 107 | 75 |
| IL17RA_102 | mUmCmGmCmAmGG*G*A*G*G*C*mGmCm CmAmCmC/isp18//isp18//3CholTEG/ | 108 | 87 |
| IL17RA_103 | mGmUmCmGmCmAG*G*G*A*G*G*mCmGm CmCmAmC/isp18//isp18//3CholTEG/ | 109 | 72 |
| IL17RA_104 | mUmUmCmGmAmUG*T*G*A*G*C*mCmAm CmGmGmG/isp18//isp18//3CholTEG/ | 110 | 74 |
| IL17RA_105 | mCmCmAmUmUmCG*A*T*G*T*G*mAmGm CmCmAmC/isp18//isp18//3CholTEG/ | 111 | 76 |
| IL17RA_106 | mGmAmUmAmAmCT*C*T*G*C*A*mCmCm CmCmCmG/isp18//isp18//3CholTEG/ | 112 | 84 |
| IL17RA_107 | mGmGmCmUmUmGG*G*C*A*G*G*mUmG mGmUmGmA/isp18//isp18//3CholTEG/ | 113 | 65 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_108 | mUmGmGmGmCmUT*G*G*G*C*A*mGmGm UmGmGmU/isp18//isp18//3CholTEG/ | 114 | 37 |
| IL17RA_109 | mAmAmUmGmGmGT*A*G*A*T*T*mCmGm UmUmCmC/isp18//isp18//3CholTEG/ | 115 | 44 |
| IL17RA_110 | mUmAmAmUmGmGG*T*A*G*A*T*mUmCm GmUmUmC/isp18//isp18//3CholTEG/ | 116 | 62 |
| IL17RA_111 | mUmCmCmCmCmCG*C*C*A*G*T*mGmCm CmAmGmC/isp18//isp18//3CholTEG/ | 117 | 57 |
| IL17RA_112 | mCmCmCmUmCmUG*A*C*T*C*T*mGmAm CmCmCmC/isp18//isp18//3CholTEG/ | 118 | 57 |
| IL17RA_113 | mGmGmGmCmCmCC*T*C*T*G*A*mCmUm CmUmGmA/isp18//isp18//3CholTEG/ | 119 | 85 |
| IL17RA_114 | mUmGmGmGmCmCC*C*T*C*T*G*mAmCm UmCmUmG/isp18//isp18//3CholTEG/ | 120 | 76 |
| IL17RA_115 | mCmUmGmGmGmCC*C*C*T*C*T*mGmAm CmCmCmU/isp18//isp18//3CholTEG/ | 121 | 64 |
| IL17RA_116 | mAmGmGmGmUmCT*C*A*C*T*C*mUmGm CmUmGmC/isp18//isp18//3CholTEG/ | 122 | 8 |
| IL17RA_117 | mCmAmGmGmGmUC*T*C*A*C*T*mCmUm GmCmUmG/isp18//isp18//3CholTEG/ | 123 | 55 |
| IL17RA_118 | mAmCmAmGmGmGT*C*T*C*A*C*mUmCm UmGmCmU/isp18//isp18//3CholTEG/ | 124 | 59 |
| IL17RA_119 | mGmAmCmAmGmGG*T*C*T*C*A*mCmUm CmUmGmC/isp18//isp18//3CholTEG/ | 125 | 60 |
| IL17RA_120 | mAmGmAmCmAmGG*G*T*C*T*C*mAmCm UmCmUmG/isp18//isp18//3CholTEG/ | 126 | 70 |
| IL17RA_121 | mGmAmGmAmCmAG*G*G*T*C*T*mCmAm CmUmCmU/isp18//isp18//3CholTEG/ | 127 | 83 |
| IL17RA_122 | mUmGmAmGmAmCA*G*G*G*T*C*mUmCm AmCmUmC/isp18//isp18//3CholTEG/ | 128 | 78 |
| IL17RA_123 | mGmCmAmGmGmCT*T*C*C*A*C*mUmCm CmAmUmC/isp18//isp18//3CholTEG/ | 129 | 60 |
| IL17RA_124 | mCmUmCmCmAmCT*C*A*C*T*mCmCm CmAmGmC/isp18//isp18//3CholTEG/ | 130 | 62 |
| IL17RA_125 | mAmCmUmCmCmAC*T*C*A*C*C*mUmCm CmCmAmG/isp18//isp18//3CholTEG/ | 131 | 78 |
| IL17RA_126 | mGmCmUmCmAmCT*C*C*A*C*T*mCmAm CmUmCmC/isp18//isp18//3CholTEG/ | 132 | 91 |
| IL17RA_127 | mAmGmCmUmCmAC*T*C*C*A*C*mUmCm AmCmCmU/isp18//isp18//3CholTEG/ | 133 | 89 |
| IL17RA_128 | mGmAmCmAmAmGC*T*C*A*C*T*mCmCm AmCmUmC/isp18//isp18//3CholTEG/ | 134 | 86 |
| IL17RA_129 | mUmCmCmCmCmCC*A*C*C*C*C*mCmCm AmCmCmC/isp18//isp18//3CholTEG/ | 135 | 59 |
| IL17RA_130 | mAmGmGmGmCmUT*C*A*G*A*C*mUmCm AmCmCmU/isp18//isp18//3CholTEG/ | 136 | 58 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_131 | mCmAmGmGmGmCT*T*C*A*G*A*mCmUm CmAmCmC/isp18//isp18//3CholTEG/ | 137 | 65 |
| IL17RA_132 | mGmCmAmGmGmGC*T*T*C*A*G*mAmCm UmCmAmC/isp18//isp18//3CholTEG/ | 138 | 51 |
| IL17RA_133 | mUmGmCmAmGmGG*C*T*T*C*A*mGmAm CmUmCmA/isp18//isp18//3CholTEG/ | 139 | 57 |
| IL17RA_134 | mGmUmGmCmAmGG*G*C*T*T*C*mAmGm AmCmUmC/isp18//isp18//3CholTEG/ | 140 | 84 |
| IL17RA_135 | mCmGmGmGmUmGC*A*G*G*G*C*mUmUm CmAmGmA/isp18//isp18//3CholTEG/ | 141 | 66 |
| IL17RA_136 | mCmGmCmGmGmGT*G*C*A*G*G*mGmCm UmUmCmA/isp18//isp18//3CholTEG/ | 142 | 43 |
| IL17RA_137 | mAmCmGmCmGmGG*T*G*C*A*G*mGmGm CmUmUmC/isp18//isp18//3CholTEG/ | 143 | 39 |
| IL17RA_138 | mAmAmCmGmCmGG*G*T*G*C*A*mGmGm GmCmUmU/isp18//isp18//3CholTEG/ | 144 | 51 |
| IL17RA_139 | mGmAmAmCmGmCG*G*G*T*G*C*mAmGm GmGmCmU/isp18//isp18//3CholTEG/ | 145 | 59 |
| IL17RA_140 | mCmUmCmUmCmCT*G*T*C*A*C*mAmUm UmUmCmC/isp18//isp18//3CholTEG/ | 146 | 55 |
| IL17RA_141 | mGmCmUmCmUmCC*T*G*T*C*A*mCmAm UmUmUmC/isp18//isp18//3CholTEG/ | 147 | 58 |
| IL17RA_142 | mUmGmCmUmCmUC*C*T*G*T*C*mAmCm AmUmUmU/isp18//isp18//3CholTEG/ | 148 | 59 |
| IL17RA_143 | mUmUmGmCmUmCT*C*C*T*G*T*mCmAm CmAmUmU/isp18//isp18//3CholTEG/ | 149 | 53 |
| IL17RA_144 | mUmUmUmGmCmUC*T*C*C*T*G*mUmCm AmCmAmU/isp18//isp18//3CholTEG/ | 150 | 51 |
| IL17RA_145 | mGmUmUmUmGmCT*C*T*C*C*T*mGmUm CmAmCmA/isp18//isp18//3CholTEG/ | 151 | 56 |
| IL17RA_146 | mUmGmUmUmUmGC*T*C*T*C*C*mUmGm UmCmAmC/isp18//isp18//3CholTEG/ | 152 | 53 |
| IL17RA_147 | mCmCmUmGmUmUT*G*C*T*C*T*mCmCm UmGmUmC/isp18//isp18//3CholTEG/ | 153 | 71 |
| IL17RA_148 | mAmGmCmUmGmAA*G*A*G*T*mGmGm GmAmGmG/isp18//isp18//3CholTEG/ | 154 | 64 |
| IL17RA_149 | mGmAmGmCmUmGA*A*G*A*G*mUmG mGmGmAmG/isp18//isp18//3CholTEG/ | 155 | 73 |
| IL17RA_150 | mCmGmAmGmCmUG*A*A*G*A*G*mGmU mGmGmGmA/isp18//isp18//3CholTEG/ | 156 | 64 |
| IL17RA_151 | mAmCmGmAmGmCT*G*A*A*G*A*mGmGm UmGmGmG/isp18//isp18//3CholTEG/ | 157 | 86 |
| IL17RA_152 | mGmGmCmAmGmGC*T*T*C*A*mCmUm CmCmAmU/isp18//isp18//3CholTEG/ | 158 | 66 |
| IL17RA_153 | mUmGmGmGmCmAG*G*C*T*T*C*mCmAm CmUmCmC/isp18//isp18//3CholTEG/ | 159 | 63 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_154 | mCmUmGmGmCA*G*G*C*T*T*mCmCmAmCmUmC/isp18//isp18//3CholTEG/ | 160 | 42 |
| IL17RA_155 | mCmCmUmGmGmGC*A*G*G*C*T*mUmCmCmAmCmU/isp18//isp18//3CholTEG/ | 161 | 45 |
| IL17RA_156 | mCmCmAmCmCmUC*T*G*C*A*C*mAmCmUmCmAmG/isp18//isp18//3CholTEG/ | 162 | 77 |
| IL17RA_157 | mGmCmCmUmGmGG*A*G*G*T*C*mGmAmGmGmCmU/isp18//isp18//3CholTEG/ | 163 | 64 |
| IL17RA_158 | mAmGmCmCmUmGG*G*A*G*G*T*mCmGmAmGmGmC/isp18//isp18//3CholTEG/ | 164 | 71 |
| IL17RA_159 | mUmGmAmGmCmCT*G*G*G*A*G*mGmUmCmGmAmG/isp18//isp18//3CholTEG/ | 165 | 80 |
| IL17RA_160 | mUmUmGmAmGmCC*T*G*G*G*A*mGmGmUmCmGmA/isp18//isp18//3CholTEG/ | 166 | 95 |
| IL17RA_161 | mCmUmUmGmAmGC*C*T*G*G*G*mAmGmGmUmCmG/isp18//isp18//3CholTEG/ | 167 | 92 |
| IL17RA_162 | mUmUmGmGmGmAG*G*A*T*G*A*mGmGmCmGmGmG/isp18//isp18//3CholTEG/ | 168 | 78 |
| IL17RA_163 | mUmUmUmGmGmGA*G*G*A*T*G*mAmGmGmCmGmG/isp18//isp18//3CholTEG/ | 169 | 74 |
| IL17RA_164 | mGmUmGmGmGmAT*G*C*A*G*G*mCmCmCmGmGmC/isp18//isp18//3CholTEG/ | 170 | 92 |
| IL17RA_165 | mUmGmUmGmGmGA*T*G*C*A*G*mGmCmCmCmGmG/isp18//isp18//3CholTEG/ | 171 | 85 |
| IL17RA_166 | mUmUmUmGmUmGG*A*T*G*C*A*mGmGmCmCmCmG/isp18//isp18//3CholTEG/ | 172 | 89 |
| IL17RA_167 | mAmCmUmCmCmUG*C*C*C*C*A*mCmCmCmAmCmU/isp18//isp18//3CholTEG/ | 173 | 75 |
| IL17RA_168 | mAmGmCmCmUmGG*T*G*C*C*A*mCmUmCmGmGmG/isp18//isp18//3CholTEG/ | 174 | 82 |
| IL17RA_169 | mGmAmGmGmAmUC*A*G*T*G*G*mUmAmCmCmUmC/isp18//isp18//3CholTEG/ | 175 | 84 |
| IL17RA_170 | mAmAmGmAmGmGA*T*C*A*G*T*mGmGmUmAmCmC/isp18//isp18//3CholTEG/ | 176 | 80 |
| IL17RA_171 | mGmCmAmUmGmGA*G*A*G*C*C*mAmUmGmCmAmG/isp18//isp18//3CholTEG/ | 177 | 80 |
| IL17RA_172 | mGmGmGmAmAmAG*A*G*G*A*T*mCmAmGmUmGmG/isp18//isp18//3CholTEG/ | 178 | 82 |
| IL17RA_173 | mAmGmGmGmAmAA*G*A*G*G*A*mUmCmAmGmUmG/isp18//isp18//3CholTEG/ | 179 | 88 |
| IL17RA_174 | mCmAmUmGmGmAG*A*G*C*C*A*mUmGmCmAmGmA/isp18//isp18//3CholTEG/ | 180 | 84 |
| IL17RA_175 | mGmGmCmAmUmGG*A*G*A*G*C*mCmAmUmGmCmA/isp18//isp18//3CholTEG/ | 181 | 88 |
| IL17RA_176 | mGmGmGmGmCmAT*G*G*A*G*A*mGmCmCmAmUmG/isp18//isp18//3CholTEG/ | 182 | 86 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_177 | mUmGmGmGmCA*T*G*A*G*mAmGm CmCmAmU/isp18//isp18//3CholTEG/ | 183 | 56 |
| IL17RA_178 | mAmUmGmGmGC*A*T*G*A*mGmAm GmCmCmA/isp18//isp18//3CholTEG/ | 184 | 84 |
| IL17RA_179 | mAmUmCmUmGmGG*A*G*A*G*mCmG mAmUmG/isp18//isp18//3CholTEG/ | 185 | 80 |
| IL17RA_180 | mGmAmUmCmUmGG*G*A*G*A*mGmC mGmAmUmG/isp18//isp18//3CholTEG/ | 186 | 80 |
| IL17RA_181 | mGmGmAmUmCmUG*G*A*G*A*mGmG mCmGmAmU/isp18//isp18//3CholTEG/ | 187 | 85 |
| IL17RA_182 | mCmCmUmCmUC*C*T*C*C*T*mCmCm UmAmCmC/isp18//isp18//3CholTEG/ | 188 | 78 |
| IL17RA_183 | mUmCmCmCmUmCT*C*C*T*C*C*mUmCm CmUmAmC/isp18//isp18//3CholTEG/ | 189 | 74 |
| IL17RA_184 | mCmUmCmCmCmUC*T*C*C*T*C*mCmUm CmUmA/isp18//isp18//3CholTEG/ | 190 | 77 |
| IL17RA_185 | mCmUmAmCmUmCC*C*T*C*T*C*mCmUm CmCmUmC/isp18//isp18//3CholTEG/ | 191 | 93 |
| IL17RA_186 | mUmCmUmAmCmUC*C*C*T*C*T*mCmCm UmCmCmU/isp18//isp18//3CholTEG/ | 192 | 96 |
| IL17RA_187 | mUmUmCmUmAmCT*C*C*C*T*C*mUmCm CmUmCmC/isp18//isp18//3CholTEG/ | 193 | 91 |
| IL17RA_188 | mUmUmUmCmUmAC*T*C*C*C*T*mCmUm CmUmCmC/isp18//isp18//3CholTEG/ | 194 | 80 |
| IL17RA_189 | mCmUmUmUmCmUA*C*T*C*C*C*mUmCm UmCmCmU/isp18//isp18//3CholTEG/ | 195 | 89 |
| IL17RA_190 | mCmCmUmUmUmCT*A*C*T*C*C*mCmUm CmUmCmC/isp18//isp18//3CholTEG/ | 196 | 86 |
| IL17RA_191 | mCmUmCmCmUmUT*C*T*A*C*T*mCmCm CmUmCmU/isp18//isp18//3CholTEG/ | 197 | 83 |
| IL17RA_192 | mUmCmCmCmUmCC*T*T*T*C*T*mAmCm UmCmCmC/isp18//isp18//3CholTEG/ | 198 | 82 |
| IL17RA_193 | mUmCmCmCmUmCG*T*C*A*C*A*mGmCm CmAmCmC/isp18//isp18//3CholTEG/ | 199 | 74 |
| IL17RA_194 | mGmCmUmCmUmCT*C*T*G*C*C*mUmCm UmCmGmU/isp18//isp18//3CholTEG/ | 200 | 79 |
| IL17RA_195 | mGmAmGmCmUmCT*C*T*C*T*G*mCmCm UmCmUmC/isp18//isp18//3CholTEG/ | 201 | 80 |
| IL17RA_196 | mGmGmGmCmUmUC*A*G*A*C*T*mCmAm CmCmUmU/isp18//isp18//3CholTEG/ | 202 | 40 |
| IL17RA_197 | mCmUmCmCmGmCA*G*G*T*A*G*mUmUm GmCmC/isp18//isp18//3CholTEG/ | 203 | 60 |
| IL17RA_198 | mGmGmCmUmCmCG*C*A*G*G*T*mAmGm UmGmU/isp18//isp18//3CholTEG/ | 204 | 20 |
| IL17RA_199 | mGmGmGmCmUmCC*G*C*A*G*G*mUmAm GmUmUmG/isp18//isp18//3CholTEG/ | 205 | 34 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphorothioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_200 | mAmCmAmCmCmCA*C*A*G*G*mGmCm AmUmGmU/isp18//isp18//3CholTEG/ | 206 | 10 |
| IL17RA_201 | mUmCmCmCmCmGA*C*C*A*G*C*mGmCm GmUmCmU/isp18//isp18//3CholTEG/ | 207 | 76 |
| IL17RA_202 | mCmUmCmCmCmCG*A*C*C*A*G*mCmGm GmGmUmC/isp18//isp18//3CholTEG/ | 208 | 47 |
| IL17RA_203 | mCmGmUmAmGmGG*C*G*T*G*T*mGmUm GmGmGmU/isp18//isp18//3CholTEG/ | 209 | 31 |
| IL17RA_204 | mUmCmGmUmAmGG*G*C*G*T*G*mUmGm UmGmGmG/isp18//isp18//3CholTEG/ | 210 | 70 |
| IL17RA_205 | mCmUmCmGmUmAG*G*G*C*G*T*mGmUm GmUmGmG/isp18//isp18//3CholTEG/ | 211 | 47 |
| IL17RA_206 | mCmCmUmCmGmUA*G*G*G*C*G*mUmGm UmGmUmG/isp18//isp18//3CholTEG/ | 212 | 58 |
| IL17RA_207 | mUmCmCmUmCmGT*A*G*G*G*C*mGmUm GmUmGmU/isp18//isp18//3CholTEG/ | 213 | 36 |
| IL17RAv208 | mCmUmCmCmUmCG*T*A*G*G*G*mCmGm UmGmUmG/isp18//isp18//3CholTEG/ | 214 | 32 |
| IL17RA_209 | mGmGmCmGmUmUC*A*A*A*C*A*mGmUm UmAmUmU/isp18//isp18//3CholTEG/ | 215 | 33 |
| IL17RA_210 | mUmCmCmAmAmUA*A*A*G*C*T*mGmUm UmAmGmG/isp18//isp18//3CholTEG/ | 216 | 84 |
| IL17RA_211 | mCmUmCmCmAmAT*A*A*A*G*C*mUmGm UmUmAmG/isp18//isp18//3CholTEG/ | 217 | 71 |
| IL17RA_212 | mAmCmUmCmCmAA*T*A*A*A*G*mCmUm GmUmUmA/isp18//isp18//3CholTEG/ | 218 | 87 |
| IL17RA_213 | mUmAmCmUmCmCA*A*T*A*A*A*mGmCm UmGmUmU/isp18//isp18//3CholTEG/ | 219 | 78 |
| IL17RA_214 | mUmGmCmCmCmUA*T*T*T*A*A*mUmUm UmUmCmA/isp18//isp18//3CholTEG/ | 220 | 84 |
| IL17RA_215 | mAmUmGmCmCmCT*A*T*T*T*A*mAmUm UmUmUmC/isp18//isp18//3CholTEG/ | 221 | 87 |
| IL17RA_216 | mUmAmUmGmCmCC*T*A*T*T*T*mAmAm UmUmUmU/isp18//isp18//3CholTEG/ | 222 | 81 |
| IL17RA_217 | mCmUmCmAmUmUT*A*T*T*T*A*mGmGm AmAmAmG/isp18//isp18//3CholTEG/ | 223 | 87 |
| IL17RA_218 | mCmCmUmCmAmUT*T*A*T*T*T*mAmGm GmAmAmG/isp18//isp18//3CholTEG/ | 224 | 85 |
| IL17RA_219 | mGmCmUmUmGmGG*C*A*G*T*mGmGm UmGmAmA/isp18//isp18//3CholTEG/ | 225 | 36 |
| IL17RA_220 | mUmCmCmAmCmUC*A*C*T*C*mCmCm AmGmCmA/isp18//isp18//3CholTEG/ | 226 | 46 |
| IL17RA_221 | mUmCmAmCmUmCC*A*C*T*C*A*mCmCm UmCmCmC/isp18//isp18//3CholTEG/ | 227 | 63 |
| IL17RA_222 | mUmCmCmCmCmAC*C*C*T*G*mAmGm CmUmCmU/isp18//isp18//3CholTEG/ | 228 | 73 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_223 | mAmGmAmGmGmAT*C*A*G*T*G*mGmUm AmCmCmU/isp18//isp18//3CholTEG/ | 229 | 76 |
| IL17RA_224 | mGmCmUmCmCmGC*A*G*G*T*A*mGmUm UmGmUmC/isp18//isp18//3CholTEG/ | 230 | 56 |
| IL17RA_225 | mCmUmCmAmCmUC*C*A*C*T*C*mAmCm CmUmCmC/isp18//isp18//3CholTEG/ | 231 | 68 |
| IL17RA_226 | mAmUmGmGmGmCT*T*G*G*G*C*mAmGm GmUmGmG/isp18//isp18//3CholTEG/ | 232 | 54 |
| IL17RA_227 | mAmUmGmGmGmUA*G*A*T*T*C*mGmUm UmCmCmA/isp18//isp18//3CholTEG/ | 233 | 57 |
| IL17RA_228 | mCmAmCmUmCmUT*G*A*A*G*C*mUmCm UmGmUmG/isp18//isp18//3CholTEG/ | 234 | 79 |
| IL17RA_229 | mCmGmUmCmAmAA*C*A*G*T*T*mAmUm UmUmAmU/isp18//isp18//3CholTEG/ | 235 | 81 |
| IL17RA_230 | mGmGmCmUmGmGA*T*T*T*C*T*mUmUm UmGmGmG/iSp18//iSp18//3CholTEG/ | 236 | 38 |
| IL17RA_231 | mCmUmCmCmUmCG*T*A*G*G*mCmGm UmGmUmG/isp18//isp18//3CholTEG/ | 237 | 32 |
| IL17RA_232 | mGmGmCmAmGmGT*G*G*T*G*A*mAmCm GmGmUmC/isp18//isp18//3CholTEG/ | 238 | 57 |
| IL17RA_233 | mGmGmGmCmAmGG*T*G*G*T*G*mAmAm CmGmGmU/isp18//isp18//3CholTEG/ | 239 | 69 |
| IL17RA_234 | mUmGmGmGmCmAG*G*T*G*G*T*mGmAm AmCmGmG/isp18//isp18//3CholTEG/ | 240 | 69 |
| IL17RA_235 | mUmUmGmGmGmCA*G*G*T*G*G*mUmGm AmAmCmG/isp18//isp18//3CholTEG/ | 241 | 62 |
| IL17RA_236 | mCmUmUmGmGmGC*A*G*G*T*G*mGmUm GmAmAmC/isp18//isp18//3CholTEG/ | 242 | 49 |
| IL17RA_237 | mCmAmCmAmGmGG*G*C*A*T*G*mUmAm GmUmCmC/isp18//isp18//3CholTEG/ | 243 | 5 |
| IL17RA_238 | mCmCmAmCmAmGG*G*G*C*A*T*mGmUm AmGmUmC/isp18//isp18//3CholTEG/ | 244 | 6 |
| IL17RA_239 | mCmCmAmCmAmAG*G*G*G*C*A*mUmGm UmAmGmU/isp18//isp18//3CholTEG/ | 245 | 5 |
| IL17RA_240 | mCmAmCmCmCmAC*A*G*G*G*G*mCmAm UmGmUmA/isp18//isp18//3CholTEG/ | 246 | 12 |
| IL17RA_241 | mUmAmCmAmCmCC*A*C*A*G*G*mGmGm CmAmUmG/isp18//isp18//3CholTEG/ | 247 | 16 |
| IL17RA_242 | mGmUmAmCmAmCC*C*A*C*A*G*mGmGm GmCmAmU/isp18//isp18//3CholTEG/ | 248 | 7 |
| IL17RA_243 | mAmGmUmAmCmAC*C*C*A*C*A*mGmGm GmGmCmA/isp18//isp18//3CholTEG/ | 249 | 4 |
| IL17RA_244 | mCmAmGmUmAmCA*C*C*C*A*C*mAmGm GmGmGmC/isp18//isp18//3CholTEG/ | 250 | 4 |
| IL17RA_245 | mCmCmAmGmUmAC*A*C*C*C*A*mCmAm GmGmGmG/isp18//isp18//3CholTEG/ | 251 | 4 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_246 | mGmUmAmGmGmGC*G*T*G*T*G*mUmGm GmGmUmC/isp18//isp18//3CholTEG/ | 252 | 26 |
| IL17RA_247 | mCmCmUmCmCmUC*G*T*A*G*T*mGmCm GmUmGmU/isp18//isp18//3CholTEG/ | 253 | 15 |
| IL17RA_248 | mUmCmCmUmCmCT*C*G*T*A*G*mGmGm CmGmUmG/isp18//isp18//3CholTEG/ | 254 | 16 |
| IL17RA_249 | mCmUmCmCmUmCC*T*C*G*T*A*mGmGm GmCmGmU/isp18//isp18//3CholTEG/ | 255 | 18 |
| IL17RA_250 | mGmCmUmCmCmUC*C*T*C*G*T*mAmGm GmGmCmG/isp18//isp18//3CholTEG/ | 256 | 49 |
| IL17RA_251 | mGmCmUT*G*G*G*C*A*G*T*G*G*T*m GmAmA/isp18//isp18//3CholTEG/ | 257 | 49 |
| IL17RA_252 | mUmCmCT*C*G*T*A*G*G*C*G*T*G*m UmGmU/isp18//isp18//3CholTEG/ | 258 | 48 |
| IL17RA_253 | mGmCmUmUG*G*C*A*G*T*G*G*mU mGmAmA/isp18//isp18//3CholTEG/ | 259 | 49 |
| IL17RA_254 | mAmCmAmCC*C*A*C*A*G*G*G*C*mA mUmGmU/isp18//isp18//3CholTEG/ | 260 | 82 |
| IL17RA_255 | mCmGmUmAG*G*G*C*G*T*G*T*G*T*mG mGmGmU/isp18//isp18//3CholTEG/ | 261 | 51 |
| IL17RA_256 | mUmCmCmUC*G*T*A*G*G*C*G*T*mG mUmGmU/isp18//isp18//3CholTEG/ | 262 | 51 |
| IL17RA_257 | mGmCmUmUmGG*G*C*A*G*T*G*mGm UmGmAmA/isp18//isp18//3CholTEG/ | 263 | 17 |
| IL17RA_258 | mAmCmAmCmCC*A*C*A*G*G*G*mCmA mUmGmU/isp18//isp18//3CholTEG/ | 264 | 82 |
| IL17RA_259 | mCmGmUmAmGG*G*C*G*T*G*T*G*mUmG mGmGmU/isp18//isp18//3CholTEG/ | 265 | 48 |
| IL17RA_260 | mUmCmCmUmCG*T*A*G*G*C*G*mUmG mUmGmU/isp18//isp18//3CholTEG/ | 266 | 48 |
| IL17RA_261 | mGmCmUmUmGmGmCmAG*G*T*G* T*mGmAmA/isp18//isp18//3CholTEG/ | 267 | 14 |
| IL17RA_262 | mAmCmAmCmCmCmAmCmAG*G*G*C* A*mUmGmU/isp18//isp18//3CholTEG/ | 268 | 11 |
| IL17RA_263 | mUmCmCmUmCmGmUmAmGG*C*G*T* G*mUmGmU/isp18//isp18//3CholTEG/ | 269 | 18 |
| IL17RA_264 | mGmCmUT*G*G*G*C*A*mGmGmUmGmGm UmGmAmA/isp18//isp18//3CholTEG/ | 270 | 16 |
| IL17RA_265 | mAmCmAC*C*C*A*C*A*mGmGmGmCm AmUmGmU/isp18//isp18//3CholTEG/ | 271 | 14 |
| IL17RA_266 | mCmGmUA*G*G*G*C*G*mUmGmUmGmU mGmGmGmU/isp18//isp18//3CholTEG/ | 272 | 31 |
| IL17RA_267 | mUmCmCT*C*G*T*A*G*mGmGmCmGmUm GmUmGmU/isp18//isp18//3CholTEG/ | 273 | 31 |
| IL17RA_268 | mGmCmUmUmGmGmGC*A*G*T*G*mGm UmGmAmA/isp18//isp18//3CholTEG/ | 274 | 9 |

TABLE 1-continued

Oligonucleotide Sequences
Special bases used in the oligonucleotides are
as follows: mN = 2' O-methyl RNA, /iSp18/ =
hexa(ethylene glycol) spacer, * = phosphoro-
thioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_269 | mAmCmAmCmCmAC*A*G*G*G*mCmAmUmGmU/isp18//isp18//3CholTEG/ | 275 | 12 |
| IL17RA_270 | mCmGmUmAmGmGmGC*G*T*G*T*mUmGmGmGmU/isp18//isp18//3CholTEG/ | 276 | 33 |
| IL17RA_271 | mUmCmCmUmCmGmUA*G*G*C*G*mUmGmGmGmU/isp18//isp18//3CholTEG/ | 277 | 33 |
| IL17RA_272 | mGmCmUmUmGG*G*C*A*G*G*mUmGmGmUmGmAmA/isp18//isp18//3CholTEG/ | 278 | 13 |
| IL17RA_273 | mAmCmAmCmCC*A*C*A*G*G*mGmGmCmAmUmGmU/isp18//isp18//3CholTEG/ | 279 | 34 |
| IL17RA_274 | mCmGmUmAmGG*G*C*G*T*G*mUmGmGmGmU/isp18//isp18//3CholTEG/ | 280 | 46 |
| IL17RA_275 | mUmCmCmUmCG*T*A*G*G*mCmGmUmGmGmGmU/isp18//isp18//3CholTEG/ | 281 | 47 |
| IL17RA_276 | mAmCmAC*C*C*A*C*A*G*G*G*C*A*mUmGmU/isp18//isp18//3CholTEG/ | 282 | 82 |
| IL17RA_277 | mCmGmUA*G*G*C*G*T*G*T*G*mGmGmU/isp18//isp18//3CholTEG/ | 283 | 48 |
| IL17RA_278 | mAmCmCmAmCA*G*G*G*C*mAmUmGmUmAmG/isp18//isp18//3CholTEG/ | 284 | 7 |
| IL17RA_279 | mCmGmUmAmGmGmCmGT*G*T*G*T*G*mGmGmU/isp18//isp18//3CholTEG/ | 285 | 18 |
| IL17RA_280 | mCmCmCmAmCmAmGmGmGG*C*A*T*G*T*mAmGmU/isp18//isp18//3CholTEG/ | 286 | 7 |
| IL17RA_281 | mCmCmCmAmCA*G*G*G*C*mAmUmGmUmAmGmU/isp18//isp18//3CholTEG/ | 287 | 10 |
| IL17RA_282 | mCmCmCmAmCmAmGG*G*C*A*T*mGmUmAmGmU/isp18//isp18//3CholTEG/ | 288 | 3 |
| IL17RA_283 | mGmUmAmGmGmCG*T*G*T*G*T*mGmGmGmUmC/isp18//isp18//3CholTEG/ | 289 | 33 |
| IL17RA_284 | mGmUmAG*G*C*G*T*mGmUmGmUmGmGmGmUmC/isp18//isp18//3CholTEG/ | 290 | 31 |
| IL17RA_285 | mGmUmAmGmGmCmGmUG*T*G*T*G*G*mGmUmC/isp18//isp18//3CholTEG/ | 291 | 18 |
| IL17RA_286 | mGmUmAmGGG*C*G*T*G*T*mGmUmGmGmGmUmC/isp18//isp18//3CholTEG/ | 292 | 46 |
| IL17RA_287 | mCmCmCA*C*A*G*G*G*mGmCmAmUmGmUmUmAmGmU/isp18//isp18//3CholTEG/ | 293 | 12 |
| IL17RA_288 | mGmUmAG*G*C*G*T*G*T*G*T*G*G*mGmUmC/isp18//isp18//3CholTEG/ | 294 | 48 |
| IL17RA_289 | mGmUmAmGG*G*C*G*T*G*T*G*T*mGmGmUmC/isp18//isp18//3CholTEG/ | 295 | 51 |
| IL17RA_290 | mCmCmCA*C*A*G*G*G*C*A*T*G*T*mAmGmU/isp18//isp18//3CholTEG/ | 296 | 57 |
| IL17RA_291 | mCmCmCmAC*A*G*G*G*C*A*T*G*mUmAmGmU/isp18//isp18//3CholTEG/ | 297 | 35 |

TABLE 1-continued

Oligonucleotide Sequences
Special bases used in the oligonucleotides are as follows: mN = 2' O-methyl RNA, /iSp18/ = hexa(ethylene glycol) spacer, * = phosphorothioate, /3CholTEG/ = 3' cholesterol

| Compound ID | Oligonucleotide Sequence (5' to 3') | SEQ ID NO: | % IL17RA mRNA Expression |
|---|---|---|---|
| IL17RA_292 | mCmCmCmAmCA*G*G*G*G*C*A*T*mGmU mAmGmU/isp18//isp18//3CholTEG/ | 298 | 10 |
| IL17RA_293 | mGmUmAmGmGG*C*G*T*G*T*G*T*mGmG mGmUmC/isp18//isp18//3CholTEG/ | 299 | 55 |
| Control | mGmUmUmUmCmAC*C*A*C*C*C*mAmAm UmUmCmC/isp18//iSp18//3CholTEG/ | 300 | |

TABLE 2

Oligonucleotide Sequences

Special bases used in the oligonucleotides are as follows: mN = 2' O-methyl RNA, /iSp18/ = hexa(ethylene glycol) spacer phosphoramidite, * = phosphorothioate, /3CholTEG/ = 3' cholesterol

| Compound ID | Oligonucleotide Sequence (5' to 3') | SEQ ID NO: |
|---|---|---|
| Control | mGmUmUmUmCmAC*C*A*C*C*C*mAmAmUmUmCmC/ iSp18//iSp18//3CholTEG/ | 300 |
| Anti-TNF | mUmGmGmAmGT*A*G*A*C*A*mAmGmGmUmAmC/ iSp18//iSp18//3CholTEG/ | 301 |
| IL17RA_219 | mGmCmUmUmGmGG*C*A*G*G*T*mGmGmUmGmAmA/ iSp18//iSp18//3CholTEG/ | 225 |

Example 2. IL-17RA mRNA Knockdown in Human Skin Using SNAs Formulated in a Gel Vehicle Methods and Materials Tissue Culture. Healthy human ex vivo skin, freshly acquired from a single donor was received the day of experiment initiation and prepared immediately. Prior to use, the skin was inspected, noting any areas of extensive stretch marks or scarring, and any sections with visible holes or damage were removed. A dermatome was used to excise full thickness skin from the donor sample. The resulting tissue contained an intact stratum corneum, epidermis, and dermis. No subcutaneous tissue from the surgical explant remained. The skin was carefully cut to the appropriate size and care was taken not to stretch the skin when it was placed into the Franz cells. The skin was then clamped into the Franz cell. Next, a stir bar and receiving medium that had been pre-warmed to 37° C. were added to each Franz cell. The receiving medium consisted of Dulbecco's modified Eagle's medium, supplemented with 2% fetal bovine serum, 50 U/mL penicillin, 50 mg/mL streptomycin, 0.25 µg/mL amphotericin B and 10 µg/mL gentamycin. The Franz cells, explants and receiving medium were allowed to equilibrate for a minimum of 30 minutes, after which the temperature of the media in each cell was verified to be 37±1° C. Any air bubbles that were introduced during assembly of the cells were removed. The integrity of the skin was confirmed prior to initiating the study by inverting the cell. If leaks were identified, the skin and donor chamber were repositioned until leaks were absent. Over the course of the experiment, the skin was maintained at ambient humidity and at an epidermal surface temperature of 32° C., which was regulated using 37° C. water-jacketing of the receptor chamber containing cell culture media that contacts the dermal portion of the explant.

SNA Synthesis. The oligonucleotide was synthesized at the 1 mmole scale employing standard UniLinker support (ChemGenes). The DNA, 2'-O-Me RNA monomers and hexa(ethylene glycol) spacers were obtained from ChemGenes Corporation. The cholesterol modifier was obtained from Glen Research. Linkages were either standard phosphodiesters or phosphorothioates prepared with a solution of 0.2 M phenylacetyl disulfide (PADS) in a mixture of 1:1 lutidine:ACN. Synthesis was performed DMT-off, in the 3' to 5' direction. After synthesis, the oligonucleotide was cleaved from the support and de-protected using a 4:1 mixture of ammonium hydroxide and ethanol at 55° C. for 16 hours. The oligonucleotide was purified via high performance liquid chromatography (HPLC) techniques. Molecular weights and extinction coefficients were calculated using the IDT OligoAnalyzer. The verification of the oligonucleotide product molecular weight was performed using electrospray ionization mass spectrometry (ESI-MS). Finally, the oligonucleotide concentration was determined by UV-absorbance at 260 nm on a microplate reader (BioTek).

Liposomes were formulated by first dissolving 250 mg 1,2-dioleoyl-sn-glycero-3-phosphocholine (DOPC) in chloroform to a final concentration of 50 mg/mL. The solvent was then removed under nitrogen to form a thin lipid film. The film was lyophilized overnight to ensure all solvent was removed. The lipid film was subsequently hydrated with 10 mM phosphate buffered saline (PBS) and sonication/freeze-fracture were used to form large, unilamellar vesicles. These vesicles were then continuously homogenized through a micro-fluidizer at up to 25 kpsi, until the desired mean number diameter of 20 nm was achieved. Liposome concentrations were determined using a choline quantification assay and the particle size and dispersion were measured by dynamic light scattering (DLS).

SNAs targeting human IL-17RA, compound IL17RA_282, were formulated by mixing a 30-fold molar excess of cholesterol-modified oligonucleotide, SEQ ID NO: 288, to the liposome suspension in PBS followed by overnight incubation at 4° C.

Drug Application to Skin. A gel vehicle was used to apply IL17RA_282 to the skin. The pre-formulated SNAs were mixed into the gel vehicle, resulting in three drug product strengths of 0, 0.00007 and 0.007% w/w (oligonucleotide weight). The composition of these drug products can be found in Table 3.

These drug products were then applied topically to the skin explants. The drug products were briefly mixed prior to dosing using a pipette tip. 40 µL of each drug product was dosed topically to each Franz cell using a positive displacement pipette. The pipette tip was used to spread the drug product evenly covering the entire exposed surface area of the skin (1.0 cm2). After dosing, the sampling port was occluded to prevent solvent evaporation during the study. The actual dosing time was recorded and the explants were maintained at ambient humidity and at an epidermal surface temperature of 32° C. for 24 hours.

RNA Extraction and qRT-PCR. At the conclusion of the 24 hour incubation period, the Franz cells were disassembled and the skin was carefully removed from each cell. A cotton swab wetted with PBS was used to remove the drug product and then the application area was blotted dry. Three samples were cut from the 1.0 cm² dosing area using a 4 mm biopsy punch. The skin was not stretched while the biopsy punches were taken. The biopsy punches were then lysed in RLT buffer (Qiagen) with a bead homogenizer. RNA was isolated from lysates using the RNEasy 96-well kit (Qiagen) according to the manufacturer's instructions. cDNA was then synthesized from RNA isolates using the cDNA high capacity reverse transcription kit (Life Technologies). cDNA was prepared on a thermocycler with the following temperature program: 25° C. for 10 minutes, 37° C. for 90 minutes, 85° C. for 5 minutes followed by a 4° C. hold. The resulting cDNA was diluted 8 fold with nuclease-free water. qPCR was performed using 6 µL of the diluted cDNA, 4.66 µL LightCycler480 Probes Master Mix (Roche), 0.47 µL human IL-17RA specific FAM-labeled probe and primers, and 0.37 µL human Glyceraldehyde-3-phosphate dehydrogenase (GAPDH) specific HEX-labeled probe and primers per reaction well of a 384-well optical reaction plate (Roche). The primer and probe set for IL-17RA was purchased commercially (Hs01064648 m1, Thermo Fisher Scientific). The primer and probe set for GAPDH was designed using the known human genome sequence (NCBI reference sequences NM_002046.5) and was found to be specific by "blastn" analysis (NCBI). The oligonucleotide sequences used for GAPDH were: forward 5'-CAA GGT CAT CCA TGA CAA CTT TG-3' (SEQ ID NO: 4), reverse 5'-GGG CCA TCC ACA GTC TTC T-3' (SEQ ID NO: 5), probe 5'-HEX-ACC ACA GTC CAT GCC ATC ACT GCC A-BHQ1-3' (SEQ ID NO: 6). qPCR reactions, in technical duplicate, were carried out on the Roche Lightcycler 480 under the following conditions: initial denaturation at 95° C. for 10 minutes and then 50 cycles of denaturation at 95° C. for 10 seconds, annealing at 60° C. for 30 seconds and extension at 72° C. for 1 second. Cp values were obtained by analysis with the 2nd derivative method. Relative gene expression was determined by normalization with the housekeeping gene (GAPDH) and the ΔΔ-Ct method. Statistical analysis was done by performing a one-way ANOVA.

Protein Isolation and Western Blot. Total protein was isolated from the biopsy lysates with acetone precipitation. Lysates from each treatment group were pooled before isolating the protein to increase protein yield. Briefly, four volumes of ice cold acetone were added to the lysate and incubated at −20° C. for 30 minutes. The samples were centrifuged and decanted, and the pellets were washed with one volume ice cold ethanol. Again, the samples were centrifuged and the pellets were allowed to air dry. The pellets were re-suspended in one volume Laemmli sample buffer containing 1% β-mercaptoethanol. To ensure the samples were completely dissolved, they were boiled at 95° C. for 10 minutes and subsequently centrifuged to remove any undissolved debris.

The protein isolates were loaded into a 10% SDS-PAGE gel, run and transferred overnight (22 V) to an Immobilon PSQ PVDF membrane (ISEQ00010, Millipore). The membrane was blocked for 1 hour with 5% dry milk in tris buffered saline containing Tween 20 (the resulting buffer is referred to as TBST) followed by a 5 minute wash in TBST. Human-specific antibodies targeting IL-17RA or β-actin protein were used to probe for the presence of those specific proteins. IL-17RA protein was detected using an anti-IL-17RA rabbit monoclonal primary antibody, and was shown to detect a protein with a predicted molecular weight of 150 kDa (12661, Cell Signaling). This antibody was diluted in blocking buffer (5% dry milk in TBST) at a ratio of 1:500 prior to use. β-actin protein was detected using an anti-β-actin rabbit monoclonal primary antibody, and was shown to detect a protein with a predicted molecular weight of 45 kDa (4970, Cell Signaling). This antibody was diluted in blocking buffer at a ratio of 1:1000 prior to use. Primary antibody incubation occurred overnight at 4° C.

After the incubation period, the membrane was rinsed twice with TBST, followed by two consecutive washes with TBST of 15 minutes and 5 minutes. Next, the membrane was incubated with an anti-rabbit HRP secondary antibody (7074, Cell Signaling) diluted in blocking buffer at a ratio of 1:1000 prior to use. The secondary antibody incubation occurred for 90 minutes at room temperature. Then, the membrane was rinsed twice with TBST, followed by two consecutive washes with TBST for 15 minutes and 5 minutes. Then, the membrane was further washed twice with distilled water for 5 minutes. Subsequently, GE Amersham Prime ECL reagent (RPN2232) was added to the membrane and incubated at room temperature for 5 minutes. Then, the membrane was imaged using an exposure interval of 20 seconds for up to 2 minutes on a BioRad GelDoc Imager. Finally, images were analyzed by densitometry and IL-17RA signal was normalized to β-actin signal to compared expression levels across treatments.

TABLE 3

Drug Product Compositions

| Ingredient | Gel Strength Formulations (w/w) | | |
|---|---|---|---|
| | 0% | 0.00007% | 0.007% |
| SEQ ID NO: 288 | 0 | 0.00007 | 0.007 |
| DOPC | 0 | 0.0003801 | 0.03801 |
| Diethylene glycol monoethyl ether (Transcutol P) | 25 | 25 | 25 |
| Glycerin | 5 | 5 | 5 |
| Hydroxyethyl Cellulose | 1 | 1 | 1 |
| Methylparaben | 0.15 | 0.15 | 0.15 |
| Propylparaben | 0.05 | 0.05 | 0.05 |
| Disodium EDTA | 0.1 | 0.1 | 0.1 |
| Sodium Metabisulfite | 0.2 | 0.2 | 0.2 |
| Water | 68.5 | 68.5 | 68.45 |

Results

Figure 9:
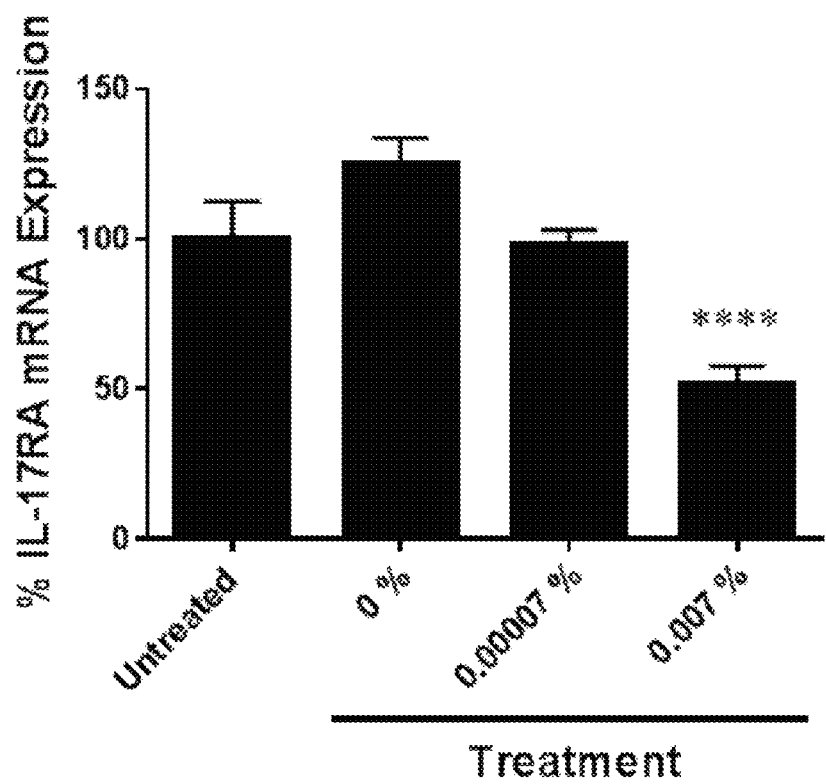
FIG. 9 depicts inhibition of IL-17RA mRNA expression. The graph shows IL-17RA mRNA expression in healthy human skin explants after 24 hours treatment, as measured by qRT-PCR (percent of untreated ±SEM). Each drug product treatment group, n=9 samples. Untreated group, n=8 samples. One-way ANOVA, 31 DF, p=0.0011 (0.007% versus untreated) and **** p<0.0001 versus 0% gel.
Figure 10:
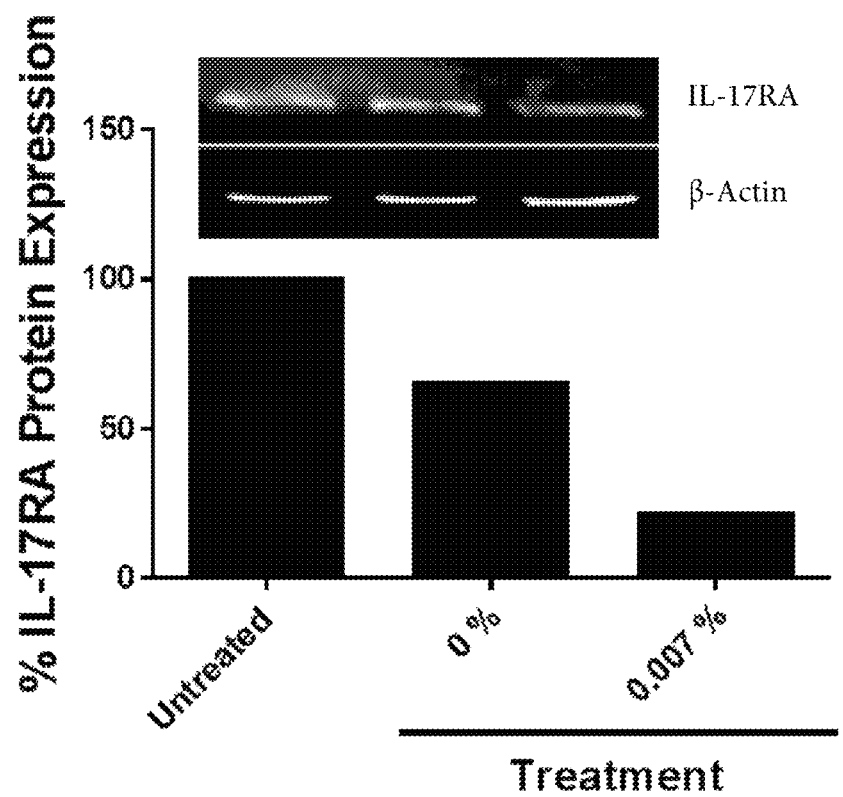
FIG. 10 depicts inhibition of IL-17RA protein expression. The graph shows IL-17RA protein expression in healthy human skin explants after 24 hours treatment with IL17RA_282 in formulation described in Table 3, as measured by western blot (percent of untreated). Pooled samples for each group.

The IL-17RA mRNA targeted SNA (compound IL17RA_282) formulated as a drug product in a gel vehicle showed dose-dependent knockdown of IL-17RA mRNA in healthy human skin explant after only 24 hours of treatment (FIG. 9). Knockdown was observed when compared to both untreated skin and the 0% strength drug product. Treatment with the 0.007% strength drug product resulted in statistically significant IL-17RA mRNA inhibition compared to untreated ($p=0.0011$) and 0% strength drug product ($p<0.0001$) by one-way ANOVA. The IL-17RA mRNA targeted SNA (compound IL17RA_282) formulated as a drug product in a gel vehicle showed inhibition of IL-17RA protein expression in healthy human skin explant after only 24 hours of treatment (FIG. 10). Knockdown was observed when compared to both untreated skin and the 0% strength drug product. The graph represents the analyzed densitometry data collected from the western blot (inset). There was insufficient material to perform a protein-level analysis for the skin samples treated with 0.0007% gel.

Discussion and Conclusions

Clinical data suggests that the IL-17 signaling pathway plays a significant role in sustaining the psoriasis disease state. While current monoclonal antibody therapies, like brodalumab, provide very effective treatment options, they also present with troubling side-effect profiles. This presents a therapeutic need for a safer alternative. Antisense technology can reduce the expression of mRNA in cells; however, antisense oligonucleotides generally have poor uptake into cells and skin. In contrast, it has been found that when oligonucleotides are arranged in the SNA geometry, they exhibit skin penetration properties and increased cellular uptake. Given these advantages and the therapeutic needs for psoriasis treatment, an antisense SNA based therapy targeting human IL-17RA in the skin may prove an effective treatment for psoriasis.

It has been shown here that when the IL-17RA mRNA targeted SNA (compound IL17RA_282) formulated as a drug product in a gel vehicle is applied topically to healthy human skin explants, there is a pharmacodynamic effect seen at both the level of IL-17RA mRNA and protein. Increasing strength of the drug product results in decreased IL-17RA expression.

The response observed in this study represents only a 24 hour treatment. It is expected that longer treatment with multiple doses would further enhance the inhibition observed. Given the importance of IL-17 signaling in maintaining the diseased state observed in psoriasis, a strong topical drug product candidate for the treatment of psoriasis is presented.

Example 3. IL-17RA mRNA Knockdown in Human Psoriatic Skin Using SNAs Formulated in a Gel Vehicle Methods and Materials Tissue Culture. Four skin biopsies (3 mm diameter) were obtained from each of 8 different patients with mild to moderate plaque psoriasis. Biopsies were taken directly from psoriatic plaques. Due to the limited number of biopsies that can be taken from a single patient, only 4 biopsies were taken per individual. Biopsies were taken from volunteers at about 45 minute intervals and transported to the laboratory (rolled in moist sterile gauze). The time between taking biopsies and starting the incubation was between 5 and 7.5 hours. The biopsies were positioned in the membrane of an insert-well, and incubated in 12-well plates at 32° C. with ambient $CO_2$ and humidity. The membranes were immersed in 1 mL cell culture medium (Dulbecco's modified Eagle's medium, 1% fetal bovine serum, 1.25 μg/mL amphotericin B, 50 μg/mL gentamicin, and 0.1 U/mL penicillin/streptomycin) such that the dermis contacted the medium in the well and the epidermis was exposed to air. There was 1 biopsy per well. The lid of the 12-well plate was elevated using two sterile 1 mL pipette tips to limit moisture build-up. The total incubation time of the drug product treated skin was 21 hours and 15 minutes.

SNA Synthesis. The oligonucleotide, SEQ ID NO: 288, was synthesized via standard solid-phase phosphoramidite chemistry. The molecule was synthesized with successive cycles of de-protection, monomer addition, capping, and oxidation. The DNA, and 2'-O-Me RNA monomers were obtained from Sigma Aldrich Biochemie (Germany). The hexa(ethylene glycol) spacers and cholesterol modifier were obtained from ChemGenes Corporation. Linkages were either standard phosphodiesters or phosphorothioates prepared with a solution of 0.2 M phenylacetyl disulfide (PADS) in a mixture of 1:1 lutidine:ACN. Synthesis was performed DMT-off, in the 3' to 5' direction. After synthesis, the oligonucleotide was cleaved from the support and de-protected using a 3:1 mixture of ammonium hydroxide and ethanol at 65° C. for 17 hours. The oligonucleotide was purified via anion exchange high performance liquid chromatography (AX-HPLC) techniques. Then the oligonucleotide solution was lyophilized completely to a dry powder. Verification of the oligonucleotide product molecular weight was performed using electrospray ionization mass spectrometry (ESI-MS) and dual-MS sequencing was performed to confirm the oligonucleotide sequence. Oligonucleotide concentration was determined by UV-absorbance at 260 nm.

Liposomes were formulated by Avanti Polar Lipids (Alabama, USA). First, 500 g 1,2-dioleoyl-sn-glycero-3-phosphocholine (DOPC) was dissolved in chloroform to a final concentration of 50 mg/mL. The solvent was then removed under nitrogen to form a thin lipid film. The film was lyophilized overnight to ensure all solvent was removed. The lipid film was subsequently hydrated with Hyclone sterile, nuclease-free water (SH30538.03, GE) at a concentration of 100 mg/mL and sonication/freeze-fracture were used to form large, unilamellar vesicles. These vesicles were then continuously homogenized through a micro-fluidizer at up to 25 kpsi, until the mean number diameter of 20 nm was achieved. The liposome solution was further concentrated by tangential flow filtration (TFF) to a final lipid concentration of 208 mg/mL. Lipid concentrations were determined using a choline quantification assay and nuclear magnetic resonance spectroscopy. The particle size and dispersion were measured by dynamic light scattering (DLS).

SNAs targeting human IL-17RA, were formulated by mixing a 30-fold molar excess of cholesterol-modified full length oligonucleotide to the liposome suspension in Hyclone sterile, nuclease-free water (SH30538.03, GE) followed by overnight incubation at 4° C.

Drug Application to the Skin. The pre-formulated SNAs targeting human IL-17RA were mixed into a gel vehicle, resulting in four IL17RA_282 gel strengths of 0, 0.01, 0.1 and 1.0% w/w (full length oligonucleotide weight). The composition of these drug products can be found in Table 4.

The IL17RA_282 gels were then applied topically to the skin explants in replicates of eight. During the sample processing, one sample in the 1.0% group was lost, resulting in only 7 replicates for that group. Each replicate was taken from a different patient for accurate representation and comparison of a patient specific response. The IL17RA_282 gels were briefly mixed prior to dosing using a pipette tip.

10 μL of each drug product was dosed topically to each 3 mm biopsy using a positive displacement pipette. The pipette tip was used to spread the drug product evenly covering the entire exposed surface area of the skin. The actual dosing time was recorded and the explants were maintained at 32° C. and ambient humidity for 21 hours.

At the conclusion of the 21 hour incubation period, the biopsies were removed from each membrane. A cotton swab wetted with PBS was used to remove the drug product and then the application area was blotted dry. The biopsy punches were lysed in RLT buffer (Qiagen) with a bead homogenizer and stored frozen at −80° C. until shipped on dry ice to the research facility.

RNA Extraction and qRT-PCT. RNA was isolated from lysates using the RNEasy 96-well kit (Qiagen) according to the manufacturer's instructions. cDNA was then synthesized from RNA isolates using the cDNA high capacity reverse transcription kit (Life Technologies). cDNA was prepared on a thermocycler with the following temperature program: 25° C. for 10 minutes, 37° C. for 90 minutes, 85° C. for 5 minutes followed by a 4° C. hold. The resulting cDNA was diluted 8 fold with nuclease-free water. qPCR was performed using 6 μL of the diluted cDNA, 4.66 μL LightCycler480 Probes Master Mix (Roche), 0.47 μL human IL-17RA specific FAM-labeled probe and primers, and 0.37 μL human Glyceraldehyde-3-phosphate dehydrogenase (GAPDH) specific HEX-labeled probe and primers per reaction well of a 384-well optical reaction plate (Roche). The primer and probe set for IL-17RA was purchased commercially (Hs01064648_m1, Thermo Fisher Scientific). The primer and probe set for GAPDH was designed using the known human genome sequence (NCBI reference sequences NM_002046.5) and was found to be specific by "blastn" analysis (NCBI). The oligonucleotide sequences used for GAPDH were: forward 5'-CAA GGT CAT CCA TGA CAA CTT TG-3' (SEQ ID NO: 4), reverse 5'-GGG CCA TCC ACA GTC TTC T-3' (SEQ ID NO: 5), probe 5'-HEX-ACC ACA GTC CAT GCC ATC ACT GCC A-BHQ1-3' (SEQ ID NO: 6). qPCR reactions, in technical duplicate, were carried out on the Roche Lightcycler 480 under the following conditions: initial denaturation at 95° C. for 10 minutes and then 50 cycles of denaturation at 95° C. for 10 seconds, annealing at 60° C. for 30 seconds and extension at 72° C. for 1 second. Cp values were obtained by analysis with the 2nd derivative method. Relative gene expression was determined by normalization with the housekeeping gene (GAPDH) and the ΔΔ-Ct method. Statistical analysis was done by performing a one sample t-test.

TABLE 4

Drug Product Compositions

| Ingredient | Gel Strength Formulations (w/w) | | | |
|---|---|---|---|---|
| | 0% | 0.01% | 0.1% | 1.0% |
| SEQ ID NO: 288 | 0 | 0.01419 | 0.1419 | 1.419 |
| DOPC | 0 | 0.2655 | 2.655 | 26.55 |
| Diethylene glycol monoethyl ether (Transcutol P) | 25 | 25 | 25 | 25 |
| Glycerin | 5 | 5 | 5 | 5 |
| Hydroxyethyl Cellulose | 1 | 1 | 1 | 1 |
| Methylparaben | 0.15 | 0.15 | 0.15 | 0.15 |
| Propylparaben | 0.05 | 0.05 | 0.05 | 0.05 |
| Disodium EDTA | 0.1 | 0.1 | 0.1 | 0.1 |
| Sodium Metabisulfite | 0.2 | 0.2 | 0.2 | 0.2 |
| Water | 68.5 | 68.2 | 65.7 | 40.5 |

Results

Figure 11:
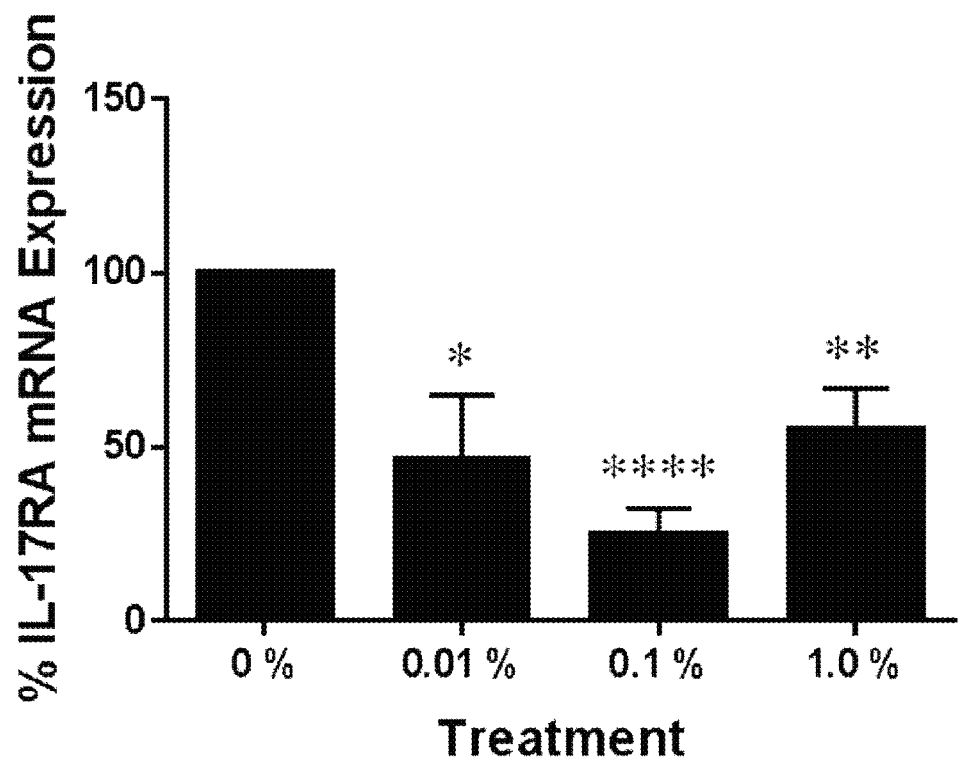
FIG. 11 shows inhibition of IL-17RA mRNA expression. * p<0.05;  p<0.01; ** p<0.0001 compared to vehicle. A one sample t-test was used.
Figure 12A:
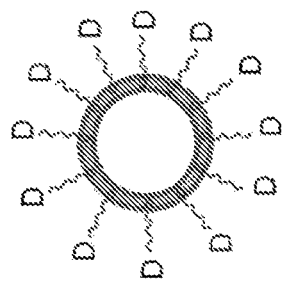
FIGS. 12A-12D show configurations of multiplexed SNAs. Liposome were surface functionalized in the following configurations: monoplex SNA (FIG. 12A); multiplex SNA containing two targeted antisense oligonucleotides (FIG. 12B); multiplex SNA containing three targeted antisense oligonucleotides (FIG. 12C); non-targeted control SNA (FIG. 12D).
Figure 12B:
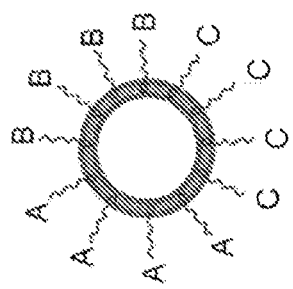
Figure 12C:
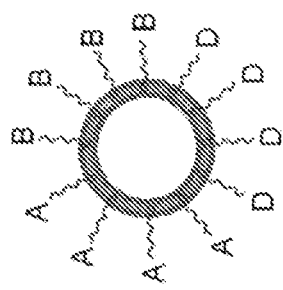
Figure 12D:
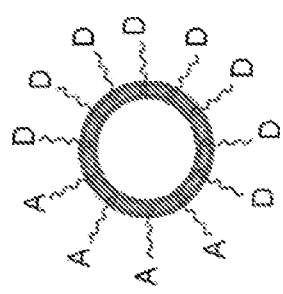

The IL17RA_282 gels showed dose-dependent knockdown of IL-17RA mRNA in human psoriatic skin biopsies after 21 hours of treatment (FIG. 11). Knockdown was observed when comparing the IL17RA_282-containing gels to the 0% gel strength formulation. Treatment with the IL17RA_282 gels resulted in statistically significant reduction of IL-17RA mRNA.

Discussion and Conclusions

It was shown here that when the IL17RA_282 gel is applied topically to ex vivo human psoriatic skin biopsies, there is a pharmacodynamic effect seen at the level of IL-17RA mRNA. The response observed in this study represents only a 21 hour treatment. It is expected that longer treatment with multiple doses would further enhance the inhibition observed. Given the importance of IL-17 signaling in maintaining the diseased state observed in psoriasis, a strong topical drug product candidate for the treatment of psoriasis is presented.

Example 4. Multiplex SNAs Targeting Three Different mRNAs

Materials and Methods

Multiplex SNA Synthesis. SNAs were formulated by mixing a 100× molar excess (unless otherwise stated) of cholesterol-modified oligonucleotide to a liposome suspension in PBS and storing them overnight, protected from light, at 4° C. Four different oligonucleotides were used for the synthesis process: an antisense oligonucleotide targeting human IL-4R, an antisense oligonucleotide targeting human IL-1β, an antisense oligonucleotide targeting human CTGF, and a same length control oligonucleotide that does not have any complementarity to known genes (confirmed by BLAST). For monoplex SNAs, the oligonucleotide population consisted of 33% targeted antisense oligonucleotide and 66% control oligonucleotide. For multiplex SNAs containing two different targeted antisense oligonucleotides, the oligonucleotide population consisted of 33% of each targeted antisense oligonucleotide and the remaining 33% control oligonucleotide (FIG. 12). For multiplex SNAs containing three different targeted antisense oligonucleotides, the oligonucleotide population consisted of 33% of each targeted antisense oligonucleotide. Control SNAs consisted of 100% of the control oligonucleotide (FIG. 9).

Cell Culture Studies. Primary human foreskin keratinocytes (HFKs) were seeded at passage 5 in 96-well, tissue culture plates at a cell density of 17,000 cells per well. Cells were allowed to rest in the incubator overnight following plating. Cells were treated in triplicate with either an IL-4R targeted antisense SNA, IL-1β targeted antisense SNA, CTGF targeted antisense SNA, a multiplex SNA targeting more than one transcript or a non-complementary control SNA (confirmed by NCBI Blast), comprising the same 'gap-mer' design and 3'-chemical modifications, at concentrations of 1000, 100, 10 and 1 nM in fresh maintenance media. Unless otherwise stated, all treatments lasted 24 hours.

RNA Extraction and Quantitative Reverse Transcriptase Polymerase Chain Reaction (qRT-PCR). HFK cells were lysed in RLT Buffer (Qiagen) at 24 hours post-transfection. RNA was isolated from lysates using the RNEasy 96-well kit (Qiagen) according to the manufacturer's instructions. cDNA was then synthesized from RNA isolates using the cDNA High Capacity Reverse Transcription Kit (Life Technologies). Samples were run on a thermocycler at 25° C. for 10 minutes, 37° C. for 90 minutes, 85° C. for 5 minutes and held at 4° C. to generate cDNA. qPCR was performed using 6 μL of the synthesized cDNA, 4.66 μL LightCycler480 Probes Master Mix (Roche), 0.47 μL target specific FAM-labeled probe and primers, and 0.37 μL human Glyceraldehyde-3-phosphate dehydrogenase (GAPDH) specific HEX-labeled probe and primers per reaction well of a 384-well optical reaction plate (Roche). The primer and probe sets for IL-4R, IL-1β and CTGF were purchased from ThermoFisher Scientific (catalogue numbers Hs00166237_m1, Hs01555410_m1 and Hs01026927_g1, respectively). The primer and probe set for GAPDH was designed using the known human genome sequence (NCBI reference sequence NM_002046.5) and was found to be specific by "blastn" analysis (NCBI). The oligonucleotide sequences used for GAPDH were: forward 5'-CAA GGT CAT CCA TGA CAA CTT TG-3' (SEQ ID NO: 4), reverse 5'-GGG CCA TCC ACA GTC TTC T-3' (SEQ ID NO: 5), probe 5'-HEX-ACC ACA GTC CAT GCC ATC ACT GCC A-BHQ1-3' (SEQ ID NO: 6). qPCR reactions, in technical duplicate, were carried out on the Roche Lightcycler 480 under the following conditions: initial denaturation at 95° C. for 10 minutes and then 50 cycles of denaturation at 95° C. for 10 seconds, annealing at 60° C. for 30 seconds and extension at 72° C. for 1 second. Cp values were obtained by analysis with the 2nd derivative method. Relative gene expression was determined by normalization with the housekeeping gene (GAPDH) and the ΔΔ-Ct method. Each treatment was compared to its respective concentration control.

Results

Seven different SNA configurations were made to test whether three different mRNAs can be targeted using single SNA construct. Three mRNAs were chosen that were not functionally dependent on each other for expression and were not in a single known pathway. In certain cases, it may be advantageous to target mRNAs that are part of the same pathway, e.g. TNF, IL17, IL22, to control a specific pathway. SNAs were synthesized targeting each individual mRNA alone, three pairs of mRNAs and one SNA configuration that can target all three mRNAs. Control oligonucleotide was used to ensure that each SNA configuration has the same number of targeted and non-targeted oligonucleotides.

Figure 13:
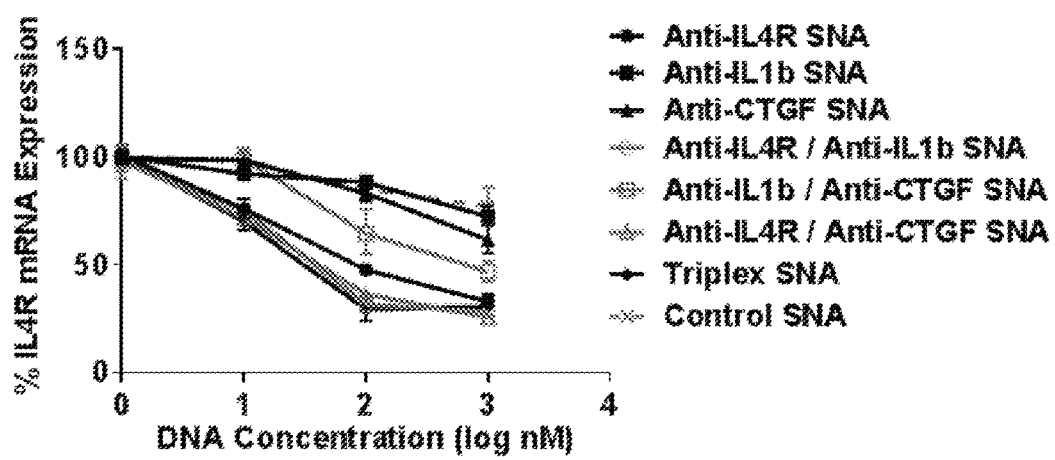
FIG. 13 shows inhibition of IL4R mRNA in cells treated with various multiplex SNA configurations. Liposome were surface functionalized various targeted antisense oligonucleotide(s) or control oligonucleotide. The expression of IL4R mRNA is reduced noticeably when cells are treated with SNAs that target IL4R. Control SNA and SNAs functionalized with non-targeting oligonucleotides do not reduce IL4R mRNA expression to the same extent.
Figure 14:
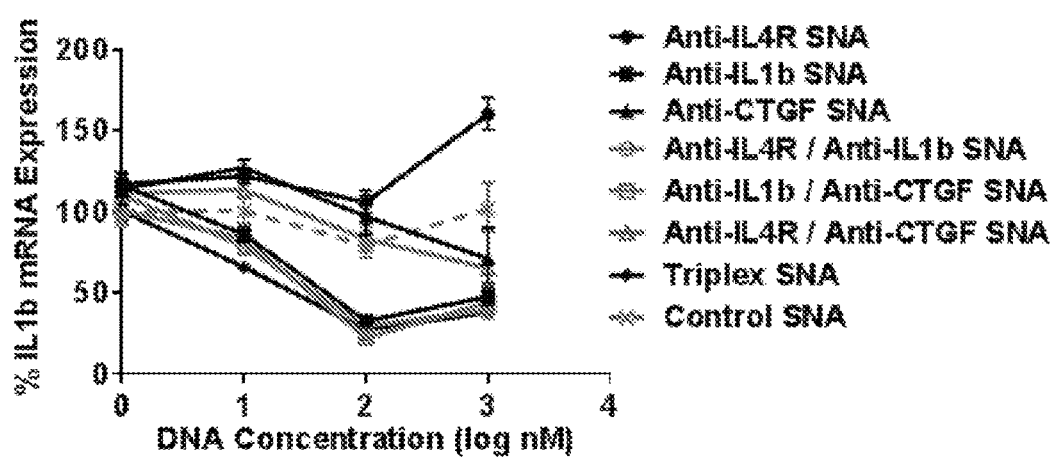
FIG. 14 shows inhibition of IL1b mRNA in cells treated with various multiplex SNA configurations. Liposome were surface functionalized various targeted antisense oligonucleotide(s) or control oligonucleotide. The expression of IL1b mRNA is reduced noticeably when cells are treated with SNAs that target IL1b. Control SNA and SNAs functionalized with non-targeting oligonucleotides do not reduce IL1b mRNA expression to the same extent.
Figure 15:
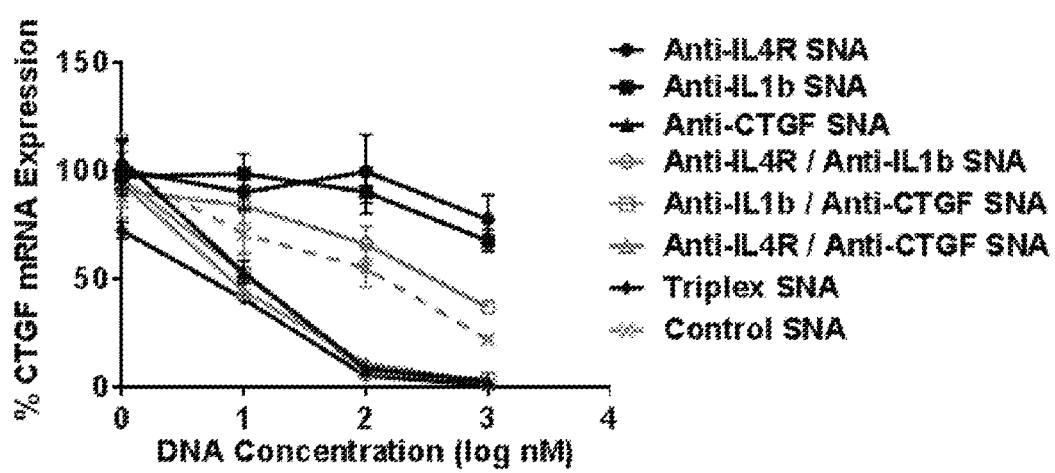
FIG. 15 shows inhibition of CTGF mRNA in cells treated with various multiplex SNA configurations. Liposome were surface functionalized with various targeted antisense oligonucleotide(s) or control oligonucleotide. The expression of CTGF mRNA is reduced noticeably when cells are treated with SNAs that target CTGF. Control SNA and SNAs functionalized with non-targeting oligonucleotides do not reduce CTGF mRNA expression to the same extent.

The results from cell culture experiments demonstrate that single SNA can be formulated that targets three different mRNAs. The mRNAs chosen were interleukin 4 receptor (IL4R), interleukin 1 beta (IL1b) and connective tissue growth factor (CTGF). These targets were chosen because in other experiments it was noted that knocking down any one of these mRNAs didn't significantly reduce the levels of the other two. The results show that when antisense oligonucleotides targeting any single mRNA is present on the SNA, the expression of that mRNA is reduced in a dose dependent manner (FIG. 13 for IL4R, FIG. 14 for IL1b, FIG. 15 for CTGF). This configuration can be extended to target more than three mRNAs. The total antisense loading per SNA may be the theoretical limit to the number of mRNAs that can be targeted with a single SNA configuration.

REFERENCES

1. Banga R J, Chernyak N, Narayan S P, Nguyen S T, Mirkin C A. Liposomal Spherical Nucleic Acids. J. Am. Chem. Soc. 2014 136: 9866-9869.
2. Ding Y and Lawrence C E. A Statistical Sampling Algorithm for RNA Secondary Structure Prediction. Nucleic Acids Res. 2003: 31: 7280-7301.
3. Chabaud M1, Fossiez F, Taupin J L, Miossec P. Enhancing effect of IL-17 on IL-1-induced IL-6 and leukemia inhibitory factor production by rheumatoid arthritis synoviocytes and its regulation by Th2 cytokines. J Immunol. 1998 Jul. 1; 161(1):409-14.
4. Miossec P. Interleukin-17 in rheumatoid arthritis: if T cells were to contribute to inflammation and destruction through synergy. Arthritis Rheum. 2003 March; 48(3): 594-601.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A multiplex antisense oligonucleotide spherical nucleic acid (mASO-SNA), comprising
a core having an oligonucleotide shell comprised of an antisense oligonucleotide 10 to 30 linked nucleosides in length targeted to a first gene and an antisense oligonucleotide 10 to 30 linked nucleosides in length targeted to a second gene, wherein the core is a liposome core and the oligonucleotide shell is positioned on the exterior of the core,
wherein each antisense oligonucleotide comprises at least two modified nucleosides,
wherein each antisense oligonucleotide further comprises a molecular species at the 5' end, 3' end, or 5' and 3' end of the antisense oligonucleotide,
wherein the molecular species is a lipid moiety connected to the antisense oligonucleotide by a linker, wherein the linker comprises hexaethylene glycol.

2. The mASO-SNA of claim 1, wherein the first gene and the second gene are associated with a disease.

3. The mASO-SNA of claim 1, wherein the disease is an inflammatory disorder.

4. The mASO-SNA of claim 1, wherein the disease is psoriasis.

5. The mASO-SNA of claim 1, wherein the first gene is associated with a target pathway and the second gene is associated with the target pathway.

6. The mASO-SNA of claim 1, further comprising an antisense oligonucleotide 10 to 30 linked nucleosides in length targeted to a third gene.

7. The mASO-SNA of claim 1, wherein the first gene is an Interleukin 17 receptor (IL-17RA).

8. The mASO-SNA of claim 1, wherein the second gene is TNF.

9. The mASO-SNA of claim 1, wherein the antisense oligonucleotide targeted to the first gene and the antisense oligonucleotide targeted to the second gene are present in an approximate equimolar amount in the oligonucleotide shell.

10. A method for treating a disorder, comprising:
administering to a subject having a disorder a multiplex antisense oligonucleotide spherical nucleic acid (mASO-SNA), comprising a core having an oligonucleotide shell comprised of an antisense oligonucleotide 10 to 30 linked nucleosides in length targeted to a first gene and an antisense oligonucleotide 10 to 30 linked nucleosides in length targeted to a second gene, wherein the core is a liposome core and the oligonucleotide shell is positioned on the exterior of the core in an effective amount to treat the disorder,
wherein each antisense oligonucleotide comprises at least two modified nucleosides,
wherein each antisense oligonucleotide further comprises a molecular species at the 5' end, 3' end, or 5' and 3' end of the antisense oligonucleotide,
wherein the molecular species is a lipid moiety connected to the antisense oligonucleotide by a linker, wherein the linker comprises hexaethylene glycol.

11. The method of claim 10, wherein the mASO-SNA produces simultaneous mRNA knock-down of the first and second gene.

12. The mASO-SNA of claim 6, wherein the first gene is associated with a target pathway, the second gene is associated with the target pathway, and the third gene is associated with the target pathway.

13. The mASO-SNA of claim 1, wherein the first gene is associated with a target pathway and the second gene is associated with a second target pathway which is not the target pathway associated with the first gene.

14. The mASO-SNA of claim 6, wherein the first gene is associated with a target pathway, the second gene is associated with a second target pathway, and the third gene is associated with a third target pathway, wherein each of the: target pathway; second target pathway; and third target pathway are different target pathways.

15. The mASO-SNA of claim 1, wherein the first gene is an interleukin-4 receptor (IL-4R).

16. The mASO-SNA of claim 1, wherein the second gene is interleukin-1 beta (IL-1β).

17. The mASO-SNA of claim 6, wherein the third gene is connective tissue growth factor (CTGF).

18. The mASO-SNA of claim 6, wherein the antisense oligonucleotide targeted to the first gene, the antisense oligonucleotide targeted to the second gene, and the antisense oligonucleotide targeted to the third gene are present in an approximate equimolar amount in the oligonucleotide shell.

19. A pharmaceutical composition, comprising the mASO-SNA of claim 1.

20. The mASO-SNA of claim 1, wherein the lipid moiety is a cholesterol moiety.

21. The mASO-SNA of claim 1, wherein each antisense oligonucleotide comprises a gap segment consisting of 2 to 8 linked deoxynucleosides, a 5' wing segment consisting of linked nucleosides, and a 3' wing segment consisting of linked nucleosides, wherein the gap segment is positioned between the 5' wing segment and the 3' wing segment, wherein at least one nucleoside of each wing segment comprises a modified nucleotide.

* * * * *